United States Patent
Carling et al.

(10) Patent No.: US 6,960,598 B2
(45) Date of Patent: Nov. 1, 2005

(54) (1,8) NAPHTHYRIDINES AS GABA LIGANDS, THEIR PHARMACEUTICAL COMPOSITIONS AND USES

(75) Inventors: William Robert Carling, Bishops Stortford (GB); Andrew Mitchinson, Sawbridgeworth (GB); Michael Geoffrey Russell, Welwyn Garden City (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 10/483,242

(22) PCT Filed: Jul. 3, 2002

(86) PCT No.: PCT/GB02/03077

§ 371 (c)(1),
(2), (4) Date: Jan. 8, 2004

(87) PCT Pub. No.: WO03/006464

PCT Pub. Date: Jan. 23, 2003

(65) Prior Publication Data

US 2004/0171633 A1 Sep. 2, 2004

(30) Foreign Application Priority Data

Jul. 12, 2001 (GB) ............................................ 0117060

(51) Int. Cl.[7] ...................... A61K 31/44; C07D 471/04; C07D 265/30

(52) U.S. Cl. ...................... 514/300; 546/122; 544/336; 544/106

(58) Field of Search ........................ 546/122; 514/300; 544/336, 106

(56) References Cited

FOREIGN PATENT DOCUMENTS

WO WO 01 38326 A 5/2001

OTHER PUBLICATIONS

Settimo Da A, et al: "Synthesis and Benzodiazepine Receptor Activity of Some 4, 5–Dihydro–1H–Pyrazolo 4,3–C1,8 Naphthyridine Derivatives", Drug Design and Discovery, 1994, vol. 11, pp. 307–328.

Cinone N, et al: "Development of a Unique 3D Interaction Model of Endogenous and Synthetic Peripheral Benzodiazepine Receptor Ligands", Journal of Computer–Aided Molecular Design, 2000, vol. 14, No. 8, pp. 753–768.

Teuber L, et al: "Ligands for the Benzodiazepine Binding Site—A Survey", Current Pharmaceutical Design, 1999, vol. 5, pp. 317–343.

Martin I L, et al: "Benzodiazepine Recognition Site Ligands and GABAA Receptors", Expert Opinion on Therapeutic Patents, 1999, vol. 9, No. 10, pp. 1347–1358.

*Primary Examiner*—Rita Desai
(74) *Attorney, Agent, or Firm*—J. Eric Thies; Melvin Winokur

(57) ABSTRACT

A class of [1,8] naphthyridine analogues which are substituted in the 4-position by a substituted phenyl ring. These compounds are ligands for $GABA_A$ receptors and useful in the therapy of deleterious mental states such as anxiety.

11 Claims, No Drawings

(1,8) NAPHTHYRIDINES AS GABA LIGANDS, THEIR PHARMACEUTICAL COMPOSITIONS AND USES

CROSS REFERENCE TO RELATED APPLICATIONS

This application is a U.S. National Phase application under 35 U.S.C. § 371 of PCT Application No. PCT/GB02/003077, filed Jul. 3, 2002, which claims priority under 35 U.S.C. § 119 from GB Application No. 0117060.4, filed Jul. 12, 2001.

The present invention relates to a class of substituted naphthyridine derivatives and to their use in therapy. More particularly, this invention is concerned with [1,8] naphthyridine analogues which are substituted in the 4-position by a substituted phenyl ring. These compounds are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta\gamma 1$, $\alpha 2\beta 2/3\gamma 2$, $\alpha 3\beta\gamma 2/3$, $\alpha 4\beta\delta$, $\alpha 5\beta 3\gamma 2/3$, $\alpha 6\beta\gamma 2$ and $\alpha 6\beta\delta$. Subtype assemblies containing an α1 subunit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect.

Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the $\alpha 2\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$, or $\alpha 3\beta\gamma 2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Also, agents which are antagonists or inverse agonists at α1 might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse or dependency, including alcohol withdrawal. Selective ligands for $GABA_A$ receptors may also be effective as premedication prior to anaesthesia or minor procedures such as endoscopy, including gastric endoscopy.

The present invention provides a class of naphthyridine derivatives which possess desirable binding properties at various GABA$_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity ($K_i$) for the α2 and/or α3 subunit, as measured in the assay described hereinbelow, of 200 nM or less, typically of 100 nM or less, and ideally of 20 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the α1 subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

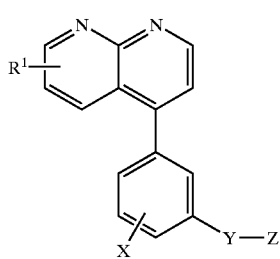

(I)

wherein

X represents hydrogen or halogen;

Y represents an oxygen atom, a —NH— linkage or preferably a chemical bond;

Z represents an optionally substituted aryl or heteroaryl group;

R$^1$ represents hydrogen, hydrocarbon, a heterocyclic group, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, —CR$^a$=NOR$^b$ or CR$^a$=NNHR$^b$; and R$^a$ and R$^b$ independently represent hydrogen, hydrocarbon or a heterocyclic group.

The aryl or heteroaryl group Z in the compounds of formula I above may be unsubstituted, or substituted by one or more substituents. Typically, the group Z will be unsubstituted, or substituted by one or two substituents. Suitably, the group Z is unsubstituted or monosubstituted. Typical substituents on the group Z include halogen, cyano, nitro, amino, formyl, trifluoromethyl, C$_{1-6}$ alkoxy, C$_{2-6}$ alkoxycarbonyl, di(C$_{1-6}$)alkylaminocarbonyl and —CR$^a$=NOR$^b$.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, aryl and aryl(C$_{1-6}$)alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl, butyl and pentyl groups. Particular alkyl groups are methyl, ethyl, n-propyl, isopropyl, isobutyl, tert-butyl and 2,2-dimethylpropyl. Derived expressions such as "C$_{1-6}$ alkoxy", "C$_{1-6}$ alkylamino" and "C$_{1-6}$ alkylsulphonyl" are to be construed accordingly.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Typical examples of C$_{3-7}$ cycloalkyl(C$_{1-6}$)alkyl groups include cyclopropylmethyl, cyclohexylmethyl and cyclohexylethyl.

Particular indanyl groups include indan-1-yl and indan-2-yl.

Particular aryl groups include phenyl and naphthyl, preferably phenyl.

Particular aryl(C$_{1-6}$)alkyl groups include benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyrimidinylmethyl, pyrazinylmethyl, quinolinylmethyl and isoquinolinylmethyl.

The hydrocarbon and heterocyclic groups may in turn be optionally substituted by one or more groups selected from $C_{1-6}$ alkyl, adamantyl, phenyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, aminocarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, $C_{1-6}$ alkyl, aryl or aryl($C_{1-6}$)alkyl.

The term "halogen" as used herein includes fluorine, chlorine, bromine and iodine, especially fluoro or chloro.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In one embodiment, the present invention provides a compound of formula IA, or a salt or prodrug thereof:

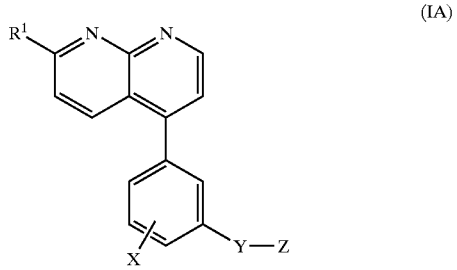

(IA)

wherein X, Y, Z and R$^1$ are as defined above.

Suitably, X represents hydrogen or fluoro.

In a preferred embodiment, Y represents a chemical bond.

In another embodiment, Y represents an oxygen atom.

In a further embodiment, Y represents a —NH— linkage.

Representative values for the substituent Z include phenyl, pyridinyl, thienyl and thiazolyl, any of which groups may be optionally substituted. In a favoured embodiment, Z represents an optionally substituted phenyl group, in particular monosubstituted phenyl.

Examples of typical substituents on the group Z include fluoro, chloro, methoxy, trifluoromethyl, cyano, nitro, amino, formyl, methoxycarbonyl and —CH=NOH; especially fluoro or cyano; and more especially cyano.

Specific values of Z include trifluoromethylphenyl, cyanophenyl, (cyano)(fluoro)phenyl, nitrophenyl, methoxyphenyl, pyridinyl, fluoro-pyridinyl, (amino)(chloro)pyridinyl, cyano-pyridinyl, cyano-thienyl, formyl-thienyl, methoxycarbonyl-thienyl, thienyl-CH=NOH and thiazolyl.

Individual values of Z include 2-cyanophenyl, 2-cyano-4-fluorophenyl, pyridin-2-yl, pyridin-3-yl, pyridin-4-yl and 3-cyanopyridin-2-yl.

A particular value of Z is cyanophenyl, especially 2-cyanophenyl.

Suitably, R$^1$ represents hydrocarbon, a heterocyclic group, halogen, trifluoromethyl, cyano, —OR$^a$, —COR$^a$, —CO$_2$R$^a$ or —CR$^a$=NOR$^b$.

Typical values of R$^a$ include hydrogen and $C_{1-6}$ alkyl. Suitably, R$^a$ represents hydrogen or methyl.

Typical values of R$^b$ include hydrogen, $C_{1-6}$ alkyl, hydroxy($C_{1-6}$)alkyl and di($C_{1-6}$)alkylamino($C_{1-6}$)alkyl. Suitably, R$^b$ represents hydrogen, methyl, ethyl, hydroxyethyl or dimethylaminoethyl. Particular values of R$^b$ include hydrogen, hydroxyethyl and dimethylaminoethyl.

Illustrative values of R$^1$ include $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)alkoxy($C_{1-6}$)alkyl, aryl, heteroaryl, $C_{1-6}$ alkyl-heteroaryl, heteroaryl($C_{1-6}$)alkyl, halogen, cyano, trifluoromethyl, $C_{1-6}$ alkoxy, formyl, $C_{2-6}$ alkylcarbonyl, $C_{2-6}$ alkoxycarbonyl and —CR$^a$=NOR$^b$, in which R$^a$ and R$^b$ are as defined above.

Specific values of R$^1$ include methyl, fluoromethyl, difluoromethyl, trifluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, pyridinyl, furyl, thienyl, oxazolyl, methylthiazolyl, methyloxadiazolyl, imidazolylmethyl, triazolylmethyl, chloro, methoxy, cyano, formyl, acetyl, methoxycarbonyl and —CR$^2$=NOR$^3$, in which R$^2$ represents hydrogen or methyl, and R$^3$ represents hydrogen, hydroxyethyl or dimethylaminoethyl.

In one embodiment, R$^1$ represents methyl. In another embodiment, R$^1$ represents 2-hydroxyprop-2-yl. In a further embodiment, R$^1$ represents trifluoromethyl.

A particular sub-class of compounds according to the invention is represented by the compounds of formula IIA, and salts and prodrugs thereof:

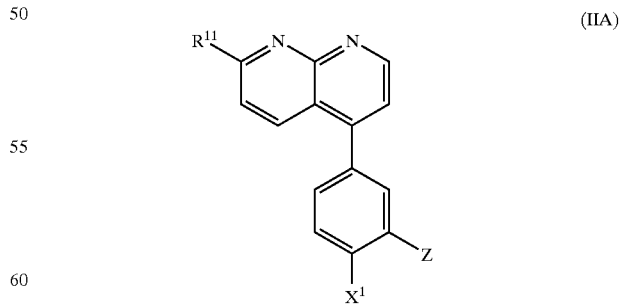

(IIA)

wherein

X$^1$ represents hydrogen or fluoro;

Z is as defined above;

R$^{11}$ represents $C_{1-6}$ alkyl, halo($C_{1-6}$)alkyl, dihalo($C_{1-6}$)alkyl, hydroxy($C_{1-6}$)alkyl, $C_{1-6}$ alkoxy($C_{1-6}$)alkyl, di($C_{1-6}$)

alkoxy(C$_{1-6}$)alkyl, aryl, heteroaryl, C$_{1-6}$ alkyl-heteroaryl, heteroaryl(C$_{1-6}$)alkyl, halogen, cyano, trifluoromethyl, C$_{1-6}$ alkoxy, formyl, C$_{2-6}$ alkylcarbonyl, C$_{2-6}$ alkoxycarbonyl or —CR$^4$=NOR$^5$;

R$^4$ represents hydrogen or C$_{1-6}$ alkyl; and

R$^5$ represents hydrogen, C$_{1-6}$ alkyl, hydroxy(C$_{1-6}$)alkyl or di(C$_{1-6}$)alkylamino(C$_{1-6}$)alkyl.

In one embodment, X$^1$ represents hydrogen. In another embodiment, X$^1$ represents fluoro.

Suitably, R$^4$ represents hydrogen or methyl.

Suitably, R$^5$ represents hydrogen, methyl, ethyl, hydroxyethyl or dimethylaminoethyl. Particular values of R$^5$ include hydrogen, hydroxyethyl and dimethylaminoethyl.

Where R$^{11}$ represents heteroaryl, this group is suitably pyridinyl, furyl, thienyl or oxazolyl.

Where R$^{11}$ represents C$_{1-6}$ alkyl-heteroaryl, this group is suitably methylthiazolyl (e.g. 2-methylthiazol-5-yl) or methyloxadiazolyl (e.g. 3-methyl-[1,2,4]oxadiazol-5-yl).

Where R$^{11}$ represents heteroaryl(C$_{1-6}$)alkyl, this group is suitably imidazolylmethyl or triazolylmethyl.

Representative values of R$^{11}$ include methyl, fluoromethyl, difluoromethyl, trifluoromethyl, hydroxymethyl, methoxymethyl, dimethoxymethyl, hydroxyethyl (especially 1-hydroxyethyl), fluoroethyl (especially 1-fluoroethyl), difluoroethyl (especially 1,1-difluoroethyl), dimethoxyethyl (especially 1,1-dimethoxyethyl), isopropyl, hydroxypropyl (especially 2-hydroxyprop-2-yl), fluoropropyl (especially 2-fluoroprop-2-yl), tert-butyl, pyridinyl, furyl, thienyl, oxazolyl, methylthiazolyl, methyloxadiazolyl, imidazolylmethyl, triazolylmethyl, chloro, methoxy, cyano, formyl, acetyl, methoxycarbonyl and —CR$^2$=NOR$^3$, in which R$^2$ and R$^3$ are as defined above.

In the preceding compounds of formulae I, IA and IIA, Z is aptly an optionally substituted phenyl group wherein there are one or two optional substituents selected from fluorine, cyano, trifluoromethyl; or a pharmaceutically acceptable salt thereof and is preferably a phenyl, monofluorophenyl, difluorophenyl, trifluoromethylphenyl, cyanophenyl or cyanofluorophenyl group; or a pharmaceutically acceptable salt thereof.

In one embodiment, R$^{11}$ represents methyl. In another embodiment, R$^{11}$ represents 2-hydroxyprop-2-yl. In a further embodiment, R$^{11}$ represents trifluoromethyl.

A representative subset of the compounds of formula IIA above is represented by the compounds of formula IIB, and salts and prodrugs thereof:

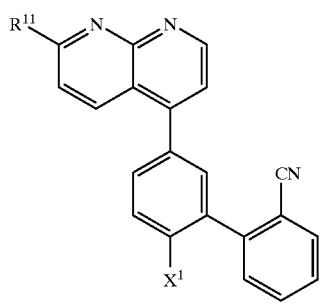

(IIB)

wherein X$^1$ and R$^{11}$ are as defined with reference to formula IIA above.

Specific compounds within the scope of the present invention include:

3'-(7-methyl-[1,8]naphthyridin-4-yl)biphenyl-2-carbonitrile;

2'-fluoro-5'-(7-methyl-[1,8]naphthyridin-4-yl)biphenyl-2-carbonitrile;

6,2'-difluoro-5'-(7-trifluoromethyl[1,8]naphthyridin-4-yl)biphenyl-2-carbonitrile;

5-(4-fluoro-3-pyridin-3-ylphenyl)-2-trifluoromethyl[1,8]naphthyridine;

5-(4-fluoro-3-pyridin-4-ylphenyl)-2-trifluoromethyl[1,8]naphthyridine;

5-[4-fluoro-3-(3-fluoropyridin-2-yl)phenyl]-2-trifluoromethyl[1,8]naphthyridine;

3,2'-difluoro-5'-(7-trifluoromethyl-[1,8]naphthyridin-4-yl)biphenyl-2-carbonitrile;

4,2'-difluoro-5'-(7-trifluoromethyl-[1,8]naphthyridin-4-yl)biphenyl-2-carbonitrile;

5,2'-difluoro-5'-(7-trifluoromethyl-[1,8]naphthyridin-4-yl)biphenyl-2-carbonitrile;

4-fluoro-3'-(7-trifluoromethyl[1,8]naphthyridin-4-yl)biphenyl-2-carbonitrile;

5-(2-fluoro-3-pyridin-2-ylphenyl)-2-trifluoromethyl-[1,8]naphthyridine;

5-(2-fluoro-3-pyridin-3-ylphenyl)-2-trifluoromethyl-[1,8]naphthyridine;

5-(2-fluoro-3-pyridin-4-ylphenyl)-2-trifluoromethyl-[1,8]naphthyridine;

5-(2,4-difluoro-3-pyridin-3-ylphenyl)-2-trifluoromethyl[1,8]naphthyridine;

5-(2,4-difluoro-3-pyridin-4-ylphenyl)-2-trifluoromethyl[1,8]naphthyridine;

3'-fluoro-5'-(7-trifluoromethyl-[1,8]naphthyridin-4-yl)biphenyl-2-carbonitrile;

2'-fluoro-5'-(7-trifluoromethyl-[1,8]naphthyridin-4-yl)biphenyl-3-carbonitrile;

2'-fluoro-5'-(7-trifluoromethyl[1,8]naphthyridin-4-yl)biphenyl-4-carbonitrile;

5-(6-fluoro-2'-methanesulfonylbiphenyl-3-yl)-2-trifluoromethyl[1,8]-naphthyridine;

5-(3'-methoxybiphenyl-3-yl)-2-trifluoromethyl[1,8]naphthyridine;

5-[4-fluoro-3-(3-fluoropyridin-4-yl)phenyl]-2-trifluoromethyl[1,8]naphthyridine;

2-[2-fluoro-5-(7-trifluoromethyl[1,8]naphthyridin-4-yl)phenyl]nicotinonitrile;

2-[2-fluoro-5-(7-trifluoromethyl[1,8]naphthyridin-4-yl)phenyl]nicotinamide;

5-(3-fluoro-5-pyridin-3-ylphenyl)-2-trifluoromethyl[1,8]naphthyridine;

5-(4-fluoro-3-pyrimidin-4-ylphenyl)-2-trifluoromethyl[1,8]naphthyridine;

5-[3-(2-methyl-2H-tetrazol-5-yl)phenyl]-2-trifluoromethyl[1,8]naphthyridine;

5-(3-furan-2-ylphenyl)-2-trifluoromethyl[1,8]naphthyridine;

5-[3-(pyridin-2-ylmethoxy)phenyl]-2-trifluoromethyl[1,8]naphthyridine;

5-(4-fluoro-3-morpholin-4-ylmethylphenyl)-2-trifluoromethyl[1,8]naphthyridine;

5-[3-(3,5-difluoropyridin-2-yl)-4-fluorophenyl]-2-trifluoromethyl[1,8]-naphthyridine;

2'-fluoro-5'-(7-trifluoromethyl[1,8]naphthyridin-4-yl)biphenyl-2-carbonitrile;

5-(4-fluoro-3-pyridin-2-yl)-2-trifluoromethyl[1,8]naphthyridine;

6,2'-difluoro-5'-(7-trifluoromethyl[1,8]naphthyridin-4-yl)biphenyl-3-carbonitrile;

5-(4-fluoro-3-methoxyphenyl)-2-trifluoromethyl[1,8]naphthyridine;

5-(3'-chloro-6-fluorobiphenyl-3-yl)-2-trifluoromethyl[1,8]naphthyridine;

N-[2'-fluoro-5'-(7-trifluoromethyl[1,8]naphthyridin-4-yl)
biphenyl-3-yl]acetamide;
1-[2'-fluoro-5'-(7-trifluoromethyl[1,8]naphthyridin-4-yl)
biphenyl-3-yl]ethanone;
5-(6-fluoro-2'-methoxybiphenyl-3-yl)-2-trifluoromethyl[1,
8]naphthyridine;
5-(6-fluoro-2'-trifluoromethylbiphenyl-3-yl)-2-
trifluoromethyl[1,8]naphthyridine;
5-(4-fluoro-3-pyrimidin-5-ylphenyl)-2-trifluoromethyl[1,8]
naphthyridine;
5-(4-fluoro-3-quinolin-6-ylphenyl)-2-trifluoromethyl[1,8]
naphthyridine;
5-(4-fluoro-3-thiazol-2-ylphenyl)-2-trifluoromethyl[1,8]
naphthyridine;
5-(4-fluoro-3-pyrazin-2-ylphenyl)-2-trifluoromethyl[1,8]
naphthyridine;
5-(4-fluoro-3-trifluoromethylphenyl)-2-trifluoromethyl[1,8]
naphthyridine;
2-fluoro-5-(7-trifluoromethyl[1,8]naphthyridine-4-yl)
benzonitrile;
2-[6-(7-trifluoromethyl[1,8]naphthyridin-4-yl)pyridin-2-yl]
benzonitrile;
5-[4-fluoro-3-(pyridin-3-ylmethoxy)phenyl]-2-
trifluoromethyl[1,8]naphthyridine;
5-[4-fluoro-3-(pyridin-4-ylmethoxy)phenyl]-2-
trifluoromethyl[1,8]naphthyridine;
5-[4-fluoro-3-(pyridin-2-yloxy)phenyl]-2-trifluoromethyl
[1,8]naphthyridine;
[2-fluoro-5-(7-trifluoromethyl[1,8]naphthyridin-4-yl)
phenoxy]acetonitrile;
2-[2-fluoro-5-(7-trifluoromethyl[1,8]naphthyridin-4-yl)
phenoxy]-N,N-dimethylacetamide;
5-[4-fluoro-3-(2-methyl-2H-[1,2,4]triazol-3-ylmethoxy)
phenyl]-2-trifluoromethyl[1,8]naphthyridine;
5-[4-fluoro-3-(1-methyl-1H-[1,2,3]triazol-4-ylmethoxy)
phenyl]-2-trifluoromethyl[1,8]naphthyridine;
5-(4-fluorophenyl)-2-trifluoromethyl[1,8]naphthyridine;
2'-fluoro-5'-[7-(2-fluorophenyl)-[1,8]naphthyridin-4-yl]
biphenyl-2-carbonitrile;
2'-fluoro-5'-[7-(pyridin-3-yl)-[1,8]naphthyridin-4-yl]
biphenyl-2-carbonitrile;
2'-fluoro-5'-[7-(thiazol-2-yl)-[1,8]naphthyridin-4-yl]
biphenyl-2-carbonitrile;
5'-[7-acetyl-[1,8]naphthyridin-4-yl]-2'-fluorobiphenyl-2-
carbonitrile;
2'-fluoro-5'-[7-(1-hydroxy-1-methylethyl)-[1,8]
naphthyridin-4-yl]biphenyl-2-carbonitrile;
and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 50 nM or less, preferably 10 nM or less, and more preferably 5 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk-fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds in accordance with the present invention may be prepared by a process which comprises reacting a compound of formula III with a compound of formula IV:

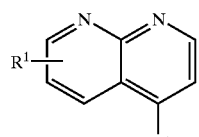

(III)

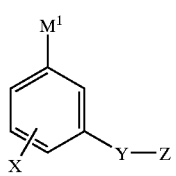

(IV)

wherein X, Y, Z and $R^1$ are as defined above, $L^1$ represents a suitable leaving group, and $M^1$ represents a boronic acid moiety —$B(OH)_2$ or a cyclic ester thereof formed with an organic diol, e.g. pinacol, or $M^1$ represents —$Sn(Alk)_3$ in which Alk represents a $C_{1-6}$ alkyl group, typically n-butyl; in the presence of a transition metal catalyst.

The leaving group $L^1$ is typically a halogen atom, e.g. chloro.

The transition metal catalyst of use in the reaction between compounds III and IV is suitably tris(dibenzylideneacetone)di-palladium(0). The reaction is conveniently carried out at an elevated temperature in a solvent such as tetrahydrofuran, advantageously in the presence of potassium fluoride and tri-tert-butylphosphine.

In an alternative procedure, the compounds according to the present invention in which Y represents a chemical bond may be prepared by a process which comprises reacting a compound of formula V with a compound of formula VI:

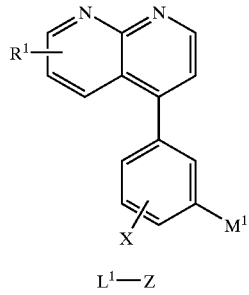

(V)

$L^1$—Z (VI)

wherein X, Z, $R^1$, $L^1$ and $M^1$ are as defined above; in the presence of a transition metal catalyst; under conditions analogous to those described above for the reaction between compounds III and IV.

In another procedure, the compounds according to the present invention in which Y represents an oxygen atom may be prepared by a process which comprises reacting a compound of formula VI as defined above with a compound of formula VII:

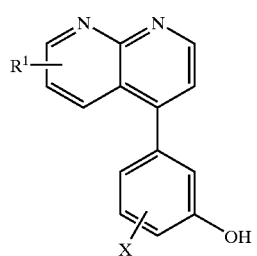

(VII)

wherein X and $R^1$ are as defined above.

The reaction is conveniently carried out under basic conditions, e.g. using sodium hydride in a solvent such as N,N-dimethylformamide, typically at an elevated temperature which may be in the region of 120° C.

In a further procedure, the compounds according to the present invention in which Y represents a —NH— linkage may be prepared by a process which comprises reacting a compound of formula VI as defined above with a compound of formula VIII:

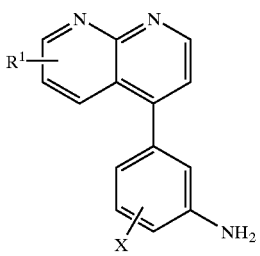

(VIII)

wherein X and $R^1$ are as defined above.

In relation to the reaction between compounds VI and VIII, the leaving group $L^1$ in the compounds of formula VI may suitably represent fluoro.

The reaction between compounds VI and VIII is conveniently carried out by heating the reactants, typically at a temperature in the region of 120° C., in a solvent such as N,N-dimethylformamide.

Where $M^1$ in the intermediates of formula IV and V above represents a cyclic ester of a boronic acid moiety —$B(OH)_2$ formed with pinacol, the relevant compound IV or V may be prepared by reacting bis(pinacolato)diboron with a compound of formula IVA or VA:

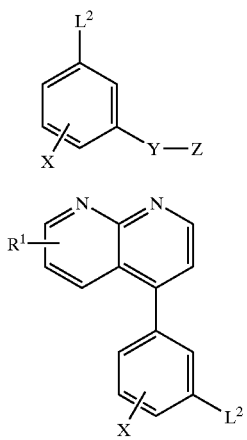

(IVA)

(VA)

wherein X, Y, Z and R¹ are as defined above, and L² represents hydroxy or a suitable leaving group; in the presence of a transition metal catalyst.

Where L² represents a leaving group, this is typically trifluoromethanesulfonyloxy (triflyloxy); or a halogen atom such as bromo.

The transition metal catalyst of use in the reaction between bis(pinacolato)diboron and compound IVA or VA is suitably dichloro[1,1'-bis(diphenylphosphino)ferrocene]palladium(II). The reaction is conveniently carried out at an elevated temperature in a solvent such as 1,4-dioxane, optionally in admixture with dimethylsulfoxide, typically in the presence of 1,1'-bis(diphenylphosphino)ferrocene and/or potassium acetate.

Where L² in the intermediates of formula VA above represents triflyloxy, the relevant compound VA may be prepared by reacting the appropriate compound of formula VII as defined above with N-phenyl-triflimide, typically in the presence of triethylamine. Analogous conditions may be utilised for converting an intermediate of formula IVA above wherein L² represents hydroxy into the corresponding compound wherein L² represents triflyloxy.

The intermediates of formula VII above may suitably be prepared from the appropriate methoxy-substituted precursor of formula IX:

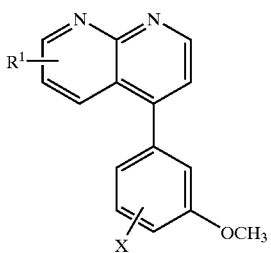

(IX)

wherein X and R¹ are as defined above; by treatment with boron tribromide or with hydrogen bromide.

The intermediates of formula VIII and IX above may be prepared by reacting a compound of formula III as defined above with the appropriate compound of formula X:

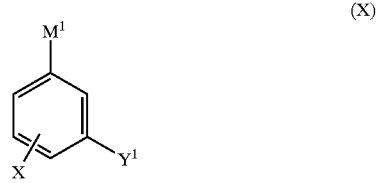

(X)

wherein X and M¹ are as defined above, and Y¹ represents amino or methoxy; in the presence of a transition metal catalyst; under conditions analogous to those described above for the reaction between compounds III and IV.

In relation to the reaction between compounds III and X, the transition metal catalyst utilised is suitably tetrakis(triphenylphosphine)palladium(0), in which case the reaction is conveniently effected at an elevated temperature in a solvent such as toluene/ethanol, typically in the presence of sodium carbonate.

In a yet further procedure, the compounds according to the present invention wherein X represents hydrogen and R¹ represents an aryl or heteroaryl moiety may be prepared by a process which comprises reacting a compound of formula XI with a compound of formula XII:

(XI)

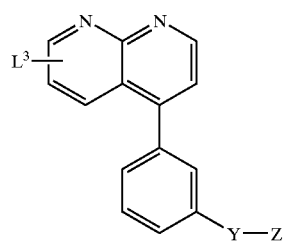

(XII)

wherein Y and Z are as defined above, R¹ᵃ represents an aryl or heteroaryl moiety, and L³ represents a suitable leaving group; in the presence of a transition metal catalyst.

The leaving group L³ is typically a halogen atom, e.g. chloro.

The transition metal catalyst of use in the reaction between compounds XI and XII is suitably tris(dibenzylideneacetone)dipalladium(0), in which case the reaction is conveniently effected at an elevated temperature in a solvent such as 1,4-dioxane, typically in the presence of tri-tert-butylphosphine and cesium carbonate.

Where L³ in the compounds of formula XII above represents a halogen atom, these compounds correspond to compounds of formula I as defined above wherein R¹ represents halogen, and they may therefore be prepared by any of the methods described above for the preparation of the compounds according to the invention.

The intermediates of formula III above may be prepared by the procedure described in *Aust. J. Chem.*, 1984, 37, 1065–73, or by methods analogous thereto.

Where they are not commercially available, the starting materials of formula VI, X and XI may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I wherein R¹ represents $C_{2-6}$ alkoxycarbonyl initially obtained may be reduced with lithium aluminium hydride to the corresponding compound of formula I wherein $R^1$ represents hydroxymethyl. The latter compound may then be oxidised to the corresponding compound of formula I wherein $R^1$ represents formyl by treatment with manganese dioxide. The formyl derivative thereby obtained may be condensed with a hydroxylamine derivative of formula $H_2N$—$OR^b$ to provide a compound of formula I wherein $R^1$ represents —CH=$NOR^b$. Alternatively, the compound of formula I wherein $R^1$ represents formyl may be reacted with a Grignard reagent of formula $R^a$MgBr to afford a compound of formula I wherein $R^1$ represents —CH(OH)$R^a$, and this compound may in turn be oxidised using manganese dioxide to the corresponding compound of formula I wherein $R^1$ represents —$COR^a$. The latter compound may then be condensed with a hydroxylamine derivative of formula $H_2N$—$OR^b$ to provide a compound of formula I wherein $R^1$ represents —$CR^a$=$NOR^b$.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human $GABA_A$ receptors containing the α2 or α3 subunit stably expressed in Ltk-cells.

Reagents

Phosphate buffered saline (PBS).

Assay buffer: 10 mM $KH_2PO_4$, 100 mM KCl, pH 7.4 at room temperature.

[$^3$H]-Flumazenil (18 nM for α1β3γ2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 18 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compounds of the accompanying Examples were tested in the above assay, and all were found to possess a $K_i$ value for displacement of [$^3$H]-flumazenil from the α2 and/or α3 subunit of the human $GABA_A$ receptor of 100 nM or less.

EXAMPLE 1

3'-(7-Methyl-[1,8]naphthyridin-4-yl)biphenyl-2-carbonitrile a) 3'-Aminobiphenyl-2-carbonitrile A mixture of 2-bromobenzonitrile (9.1 g, 50 mmol), 3-aminobenzeneboronic acid monohydrate (11.6 g, 75 mmol) and tetrakis(triphenylphosphine)palladium(0) (1.73 g, 1.5 mmol) in 1,2-dimethoxyethane (50 ml) and 2M sodium carbonate solution (25 ml) was heated at 80° C. for 20 h. After cooling to ambient temperature the reaction was partitioned between ethyl acetate (400 ml) and water (400 ml). The organics were washed with brine (400 ml), dried over anhydrous sodium sulfate, filtered and concentrated in vacuo. Purification of the residue by chromatography on silica gel, eluting with isohexane on a gradient of ethyl acetate (0–25%) gave 3'-aminobiphenyl-2-carbonitrile as a colourless oil that solidified on standing to afford a white solid (9.5 g, 98%): $\delta_H$ (400 MHz, $CDCl_3$) 3.79 (2H, br), 6.75 (1H, ddd, J 8, 3 and 1), 6.84 (1H, dd, J 3 and 3), 6.92 (1H, dd, J 8 and 3), 7.25 (1H, dd, J 8 and 8), 7.40 (1H, ddd, J 8, 8 and 1), 7.50 (1H, dd, J 8 and 1), 7.62 (1H, ddd, J 8, 8 and 1), 7.73 (1H, dd, J 8 and 1).

b) 3'-Hydroxybiphenyl-2-carbonitrile

A solution of 3'-aminobiphenyl-2-carbonitrile (10.9 g, 56 mmol) in 1,4-dioxane (30 ml) was treated with a solution of 25% aqueous sulfuric acid (150 ml). The resulting suspension was cooled to 0° C. before being treated dropwise over 10 minutes with a solution of sodium nitrite (4.6 g, 67 mmol)

in water (10 ml). After stirring at 0° C. for 30 minutes the reaction was poured into hot (70° C.) water (500 ml). On cooling to ambient temperature the product was extracted into ethyl acetate (500 ml), the organics were washed with water (300 ml), brine (300 ml) and dried over anhydrous sodium sulfate. Filtration and concentration in vacuo afforded 3'-hydroxybiphenyl-2-carbonitrile as a dark oil (7.1 g, 65%): $\delta_H$ (400 MHz, CDCl$_3$) 5.40 (1H, br), 6.92 (1H, ddd, J 8, 3 and 1), 7.04 (1H, dd, J 3 and 3), 7.11 (1H, ddd, J 8, 3 and 1), 7.35 (1H, dd, J 8 and 8), 7.44 (1H, ddd, J 8, 8 and 1), 7.51 (1H, dd, J 8 and 1), 7.64 (1H, ddd, J 8, 8 and 1), 7.75 (1H, dd, J 8 and 1).

c) Trifluoromethanesulfonic acid 2'-cyanobiphenyl-3-yl ester

3'-Hydroxybiphenyl-2-carbonitrile (0.48 g, 2.47 mmol) and dry pyridine (0.98 g, 12.35 mmol) were dissolved in dichloromethane (7 ml) and cooled to 0° C. before dropwise addition of trifluoromethanesulfonic anhydride (1.04 g, 3.70 mmol) over 5 min. The mixture was stirred at 0° C. for 10 min and then at 25° C. for 1 h. The solvent was evaporated in vacuo and the residue partitioned between ethyl acetate (200 ml) and water (150 ml). The organic layer was washed with brine (150 ml), dried over anhydrous sodium sulfate and evaporated to give a brown oil. Purification by silica gel chromatography eluting with isohexane on a gradient of ethyl acetate (0–30%) gave trifluoromethanesulfonic acid 2'-cyanobiphenyl-3-yl ester as a yellow oil (544 mg, 67%): $\delta_H$ (400 MHz, CDCl$_3$) 7.37 (1H, ddd, J 8, 3 and 1), 7.39 (1H, dd, J 3 and 3), 7.50–7.60 (2H, m), 7.61–7.65 (2H, m), 7.64 (1H, td, J 8 and 1), 7.80 (1H, dd, J 8 and 1).

d) 3'-(4,4,5,5-Tetramethyl-[1,3,2]dioxaborolan-2-yl) biphenyl-2-carbonitrile

Trifluoromethanesulfonic acid 2'-cyanobiphenyl-3-yl ester (0.55 g, 1.66 mmol), potassium acetate (0.49 g, 4.98 mmol) and bis(pinacolato)diboron (0.55 g, 2.16 mmol) were dissolved in 1,4-dioxane (10 ml) and the mixture degassed with N$_2$ for 15 min. Dichloro[1,1'-bis(diphenylphosphino) ferrocene]palladium(II) dichloromethane adduct (41 mg, 0.05 mmol) and 1,1'-bis(diphenylphosphino)ferrocene (28 mg, 0.05 mmol) were then added and the mixture heated at 85° C. for 18 h. The mixture was cooled to ambient temperature, filtered and the filter cake washed with diethyl ester. The filtrate was evaporated to dryness and partitioned between diethyl ether (25 ml) and 1N sodium hydroxide solution (25 ml). The aqueous layer was washed with more diethyl ether then made acidic (pH 6) with 4N hydrochloric acid. The resulting solid was collected by filtration and dried in vacuo to give 3'-(4,4,5,5-tetramethyl-[1,3,2] dioxaborolan-2-yl)biphenyl-2-carbonitrile as a cream-coloured solid (430 mg, 85%): $\delta_H$ (400 MHz, CDCl$_3$) 1.36 (12H, s), 7.43 (1H, ddd, J 8, 8 and 1.5), 7.48–7.57 (2H, m), 7.62 (2H, ddd, J 8, 8 and 1.5), 7.68–7.71 (1H, m), 7.74–7.77 (1H, m), 7.87–7.90 (1H, m), 7.92–7.94 (1H, m).

e) 3'-(7-Methyl-[1,8]naphthyridin-4-yl)biphenyl-2-carbonitrile

A mixture of tris(dibenzylideneacetone)dipalladium(0) (23 mg, 0.025 mmol), 3'-(4,4,5,5-tetramethyl[1,3,2] dioxaborolan-2-yl)biphenyl-2-carbonitrile (384 mg, 1.3 mmol), potassium fluoride (161 mg, 2.8 mmol) and 5-chloro-2-methyl-[1,8]naphthyridine (prepared as described by G. B. Barlin and W. L. Tan, *Aust. J. Chem.*, 1984, 37, 1065–73; 150 mg, 0.84 mmol) was degassed by evacuating the reaction vessel and refilling it with nitrogen. Tri-tert-butylphosphine (0.50 ml of a 0.1 M solution in THF) and THF (15 ml) were added, and the mixture was degassed via three "freeze-thaw" cycles before stirring under nitrogen for 18 h. The solvent was removed in vacuo, and the residue was purified by flash chromatography on silica gel, eluting with 10% to 100% EtOAc in dichloromethane, yielding 3'-(7-methyl-[1,8]naphthyridin-4-yl)biphenyl-2-carbonitrile as a white solid (22 mg, 8%): $\delta_H$ (400 MHz, CDCl$_3$) 2.83 (3H, s), 7.40 (1H, d, J 8.2), 7.45 (1H, d, J 4.3), 7.48–7.52 (1H, m), 7.57–7.60 (1H, m), 7.59 (1H, s), 7.67–7.71 (4H, m), 7.82 (1H, dd, J 0.8 and 7.8), 8.36 (1H, d, J 8.6), 9.11 (1H, d, J 4.3); m/z (ES$^+$) 322 [MH]$^+$.

EXAMPLE 2

2'-Fluoro-5'-(7-methyl-[1,8]naphthyridin-4-yl) biphenyl-2-carbonitrile a) 2-(2-Fluoro-5-nitrophenyl)-4,4,5,5-tetramethyl-[1,3,2] dioxaborolane A mixture of 2-bromo-1-fluoro-4-nitrobenzene (prepared according to the procedure of Groweiss in *Org. Proc. Res. Dev.*, 2000, 4(1), 30–33) (66 g, 300 mmol), potassium acetate (58.9 g, 600 mmol), bis(pinacolato)diboron (83.8 g, 330 mmol) and dichloro[1,1'-bis(diphenylphosphino) ferrocene]-palladium(II) dichloromethane adduct (7.35 g, 9 mmol) in 1,4-dioxane (900 ml containing 18 ml dimethylsulfoxide) was degassed with nitrogen for 1 h then heated at 90° C. for 14 h. The reaction was cooled to ambient temperature and then concentrated in vacuo. The residue was stirred with 2N sodium hydroxide (1 l) for 10 min then filtered. The filtrate was extracted with diethyl ether (2×750 ml) and the organics discarded. The aqueous component was cooled to 0° C. then treated with 36% hydrochloric acid (ca. 175 ml) added dropwise over 15 min until pH 5. The resulting precipitate was allowed to stand at 0° C. for 2 h then filtered and washed with ice-cold water. The sand-coloured solid was dried under vacuum (300 mmHg) over phosphorus pentoxide to afford 2-(2-fluoro-5-nitrophenyl)-4,4,5,5-tetramethyl-[1,3,2]dioxaborolane (76.1 g, 95%): $\delta_H$ (400 MHz, CDCl$_3$) 1.38 (12H, s), 7.17 (1H, dd, J 9 and 9), 8.32 (1H, ddd, J 9, 5 and 3), 8.64 (1H, dd, J 5 and 3).

b) 2'-Fluoro-5'-nitrobiphenyl-2-carbonitrile

A mixture of 2-bromobenzonitrile (34.6 g, 190 mmol), 2-(2-fluoro-5-nitrophenyl)-4,4,5,5-tetramethyl-[1,3,2] dioxaborolane (76.1 g, 285 mmol) and potassium fluoride (36.4 g, 627 mmol) in tetrahydrofuran (600 ml) was degassed with nitrogen for 30 min then treated with tris (dibenzylideneacetone)dipalladium(0) (1.74 g, 1.9 mmol) followed by tri-tert-butylphosphine (38 ml of a 0.1M solution in 1,4-dioxane, 3.8 mmol) and then the reaction was stirred at ambient temperature for 30 min before heating at 50° C. for 1 h to complete the coupling. The slurry-like reaction mixture was then diluted with water (3 l) and stirred at ambient temperature for 90 min. The resulting solid was collected by filtration, washed with water then with isohexane and finally dried under vacuum over phosphorus pentoxide to afford 2'-fluoro-5'-nitrobiphenyl-2-carbonitrile as a beige solid (46 g, 100%): $\delta_H$ (360 MHz, CDCl$_3$) 7.37–7.42 (1H, m), 7.53 (1H, d, J 8), 7.59 (1H, td, J 8 and 1), 7.75 (1H, td, J 8 and 1), 7.83 (1H, dd, J 8 and 1), 8.35–8.39 (2H, m).

c) 5'-Amino-2'-fluorobiphenyl-2-carbonitrile

A cooled (0° C.) suspension of 2'-fluoro-5'-nitrobiphenyl-2-carbonitrile (24.2 g, 100 mmol) in ethanol (150 ml) and tetrahydrofuran (150 ml) was treated with tin(II) chloride dihydrate (67.7 g, 300 mmol) and the mixture was stirred to ambient temperature over 12 h. The solvent was removed in vacuo and the residue treated with ice-cold 2N sodium hydroxide (750 ml). The resulting slurry was stirred for 60 min then extracted with dichloromethane (2×400 ml). The organics were combined, washed with water, brine, dried over anhydrous magnesium sulfate, filtered and concentrated to give a red solid. Crystallisation from toluene gave 5'-amino-2'-fluorobiphenyl-2-carbonitrile as a cream-coloured solid (16 g, 75%): $\delta_H$ (400 MHz, CDCl$_3$) 3.65 (2H, br), 6.67–6.73 (2H, m), 7.00 (1H, t, J 9), 7.44–7.49 (2H, m), 7.64 (1H, td, J 9 and 2), 7.75 (1H, dd, J 8 and 2); m/z (ES$^+$) 213 (M$^+$+H).

d) 5'-Bromo-2'-fluorobiphenyl-2-carbonitrile

A solution of 5'-amino-2'-fluorobiphenyl-2-carbonitrile (7.85 g, 37 mmol) in 1,4-dioxane (25 ml) was treated with 48% hydrobromic acid (125 ml) and the resulting suspension stirred and cooled to 3° C. (internal temperature). A solution of sodium nitrite in water (5 ml) was then added dropwise over 20 min keeping the internal temperature <5° C. Stirring at <5° C. was continued for 2 h before pouring the reaction into a cooled (5° C.) solution of freshly purified copper(I) bromide (6.37 g, 44 mmol) in 48% hydrobromic acid (50 ml). The resulting purple reaction mixture was stirred at 5° C. for 10 min then warmed to 50° C. for 20 min. The reaction was diluted with ice-cold water (500 ml) and extracted with ethyl acetate (2×250 ml). The organics were combined, washed with 5% aqueous sodium sulfite, saturated aqueous ammonium chloride, dried over anhydrous magnesium sulfate, filtered and pre-adsorbed onto silica. Purification by chromatography on silica eluting with isohexane (containing 1% methanol) on a gradient of ethyl acetate (2–10%) afforded a colourless oil which crystallised on standing to give 5'-bromo-2'-fluorobiphenyl-2-carbonitrile as a white solid (6.5 g, 64%): $\delta_H$ (400 MHz, CDCl$_3$) 7.09–7.14 (1H, m), 7.45–7.57 (4H, m), 7.66 (1H, td, J 8 and 2), 7.77 (1H, dd, J 8 and 2).

e) 2'-Fluoro-5'-(4,4,5,5-tetramethyl-[1,3,2]dioxaborolan-2-yl)biphenyl-2-carbonitrile A mixture of 5'-bromo-2'-fluorobiphenyl-2-carbonitrile (1.1 g, 4 mmol), potassium acetate (1.18 g, 12 mmol) and bis(pinacolato)diboron (1.17 g, 4.6 mmol) was dissolved in 1,4-dioxane (15 ml) containing 1% v/v dimethylsulfoxide (15 ml) and this solution was degassed with nitrogen for 5 min. Dichloro[1,1'-bis(diphenylphosphino)ferrocene]palladium (II) dichloromethane adduct (98 mg, 0.12 mmol) was then added and the mixture heated at 90° C. for 16 h. After cooling to ambient temperature the reaction was partitioned between ethyl acetate and water. The organic phase was washed with brine, dried over anhydrous magnesium sulfate, filtered and pre-adsorbed onto silica. Purification by chromatography on silica eluting with isohexane on a gradient of ethyl acetate (2–10%) gave a colourless oil that crystallised on standing to furnish 2'-fluoro-5'-(4,4,5,5-tetramethyl-[1,3,2]dioxaborolan-2-yl)biphenyl-2-carbonitrile as a white solid (1.3 g, 100%): $\delta_H$ (400 MHz, CDCl$_3$) 1.34 (12H, s), 7.21 (1H, dd, J 10 and 8), 7.45–7.52 (2H, m), 7.65 (1H, td, J 8 and 2), 7.74–7.78 (1H, m), 7.83 (1H, dd, J 8 and 2), 7.88 (1H, ddd, J 8, 5 and 2).

f) 2'-Fluoro-5'-(7-methyl-[1,8]naphthyridin-4-yl)biphenyl-2-carbonitrile

This compound was prepared as described in Example 1, step e), using 2'-fluoro-5'-(4,4,5,5-tetramethyl-[1,3,2]dioxaborolan-2-yl)biphenyl-2-carbonitrile instead of 3'-(4,4,5,5-tetramethyl-[1,3,2]dioxaborolan-2-yl)biphenyl-2-carbonitrile; the reaction was heated at 60° C. instead of being left at room temperature: $\delta_H$ (360 MHz, CDCl$_3$) 2.83 (3H, s), 7.40–7.42 (3H, m), 7.52–7.61 (4H, m), 7.70 (1H, m), 7.83 (1H, d, J 7.7), 8.32 (1H, d, J 8.8), 9.11 (1H, m); m/z (ES$^+$) 340 [MH]$^+$.

EXAMPLE 3

6.2'-Difluoro-5'-(7-trifluoromethyl[1,8]naphthyridin-4-yl)biphenyl-2-carbonitrile a) 2-[(6-Trifluoromethylpyridin-2-ylamino)methylene]malonic acid diethyl ester A mixture of 2-amino-6-trifluoromethylpyridine (15.0 g, 92.5 mmol) and diethyl ethoxymethylenemalonate (18.5 mL, 20.0 g, 92.5 mmol) in 1,4-dioxane (30 mL) was stirred at 100° C. for 48 h. Upon cooling to room temperature, 2-[(6-trifluoromethylpyridin-2-ylamino)methylene]malonic acid diethyl ester precipitated from solution, which was separated by filtration, washed with diethyl ether and air-dried (27.2 g, 89%): $\delta_H$ (400 MHz, CDCl$_3$) 1.35 (3H, t, J 7.2), 1.39 (3H, t, J 7.0), 4.28 (2H, q, J 7.2), 4.33 (2H, q, J 7.2), 7.03 (1H, d, J 8.2), 7.38 (1H, d, J 7.4), 7.82 (1H, t, J 8.1), 9.12 (1H, d, J 12.9), 11.20 (1H, d, J 12.5). m/z (ES$^+$) 333 [MH]$^+$, 287 [M-EtO]$^+$ b) 4-Hydroxy-7-trifluoromethyl[1,8]naphthyridine-3-carboxylic acid diethyl ester 2-[(6-Trifluoromethylpyridin-2-ylamino)methylene]malonic acid diethyl ester (25.0 g, 75.2 mmol) was added in portions to refluxing Dowtherm A (300 mL) and stirred at reflux for 2.5 h. The mixture was allowed to cool to room temperature, during which time an off-white solid precipitated from solution. The slurry was diluted with diethyl ether (250 mL), and the solid was separated by filtration, washed repeatedly with diethyl ether and dried. The off-white solid was 4-hydroxy-7-trifluoromethyl[1,8]naphthyridine-3-carboxylic acid diethyl ester (15.5 g, 72%). $\delta_H$ (360 MHz, d$_6$-DMSO) 1.29 (3H, t, J 7.1), 4.24 (2H, q, J 7.1), 7.93 (1H, d, J 8.1), 8.59 (1H, d, J 5.1), 8.78 (1H, d, J 8.1), 13.2 (1H, s).

c) 4-Hydroxy-7-trifluoromethyl[1,8]naphthyridine-3-carboxylic acid

A slurry of 4-hydroxy-7-trifluoromethyl[1,8]naphthyridine-3-carboxylic acid diethyl ester (15.5 g, 54.2 mmol) was stirred with potassium hydroxide (18.2 g, 0.325 mol) in water (155 mL) at reflux for 2 h. The resulting brown solution was cooled to room temperature and was diluted with water (300 mL) The pH was adjusted to ~7 by the addition of conc. hydrochloric acid, precipitating copious white solid, which was separated by filtration, and was dried at 60° C. over phosphorus pentoxide. This was 4-hydroxy-7-trifluoromethyl[1,8]-naphthyridine-3-carboxylic acid (14.0 g, 100%). $\delta_H$ (360 MHz, d$_6$-DMSO) 8.02 (1H, d, J 8.1), 8.91 (1H, s), 8.94 (1H, d, J 8.1). m/z (ES$^+$) 259 [MH]$^+$.

d) 7-Trifluoromethyl[1,8]naphthyridin-4-ol

4-Hydroxy-7-trifluoromethyl[1,8]-naphthyridine-3-carboxylic acid (14.0 g, 54.2 mmol) was added in portions to refluxing Dowtherm A (250 mL)—Care! Effervescence!—and the mixture was stirred at reflux for 80 min. The mixture was allowed to cool to room temperature, and a buff coloured solid precipitated from solution. The slurry was diluted with diethyl ether (250 mL) and the solid was separated by filtration, was washed with plenty of diethyl ether and was dried. This was 7-trifluoromethyl[1,8]naphthyridin-4-ol (11.6 g, 100%). $\delta_H$ (360 MHz, d$_6$-DMSO) 6.15 (1H, d, J 7.4), 7.76 (1H, d, J 8.1), 8.06 (1H, d, J 7.4), 8.70 (1H, d, J 8.1). m/z (ES$^+$) 215 [MH]$^+$.

e) 5-Chloro-2-trifluoromethyl[1,8]naphthyridine

7-Trifluoromethyl[1,8]naphthyridin-4-ol (2.00 g, 9.34 mmol) was added in portions to phosphorus oxychloride with stirring at room temperature—a mild exotherm was observed. The mixture was stirred at room temperature under nitrogen overnight. The solvent was removed in vacuo, and saturated sodium hydrogencarbonate solution was added with ice-bath cooling to the residual material with stirring, until the pH of the mixture was ~7. The mixture was extracted with dichloromethane (3×50 mL), then the combined organic layers were dried over magnesium sulfate, and were concentrated in vacuo. The crude product was purified by flash chromatography on silica gel, eluting with 25% ethyl acetate in dichloromethane, yielding 5-chloro-2-trifluoromethyl-[1,8]naphthyridine as an off-white solid (1.67 g, 77%). $\delta_H$ (360 MHz, CDCl$_3$) 7.72 (1H, d, J 4.6), 7.96 (1H, d, J 8.8), 8.86 (1H, d, J 8.4), 9.15 (1H, d, J 4.6). m/z (ES$^+$) 233, 235 [MH]$^+$.

f) 5'-(5,5-Dimethyl[1,3,2]dioxaborinan-2-yl)-6,2'-difluorobiphenyl-2-carbonitrile A mixture of 2,3-difluorobenzonitrile (19.0 g, 137 mmol) and ethanol (200 mL) pre-saturated with ammonia gas was heated at 140° C. in an autoclave for 8 h (terminal pressure 200 psi). The mixture was allowed to cool to ambient temperature and evaporated to dryness. The residue was dissolved in water (400 mL) and extracted with diethyl ether (2×300 mL). The combined organics were washed with water (300 mL) and brine (250 mL), dried over anhydrous magnesium sulfate, filtered and evaporated. Trituration with isohexane (150 mL) afforded 2-amino-3-fluorobenzonitrile (9.8 g, 50%) as an off-white solid: $\delta_H$ (360 MHz, CDCl$_3$) 4.47 (2H, s), 6.65–6.71 (1H, m), 7.14–7.20 (2H, m).

2-Amino-3-fluorobenzonitrile (9.8 g, 71.9 mmol) was dissolved in hot 1,4-dioxane (10 mL), 48% hydrobromic acid (100 mL) was added and the mixture cooled to 0° C. before dropwise addition of sodium nitrite (5.71 g, 82.7 mmol) in water (10 mL) over 1.5 h. The resulting mixture was stirred at 0° C. for 1.5 h then poured onto a cooled (0° C.) solution of copper(I) bromide (31.0 g, 216 mmol) in 48% hydrobromic acid (25 mL). The solution was stirred at 0° C. for 15 min then heated at 50° C. for 20 min. The mixture was cooled to ambient temperature, diluted with water (600 mL) and extracted with ethyl acetate (2×200 mL). The combined organics were washed with 10% aqueous ammonia solution (200 mL), water (200 mL) and brine (250 mL), dried over anhydrous magnesium sulfate, filtered and evaporated to give an orange oil. Purification by chromatography on silica gel eluting with isohexane on a gradient of ethyl acetate (2–4%) gave 2-bromo-3-fluorobenzonitrile (7.05 g, 49%) as a pale brown solid: $\delta_H$ (360 MHz, CDCl$_3$) 7.62–7.68 (1H, m), 7.74–7.85 (1H, ddd, J 9, 9 and 1), 7.74–7.85 (1H, ddd, J 8, 1 and 1).

A suspension of 2-bromo-3-fluorobenzonitrile (2.50 g, 12.5 mmol), potassium fluoride (2.40 g, 41.3 mmol) and 2-(2-fluoro-5-nitrophenyl)-4,4,5,5-tetramethyl-[1,3,2] dioxaborolane (4.67 g, 17.5 mmol) in tetrahydrofuran (50 mL) was degassed with nitrogen for 30 min. Tris(dibenzylideneacetone)dipalladium(0) and tri-tert-butylphosphine (0.2 M solution in 1,4-dioxane, 3.7 mL) were added and the mixture stirred at ambient temperature for 15 min then at 50° C. for 18 h. After cooling to ambient temperature, the resulting dark suspension was poured onto 0.5 M sodium hydroxide solution (500 mL) and stirred vigorously for 2 h. The dark solid was collected by filtration, washed with water (100 mL) and isohexane (50 mL) and left to air dry which gave 6,2'-difluoro-5'-nitro-biphenyl-2-carbonitrile as a brown/black solid (3.25 g, 100%): $\delta_H$ (400 MHz, CDCl$_3$) 7.40–7.44 (1H, m), 7.47–7.52 (1H, m), 7.59–7.67 (2H, m), 8.37–8.44 (2H, m).

6,2'-Difluoro-5'-nitrobiphenyl-2-carbonitrile (3.25 g, 12.5 mmol) in tetrahydrofuran (20 mL) and ethanol (20 mL) was treated with tin(II) chloride dihydrate (9.86 g, 43.8 mmol) and the mixture left to stir at ambient temperature for 18 h. The solvent was evaporated and the residue stirred with 2 N sodium hydroxide solution (40 mL) for 2 h. The resulting suspension was diluted with water (100 mL) and extracted with dichloromethane (3×200 mL). The combined organics were washed with water (200 mL), brine (200 mL), dried over anhydrous sodium sulfate, filtered and evaporated to give 5'-amino-6,2'-difluorobiphenyl-2-carbonitrile as a brown oil (2.87 9,100%): $\delta_H$ (360 MHz, CDCl$_3$) 3.74 (2H, s), 6.68 (1H, m), 6.73–6.77 (1H, m), 7.02 (1H, dd, J 9 and 9), 7.37–7.49 (2H, m), 7.56–7.65 (1H, m).

5'-Amino-3,2'-difluorobiphenyl-2-carbonitrile (2.87 g, 12.5 mmol) was dissolved in hot 1,4-dioxane (4 mL), 48% aqueous hydrobromic acid (40 mL) was added and the mixture cooled to 0° C. before dropwise addition of sodium nitrite (0.86 g, 12.5 mmol) in water (1.5 mL) over 20 min. The resulting mixture was stirred at 0° C. for 1.5 h then poured onto a cooled (0° C.) solution of copper(I) bromide (5.38 g, 37.5 mmol) in 48% hydrobromic acid (10 mL). The solution was stirred at 0° C. for 15 min then heated at 50° C. for 20 min. The mixture was cooled to ambient temperature, diluted with water (500 mL) and extracted with ethyl acetate (2×300 mL). The combined organics were washed with 10% aqueous ammonia solution (200 mL), water (200 mL) and brine (200 mL), dried over anhydrous magnesium sulfate, filtered and evaporated to give a black solid. Purification by chromatography on silica gel eluting with isohexane (containing 0.5% methanol) on a gradient of ethyl acetate (2–6%) gave 5'-bromo-6,2'-difluorobiphenyl-2-carbonitrile (2.28 g, 62%) as a yellow solid: $\delta_H$ (360 MHz, CDCl$_3$) 7.13 (1H, dd, J 9 and 9), 7.37–7.49 (2H, ddd, J 9, 9 and 1), 7.57–7.62 (4H, m).

A mixture of 5'-bromo-6,2'-difluorobiphenyl-2-carbonitrile (2.28 g, 7.75 mmol), potassium acetate (2.27 g, 23.3 mmol) and bis(neopentyl glycolato)diboron (2.56 g, 11.3 mmol) was dissolved in 1,4-dioxane containing 1% v/v dimethylsulfoxide (30 mL) and this solution was degassed with nitrogen for 5 min. Dichloro[1,1'-bis(diphenylphosphino)ferrocene]palladium(II) dichloromethane adduct (126 mg, 0.16 mmol) was then added and the mixture heated at 90° C. for 16 h. After cooling to ambient temperature the reaction was partitioned between ethyl acetate and water. The organic phase was washed with brine, dried over anhydrous magnesium sulfate, filtered and pre-adsorbed on to silica. Purification by chromatography on silica eluting with isohexane on a gradient of ethyl acetate (2–10%) gave a colourless oil that crystallised on standing to furnish 5'-(5,5-dimethyl[1,3,2]dioxaborinan-2-yl)-6,2'-difluorobiphenyl-2-carbonitrile as a pale brown solid (2.54 g, 100%): $\delta_H$ (360 MHz, CDCl$_3$) 1.02 (6H, s), 3.76 (4H, s), 7.21 (1H, dd, J 8.4 and 9.8), 7.37–7.50 (2H, m), 7.58 (1H, dd, J 1.1 and 7.0), 7.85 (1H, dd, J 1.4 and 8.1), 7.89–7.93 (1H, m).

g) 6,2-Difluoro-5'-(7-trifluoromethyl[1,8]naphthyridin-4-yl) biphenyl-2-carbonitrile A mixture of 5-chloro-2-trifluoromethyl-[1,8] naphthyridine (200 mg, 0.86 mmol), 5'-(5,5-dimethyl[1,3,2] dioxaborinan-2-yl)-6,2'-difluorobiphenyl-2-carbonitrile (366 mg, 1.12 mmol) and 2 M sodium carbonate solution (1.12 mL, 2.24 mmol) was stirred in DME (10 mL) and was degassed via three "freeze-thawn" cycles. Tetrakis (triphenylphosphine)palladium(0) (49.7 mg, 0.043 mmol) was added, the mixture was degassed as before, then was stirred at 80° C. under nitrogen for 24 h. The mixture was cooled to room temperature, was diluted with water (50 mL) and was washed with dichloromethane (3×50 mL). The combined organic layers were washed with saturated sodium chloride solution (1×50 mL), then were dried over magnesium sulfate and concentrated in vacuo. The crude product was purified by flash chromatography on silica gel, eluting with 10% to 20% ethyl acetate in dichloromethane, and yielding a pale yellow solid, which was recrystallised from 1:1 ethyl acetate:isohexane. 6,2-Difluoro-5'-(7-trifluoromethyl[1,8]naphthyridin-4-yl)biphenyl-2-carbonitrile was isolated as a colourless solid (178 mg, 50%). $\delta_H$ (360 MHz, CDCl$_3$) 7.48 (2H, t, J 8.8), 7.54–7.71 (5H, m), 7.88 (1H, d, J 8.8), 8.70 (1H, d, J 8.4), 9.29(1H, d, J 4.2). m/z (ES$^+$) 412 [MH]$^+$.

EXAMPLE 4

5-(4-Fluoro-3-pyridin-3-ylphenyl)-2-trifluoromethyl [1,8]naphthyridine a) 3-Bromo-4-fluorophenylamine 2-Bromo-1-fluoro-4-nitrobenzene was dissolved in tetrahydrofuran (75 mL) and ethanol (75 mL) and tin(II) chloride dihydrate added and the mixture left to stir at ambient temperature for 4 h. The solvent was evaporated and the residue was treated with ice-cold 2 N sodium hydroxide solution (200 mL). The resulting slurry was stirred for 30 min then extracted with dichloromethane (3×200 mL). The combined organic phase was washed with water (200 mL) and brine (200 mL), dried over anhydrous magnesium sulfate, filtered and evaporated to give 3-bromo-4-fluorophenylamine (7.92 g, 92%) as a yellow oil: $\delta_H$ (360 MHz, CDCl$_3$) 3.53 (2H, s), 6.53–6.57 (1H, m), 6.83–6.85 (1H, m), 6.90 (1H, dd, J 9 and 9).

b) 4-Fluoro-3-(pyridin-3-yl)phenylamine

A mixture of 3-bromo-4-fluorophenylamine (7.92 g, 41.7 mmol), diethyl(3-pyridyl)borane (6.74 g, 45.9 mmol), tetrakis(triphenylphosphine)palladium(0) (0.96 g, 0.83 mmol) and potassium carbonate (17.26 g, 125 mmol) in 1,2-dimethoxyethane (30 mL) and water (15 mL) was heated at 80° C. for 20 h. After cooling to ambient temperature the reaction was partitioned between ethyl acetate (500 mL) and water (500 mL). The organics were washed with brine (400 mL), dried over anhydrous sodium sulfate, filtered and concentrated in vacuo. Purification of the residue by flash chromatography on silica gel, eluting with dichloromethane on a gradient of ethyl acetate (0%–20%) gave 4-fluoro-3-(pyridin-3-yl)phenylamine (3.64 g, 46%) as a colourless oil that solidified on standing to afford a white solid: $\delta_H$ (360 MHz, CDCl$_3$) 3.65 (2H, s), 6.65–6.72 (2H, m), 6.99 (1H, dd, J 9 and 9), 7.33–7.37 (1H, m), 7.84–7.86 (1H, m), 8.58 (1H, d, J 4), 8.76 (1H, m).

c) 3-(5-Bromo-2-fluorophenyl)pyridine

A warm solution of 4-fluoro-3-(pyridin-3-yl)phenylamine (3.64 g, 19.3 mmol) in 1,4-dioxane (10 mL) was treated with a solution of 48% aqueous hydrobromic acid (100 mL). The resulting suspension was cooled to 0° C. before being treated dropwise over 20 min with a solution of sodium nitrite (1.53 g, 22.2 mmol) in water (4 mL). After stirring at 0° C. for 2 h, a cooled (0° C.) solution of copper(I) bromide (8.31 g, 57.9 mmol) in 48% aqueous hydrobromic acid (30 ml) was added to the reaction which was stirred at 0° C. for 10 min then heated at 50° C. for 20 min. The reaction was cooled to ambient temperature, poured onto ice-cold conc. ammonia (500 mL) and the product was extracted into ethyl acetate (500 mL). The organics were washed with water (300 mL) and brine (300 mL), dried over anhydrous sodium sulfate, filtered and concentrated in vacuo to give a dark oil. Purification by dry flash column chromatography on silica eluting with isohexane on a gradient of ethyl acetate (10%–30%) gave 3-(5-bromo-2-fluorophenyl)pyridine (3.1 g, 64%) as a white solid: $\delta_H$ (360 MHz, CDCl$_3$) 7.09 (1H, dd, J 9 and 1), 7.37–7.40 (1H, m), 7.46–7.51 (1H, m), 7.56–7.59 (1H, m), 7.83–7.86 (1H, m), 8.63–8.65 (1H, m), 8.77–8.79 (1H, m).

d) 3-[2-Fluoro-5-(4,4,5,5-tetramethyl-[1,3,2]dioxaborolan-2-yl)phenyl]pyridine 3-(5-Bromo-2-fluorophenyl)pyridine (3.1 g, 12.3 mmol), potassium acetate (3.62 g, 36.9 mmol) and bis(pinacolato) diboron (3.75 g, 14.8 mmol) were dissolved in 1,4-dioxane (40 mL) and dimethylsulfoxide (0.8 mL) and the mixture degassed with N$_2$ for 15 min. Dichloro[1,1'-bis(diphenylphosphino)ferrocene]palladium(II) dichloromethane adduct (300 mg, 0.37 mmol) was added and the mixture heated at 90° C. for 18 h. The mixture was cooled to ambient temperature and partitioned between diethyl ether (200 mL) and 2 N hydrochloric acid (50 mL). The organics were discarded and the aqueous phase adjusted to pH 8 by the addition of 4 N sodium hydroxide solution and extracted with diethyl ether (2×500 mL). The organic layer was washed with brine (50 mL), dried over anhydrous sodium sulfate, filtered and pre-adsorbed onto silica. Purification by flash column chromatography on silica eluting with 25% ethyl acetate in isohexane gave 3-[2-fluoro-5-(4,4,5,5-tetramethyl-[1,3,2]dioxaborolan-2-yl)phenyl]pyridine (2.64 g, 72%) as a yellow oil that crystallised on standing: $\delta_H$ (360 MHz, CDCl$_3$) 1.35 (12H, s), 7.20 (1H, dd, J 10 and 8), 7.35–7.39 (1H, m), 7.81–7.91 (3H, m), 8.61 (1H, dd, J 5 and 2), 8.82 (1H, s).

e) 5-(4-Fluoro-3-pyridin-3-ylphenyl)-2-trifluoromethyl[1,8]naphthyridine

5-Chloro-2-trifluoromethyl[1,8]naphthyridine (200 mg, 0.86 mmol) was coupled to 3-[2-fluoro-5-(4,4,5,5-tetramethyl-[1,3,2]dioxaborolan-2-yl)phenyl]pyridine (349 mg, 1.2 mmol) as described in Example 3 part g), affording 5-(4-fluoro-3-pyridin-3-ylphenyl)-2-trifluoromethyl[1,8] naphthyridine (90 mg, 28%). $\delta_H$ (360 MHz, CDCl$_3$) 7.41–7.46 (2H, m), 7.50–7.55 (1H, m), 7.57–7.61 (2H, m), 7.85 (1H, d, J 8.4), 7.91–7.96 (1H, m), 8.55 (1H, d, J 8.8), 8.68 (1H, dd, J 1.4 and 4.9), 8.86 (1H, s), 9.30 (1H, d, J 4.6). m/z (ES$^+$) 370 [MH]$^+$.

EXAMPLE 5

5-(4-Fluoro-3-pyridin-4-ylphenyl)-2-trifluoromethyl [1,8]naphthyridine a) 4-(2-Fluoro-5-nitrophenyl)pyridine To a degassed solution of 2-bromo-1-fluoro-4-nitrobenzene (6.44 g, 29.3 mmol), 4-tri-n-butylstannylpyridine (14.0 g, 38.0 mmol), lithium chloride (12.4 g, 293 mmol) and copper(I) iodide (0.56 g, 2.93 mmol) in N,N-dimethylacetamide (40 mL) was added tetrakis(triphenylphosphine)palladium(0) (1.69 g, 1.46 mmol) and the reaction heated at 80° C. for 18 h. After cooling to ambient temperature the solvent was evaporated and the residue was diluted with dichloromethane (800 mL) and the mixture stirred vigorously for 30 min then filtered. The organics were washed with water (500 mL) and brine (300 mL), dried over anhydrous magnesium sulfate, filtered and evaporated to give a black oil. The residue was purified by silica gel chromatography eluting with iso-hexane (containing 1% methanol and 1% triethylamine) on a gradient of ethyl acetate (20–50%) to give 4-(2-fluoro-5-nitrophenyl)pyridine as an off-white solid (5.60 g, 88%): $\delta_H$ (360 MHz, CDCl$_3$) 7.38 (1H, t, J 9), 7.50–7.53 (2H, m), 8.30–8.35 (1H, m), 8.41–8.44 (1H, m), 8.76–8.78 (2H, m).

b) 4-Fluoro-3-(pyridin-4-yl)phenylamine

To a solution of 4-(2-fluoro-5-nitrophenyl)pyridine (1.0 g, 5.58 mmol) in ethanol (30 mL) and ethyl acetate (10 mL) was added platinum(IV) oxide (52 mg) and the mixture stirred for 35 min under hydrogen (40 psi). The reaction was filtered through glass microfibre filter paper and the filtrate evaporated to dryness to give 4-fluoro-3-(pyridin-4-yl) phenylamine (862 mg, 100%) as a white solid: $\delta_H$ (360 MHz, CDCl$_3$) 3.49 (2H, s), 6.66–6.70 (1H, m), 6.71–6.76 (1H, m), 6.99 (1H, t, J 9), 7.44–7.46 (2H, m), 8.66 (2H, d, J 5).

c) 4-(5-Bromo-2-fluorophenyl)pyridine

4-Fluoro-3-(pyridin-4-yl)phenylamine (0.58 g, 3.08 mmol) was bromo-deaminated following the procedure given in Example 4 part c) to give 4-(5-bromo-2-fluorophenyl)pyridine (464 mg, 60%) as a white solid: $\delta_H$ (360 MHz, CDCl$_3$) 7.38 (1H, t, J 9), 7.59–7.62 (2H, m), 7.68–7.73 (1H, m), 7.84 (1H, dd, J 7 and 3), 8.68 (2H, d, J 5 and 3).

d) 4-Fluoro-3-(pyridin-4-yl)benzeneboronic acid and 4-[2-fluoro-5-(4,4,5,5-tetramethyl-[1,3,2]dioxaborolan-2-yl)phenyl]pyridine A mixture of 4-(5-bromo-2-fluorophenyl)pyridine (3.8 g, 15.1 mmol), potassium acetate (2.96 g, 30.1 mmol) and bis(pinacolato)diboron (4.21 g, 16.6 mmol) in 1,4-dioxane (50 mL) and dimethylsulfoxide (1 mL) was degassed with nitrogen for 1 h. Dichloro[1,1'-bis(diphenylphosphino)ferrocene]palladium(II) dichloromethane adduct (370 mg, 0.5 mmol) was added and the mixture heated at 90° C. for 18 h. The reaction was cooled to ambient temperature, filtered and the filter-cake washed with diethyl ether. The filtrate was evaporated to dryness and the residue stirred with ice-cold 2 N sodium hydroxide (100 mL) for 20 min. The aqueous mixture was filtered and the filtrate washed with diethyl ether (2×75 mL). The organics were discarded and the aqueous phase cooled to 0° C. before lowering the pH to 8 by addition of 36% hydrochloric acid. The resulting solid was collected by filtration and triturated with diethyl ether to afford 4-fluoro-3-(pyridin-4-yl)benzene-boronic acid as a buff-coloured solid (1.51 g, 46%): $\delta_H$ (360 MHz, DMSO) 7.34 (1H, dd, J 11 and 8), 7.61 (2H, d, J 5), 7.88–7.92 (1H, m), 8.05 (1H, dd, J 8 and 1), 8.26 (2H, s), 8.70 (2H, d, J 5); m/z (ES$^+$) 218 (M$^+$+H). The aqueous filtrate was extracted with diethyl ether. The organic phase was washed with water, brine, dried over anhydrous magnesium sulfate, filtered and evaporated to afford 4-[2-fluoro-5-(4,4,5,5-tetramethyl-[1,3,2]dioxaborolan-2-yl)phenyl]-pyridine as a dark oil (1.28 g, 29%) that solidified on standing for a few days: $\delta_H$ (360 MHz, CDCl$_3$) 1.36 (12H, s), 7.19 (1H, dd, J 11 and 8), 7.50–7.53 (2H, m), 7.82–7.87 (1H, m), 7.93 (1H, dd, J 8 and 1), 8.67 (2H, dd, J 4 and 1); m/z (ES$^+$) 300 (M$^+$+H).

e) 5-(4-Fluoro-3-pyridin-4-ylphenyl)-2-trifluoromethyl[1,8]naphthyridine

5-Chloro-2-trifluoromethyl[1,8]naphthyridine (100 mg, 0.43 mmol) was coupled to 4-fluoro-3-(pyridin-4-yl)benzeneboronic acid (121 mg, 0.56 mmol) as described in Example 3 part g), affording 5-(4-fluoro-3-pyridin-4-ylphenyl)-2-trifluoromethyl[1,8]naphthyridine (88 mg, 55%). $\delta_H$ (360 MHz, CDCl$_3$) 7.41–7.47 (1H, m), 7.52–7.63 (5H, m), 7.85 (1H, d, J 8.8), 8.52 (1H, d, J 8.4), 8.73–8.74 (2H, m), 9.30 (1H, d, J 4.2). m/z (ES$^+$) 370 [MH]$^+$.

EXAMPLE 6

5-[4-Fluoro-3-(3-fluoropyridin-2-yl)phenyl]-2-trifluoromethyl[1,8]naphthyridine a) 4-Fluoro-3-(3-fluoropyridin-2-yl)phenylboronic acid 2-Bromo-3-fluoropyridine, prepared according to the procedure of Queguiner et al. in *Tetrahedron*, 1983, 39, 2009–21, was coupled with 2-(2-fluoro-5-nitrophenyl)-4,4,5,5-tetramethyl-[1,3,2]dioxaborolane (as prepared in Example 2, part a)) by the method of Example 2, part b) to yield 3-fluoro-2-(2-fluoro-5-nitrophenyl)pyridine, which was transformed into 2-(5-bromo-2-fluorophenyl)-3-fluoropyridine by the method of Example 4, parts b) and c). This was converted into 4-fluoro-3-(3-fluoropyridin-2-yl)phenylboronic acid by the method of Example 5 part d), using bis(neopentyl glycolato)diboron instead of bis(pinacolato)diboron. $\delta_H$ (400 MHz, DMSO) 8.58 (1H, m), 8.19 (2H, s), 8.04 (1H, dd, J 8 and 2), 7.95 (1H, m), 7.86 (1H, m), 7.57 (1H, m), 7.31 (1H, dd, J 11 and 8).

b) 5-[4-Fluoro-3-(3-fluoropyridin-2-yl)phenyl]-2-trifluoromethyl[1,8]-naphthyridine 5-Chloro-2-trifluoromethyl[1,8]naphthyridine (100 mg, 0.43 mmol) was coupled to 4-fluoro-3-(3-fluoropyridin-2-yl)phenylboronic acid (131 mg, 0.56 mmol) as described in Example 3 part g), affording 5-[4-fluoro-3-(3-fluoropyridin-2-yl)phenyl]-2-trifluoromethyl[1,8]-naphthyridine (82 mg, 49%). $\delta_H$ (360 MHz, CDCl$_3$) 7.39–7.44 (2H, m), 7.55–7.63 (3H, m), 7.79 (1H, dd, J 2.3 and 6.5), 7.85 (1H, d, J 8.4), 8.55–8.60 (2H, m), 9.28 (1H, d, J 4.6). m/z (ES$^+$) 388 [MH]$^+$.

EXAMPLE 7

3,2'-Difluoro-5'-(7-trifluoromethyl-[1,8] naphthyridin-4-yl)biphenyl-2-carbonitrile a) 2-Amino-6-fluorobenzonitrile A mixture of 2,6-difluorobenzonitrile (19.0 g, 137 mmol) and ethanol (200 mL) pre-saturated with ammonia gas was heated at 140° C. in an autoclave for 6 h (terminal pressure 200 psi). The mixture was allowed to cool to ambient temperature, evaporated to dryness and triturated with water (200 mL). The solid was filtered and left to air dry to afford 2-amino-6-fluorobenzonitrile (18.0 g, 97%) as an off-white solid: $\delta_H$ (360 MHz, CDCl$_3$) 4.53 (3H, s), 6.44–6.52 (2H, m), 7.24–7.30 (1H, m).

b) 2-Bromo-6-fluorobenzonitrile

2-Amino-6-fluorobenzonitrile (18.0 g, 132 mmol) was dissolved in hot 1,4-dioxane (20 mL), 48% hydrobromic acid (200 mL) was added and the mixture cooled to 0° C. before dropwise addition of sodium nitrite (10.5 g, 152 mmol) in water (20 mL) over 1.5 h. The resulting mixture was stirred at 0° C. for 1.5 h then poured onto a cooled (0° C.) solution of copper(I) bromide (56.8 g, 396 mmol) in 48% hydrobromic acid (50 mL). The solution was stirred at 0° C. for 15 min then heated at 50° C. for 20 min. The mixture was cooled to ambient temperature, diluted with water (1200 mL) and extracted with ethyl acetate (2×400 mL). The combined organics were washed with 10% aqueous ammonia solution (400 mL), water (400 mL) and brine (500 mL), dried over anhydrous magnesium sulfate, filtered and evaporated to give an orange oil. Purification by chromatography on silica gel eluting with isohexane on a gradient of ethyl acetate (2–4%) gave 2-bromo-6-fluorobenzonitrile (18.5 g, 70%) as a white solid: $\delta_H$ (400 MHz, CDCl$_3$) 7.17–7.23 (1H, ddd, J 8, 8 and 1), 7.44–7.52 (2H, m).

c) 3,2'-Difluoro-5'-nitro-biphenyl-2-carbonitrile

A suspension of 2-bromo-6-fluorobenzonitrile (2.50 g, 12.5 mmol), potassium fluoride (2.40 g, 41.3 mmol) and 2-(2-fluoro-5-nitrophenyl)-4,4,5,5-tetramethyl-[1,3,2]dioxaborolane (4.67 g, 17.5 mmol) in tetrahydrofuran (50 mL) was degassed with nitrogen for 30 min. Tris(dibenzylideneacetone)dipalladium(0) and tri-tert-butylphosphine (0.2 M solution in 1,4-dioxane, 3.7 mL) were added and the mixture stirred at ambient temperature for 15 min then at 50° C. for 18 h. After cooling to ambient temperature, the resulting dark suspension was poured onto 0.5 M sodium hydroxide solution (500 mL) and stirred vigorously for 2 h. The dark solid was collected by filtration, washed with water (100 mL) and isohexane (50 mL) and left to air dry which gave 3,2'-difluoro-5'-nitro-biphenyl-2-carbonitrile as a brown/black solid (3.25 g, 100%): $\delta_H$ (360 MHz, CDCl$_3$) 7.32–7.44 (3H, m), 7.71–7.77 (1H, m), 8.35–8.41 (2H, m).

d) 5'-Amino-3,2'-difluorobiphenyl-2-carbonitrile 3,2'-Difluoro-5'-nitrobiphenyl-2-carbonitrile (3.25 g, 12.5 mmol) in tetrahydrofuran (20 mL) and ethanol (20 mL) was treated with tin(II) chloride dihydrate (9.86 g, 43.8 mmol)

and the mixture left to stir at ambient temperature for 18 h. The solvent was evaporated and the residue stirred with 2 N sodium hydroxide solution (40 mL) for 2 h. The resulting suspension was diluted with water (100 mL) and extracted with dichloromethane (3×200 mL). The combined organics were washed with water (200 mL), brine (200 mL), dried over anhydrous sodium sulfate, filtered and evaporated to give 5'-amino-3,2'-difluorobiphenyl-2-carbonitrile as a brown solid (2.87 9, 100%): $\delta_H$ (360 MHz, CDCl$_3$) 3.74 (2H, s), 6.66–6.75 (2H, m), 7.01 (1H, dd, J 9 and 9), 7.19–7.30 (2H, m), 7.59–7.65 (1H, m).

e) 5'-Bromo-3,2'-difluoro-biphenyl-2-carbonitrile

5'-Amino-3,2'-difluorobiphenyl-2-carbonitrile (2.87 g, 12.5 mmol) was dissolved in hot 1,4-dioxane (4 mL), 48% aqueous hydrobromic acid (40 mL) was added and the mixture cooled to 0° C. before dropwise addition of sodium nitrite (0.86 g, 12.5 mmol) in water (1.5 mL) over 20 min. The resulting mixture was stirred at 0° C. for 1.5 h then poured onto a cooled (0° C.) solution of copper(I) bromide (5.38 g, 37.5 mmol) in 48% hydrobromic acid (10 mL). The solution was stirred at 0° C. for 15 min then heated at 50° C. for 20 min. The mixture was cooled to ambient temperature, diluted with water (500 mL) and extracted with ethyl acetate (2×300 ml). The combined organics were washed with 10% aqueous ammonia solution (200 mL), water (200 mL) and brine (200 mL), dried over anhydrous magnesium sulfate, filtered and evaporated to give a black solid. Purification by chromatography on silica gel eluting with isohexane (containing 0.5% methanol) on a gradient of ethyl acetate (2–6%) gave 5'-bromo-3,2'-difluoro-biphenyl-2-carbonitrile (2.48 g, 68%) as a yellow solid: $\delta_H$ (400 MHz, CDCl$_3$) 7.13 (1H, dd, J 9 and 9), 7.27–7.30 (2H, m), 7.53–7.59 (2H, m), 7.64–7.69 (1H, m).

f) 5'-(5,5-Dimethyl-[1,3,2]dioxaborinan-2-yl)-3,2'-difluorobiphenyl-2-carbonitrile A mixture of 5'-bromo-3,2'-difluorobiphenyl-2-carbonitrile (2.48 g, 8.43 mmol), potassium acetate (2.48 g, 25.3 mmol) and bis(neopentyl glycolato)diboron (2.48 g, 11.0 mmol) in 1,4-dioxane (40 mL) containing dimethylsulfoxide (0.8 mL) was degassed with nitrogen for 20 min. Dichloro[1,1'-bis(diphenylphosphino)ferrocene]palladium (II) dichloromethane adduct (200 mg, 0.25 mmol) was then added and the reaction heated at 90° C. for 24 h. The mixture was cooled to ambient temperature then partitioned between 2 N sodium hydroxide (75 mL) and diethyl ether (100 mL) and the organics were discarded. The aqueous extract was made acidic (pH 5) with 36% hydrochloric acid and then extracted with diethyl ether (2×75 mL). The organic extract was washed with water (50 mL) and brine (75 mL), dried over anhydrous magnesium sulfate and evaporated to give 5'-(5,5-dimethyl-[1,3,2]dioxaborinan-2-yl)-3,2'-difluorobiphenyl-2-carbonitrile as a brown oil (2.5 g, 95%) that crystallised on standing: $\delta_H$ (360 MHz, CDCl$_3$) 1.03 (6H, s), 3.77 (4H, s), 7.17–7.25 (2H, m), 7.30 (1H, d, J 8), 7.59–7.65 (1H, m), 7.81–7.91 (2H, m).

g) 3,2'-Difluoro-5'-(7-trifluoromethyl-[1,8]naphthyridin-4-yl)biphenyl-2-carbonitrile 5-Chloro-2-trifluoromethyl[1,8]naphthyridine (50 mg, 0.22 mmol), 5'-(5,5-dimethyl-[1,3,2]dioxaborinan-2-yl)-3,2'-difluorobiphenyl-2-carbonitrile (91 mg, 0.28 mmol), tetrakis(triphenylphosphine)palladium(0) (5.0 mg, 2 mol %) and 2 M sodium carbonate solution (0.5 mL, 1.0 mmol) in DME (3 mL) was irradiated in a microwave reactor at 150° C. for 10 min. The mixture was cooled to room temperature and was diluted with water (3 mL) and dichloromethane (3 mL), and was then filtered through a PTFE cartridge. The separated organic phase was concentrated in vacuo, and the crude product was recrystallised from ethyl acetate, then again from ethyl acetate/isohexane, yielding 3,2'-difluoro-5'-(7-trifluoromethyl-[1,8]naphthyridin-4-yl)biphenyl-2-carbonitrile as an off-white solid (26 mg, 30%). $\delta_H$ (360 MHz, CDCl$_3$) 7.29–7.33 (1H, m), 7.41 (1H, d, J 7.4), 7.48 (1H, t, J 8.9), 7.58–7.61 (3H, m), 7.67–7.73 (1H, m), 7.89 (1H, d, J 8.8), 8.68 (1H, d, J 8.8), 9.29 (1H, dd, J 2.8 and 1.4). m/z (ES$^+$) 412 [MH]$^+$.

EXAMPLE 8

4,2'-Difluoro-5'-(7-trifluoromethyl-[1,8]naphthyridin-4-yl)biphenyl-2-carbonitrile a) 5'-(5,5-dimethyl-[1,3,2]dioxaborinan-2-yl)-4,2'-difluorobiphenyl-2-carbonitrile 2-Bromo-5-fluorobenzonitrile was coupled to 2-(2-fluoro-5-nitrophenyl)-4,4,5,5-tetramethyl-[1,3,2]dioxaborolane as described in Example 7 part c) to give 4,2'-difluoro-5'-nitrobiphenyl-2-carbonitrile as a black solid: $\delta_H$ (360 MHz, CDCl$_3$) 7.38–7.56 (4H, m), 8.33–8.40 (2H, m).

4,2'-Difluoro-5'-nitrobiphenyl-2-carbonitrile was reduced using the procedure described in Example 7 part d) to give 5'-amino-4,2'-difluorobiphenyl-2-carbonitrile: $\delta_H$ (360 MHz, CDCl$_3$) 3.66 (2H, s), 6.66–6.70 (1H, m), 6.71–6.74 (1H, m), 7.00 (1H, dd, J 9 and 9), 7.33–7.38 (1H, m), 7.44–7.49 (1H, m).

5'-Amino-4,2'-difluorobiphenyl-2-carbonitrile was bromo-deaminated using the procedure described in Example 7 part e) to give 5'-bromo-4,2'-difluorobiphenyl-2-carbonitrile as a pale brown solid: $\delta_H$ (360 MHz, CDCl$_3$) 7.11 (1H, dd, J 9 and 9), 7.37–7.58 (5H, m).

5'-Bromo-4,2'-difluorobiphenyl-2-carbonitrile was converted to 5'-(5,5-dimethyl[1,3,2]dioxaborinan-2-yl)-4,2'-difluorobiphenyl-2-carbonitrile using the procedure described in Example 7 part f). This produced a brown oil that crystallised on standing: $\delta_H$ (360 MHz, CDCl$_3$) 1.03 (6H, s), 3.76 (4H, s), 7.20 (1H, dd, J 10 and 8), 7.33–7.38 (1H, m), 7.44–7.50 (2H, m), 7.81 (1H, dd, J 8 and 2), 7.85–7.90 (1H, m).

b) 4,2'-Difluoro-5'-(7-trifluoromethyl[1,8]naphthyridin-4-yl)biphenyl-2-carbonitrile 5-Chloro-2-trifluoromethyl[1,8]naphthyridine (50 mg, 0.22 mmol) was coupled to 5'-(5,5-dimethyl-[1,3,2]dioxaborinan-2-yl)-4,2'-difluorobiphenyl-2-carbonitrile (77 mg, 0.24 mmol) as described in Example 7 part g), affording 4,2'-difluoro-5'-(7-trifluoromethyl-[1,8]naphthyridin-4-yl)biphenyl-2-carbonitrile (13 mg, 14%). $\delta_H$ (400 MHz, CDCl$_3$) 7.41–7.49 (2H, m), 7.54–7.63 (5H, m), 7.88 (1H, d, J 9.0), 8.68 (1H, d, J 8.2), 9.29 (1H, d, J 4.3). m/z (ES$^+$) 412 [MH]$^+$.

EXAMPLE 9

5,2'-Difluoro-5'-(7-trifluoromethyl-[1,8]naphthyridin-4-yl)biphenyl-2-carbonitrile a) 5'-(5,5-dimethyl-[1,3,2]dioxaborinan-2-yl)-5,2'-difluorobiphenyl-2-carbonitrile 2-Bromo-4-fluorobenzonitrile was coupled to 2-(2-fluoro-5-nitrophenyl)-4,4,5,5-tetramethyl-[1,3,2]dioxaborolane as described in Example 7 part c) to give 5,2'-difluoro-5'-nitrobiphenyl-2-carbonitrile as a black solid: $\delta_H$ (360 MHz, CDCl$_3$) 7.25–7.33 (2H, m), 7.40–7.44 (1H, m), 7.86 (1H, dd, J 9 and 6), 8.35–8.42 (2H, m).

5,2'-Difluoro-5'-nitrobiphenyl-2-carbonitrile was reduced using the protocol described in Example 7 part d) to give 5'-amino-5,2'-difluorobiphenyl-2-carbonitrile: $\delta_H$ (360 MHz, CDCl$_3$) 3.68 (2H, s), 6.67–6.76 (2H, m), 7.02 (1H, dd, J 9 and 9), 7.12–7.27 (2H, m), 7.78 (1H, dd, J 9 and 6).

5'-Amino-5,2'-difluorobiphenyl-2-carbonitrile was bromo-deaminated as described in Example 7 part e) to give 5'-bromo-5,2'-difluoro-biphenyl-2-carbonitrile as a pale brown solid: $\delta_H$ (400 MHz, CDCl$_3$) 7.13 (1H, dd, J 9 and 9), 7.19–7.23 (2H, m), 7.52–7.60 (2H, m), 7.81 (1H, dd, J 8 and 5).

5'-Bromo-5,2'-difluorobiphenyl-2-carbonitrile was converted to 5'-(5,5-dimethyl-[1,3,2]dioxaborinan-2-yl)-5,2'-difluorobiphenyl-2-carbonitrile as described in Example 7 part f). This produced a brown oil that crystallised on standing: $\delta_H$ (400 MHz, CDCl$_3$) 1.03 (6H, s), 3.77 (4H, s), 7.15–7.24 (3H, m), 7.77 (1H, dd, J 9 and 6), 7.83 (1H, dd, J 8 and 2), 7.87–7.91 (1H, m).

b) 5,2'-Difluoro-5'-(7-trifluoromethyl-[1,8]naphthyridin-4-yl)biphenyl-2-carbonitrile 5-Chloro-2-trifluoromethyl[1,8]naphthyridine (50 mg, 0.22 mmol) was coupled to 5'-(5,5-dimethyl-[1,3,2]dioxaborinan-2-yl)-5,2'-difluorobiphenyl-2-carbonitrile (91 mg, 0.28 mmol) as described in Example 7 part g), affording 5,2'-difluoro-5'-(7-trifluoromethyl-[1,8]naphthyridin-4-yl)biphenyl-2-carbonitrile (27 mg, 30%). $\delta_H$ (360 MHz, CDCl$_3$) 7.24–7.29 (1H, m), 7.34 (1H, dt, J 7.2 and 1.9), 7.46–7.51 (1H, m), 7.59–7.65 (3H, m), 7.84–7.90 (2H, m), 8.68 (1H, d, J 8.8), 9.29 (1H, d, J 4.2). m/z (ES$^+$) 412 [MH]$^+$.

EXAMPLE 10

4-Fluoro-3'-(7-trifluoromethyl[1,8]naphthyridin-4-yl)biphenyl-2-carbonitrile a) 4-Fluoro-3'-(4,4,5,5-tetramethyl-[1,3,2]dioxaborolan-2-yl)biphenyl-2-carbonitrile 2-Bromo-5-fluorobenzonitrile was coupled with 3-nitrophenylboronic acid by the method of Example 7, part c) to yield 4-fluoro-3'-nitrobiphenyl-2-carbonitrile, which was reduced to 3'-amino-4-fluorobiphenyl-2-carbonitrile by the method of Example 5, part b). This was converted into 4-fluoro-3'-(4,4,5,5-tetramethyl-[1,3,2]dioxaborolan-2-yl)biphenyl-2-carbonitrile as described in Example 7 parts e) and f), using bis(pinacolato)diboron instead of bis(neopentyl glycolato)diboron. The product was isolated as a brown oil which solidified on standing. $\delta_H$ (400 MHz, CDCl$_3$) 1.36 (12H, s), 7.35 (1H, td, J 8.2 and 2.7), 7.44–7.54 (3H, m), 7.65 (1H, dt, J 8.2 and 1.7), 7.88–7.90 (2H, m)

b) 4-Fluoro-3'-(7-trifluoromethyl[1,8]naphthyridin-4-yl)biphenyl-2-carbonitrile

5-Chloro-2-trifluoromethyl[1,8]naphthyridine (50 mg, 0.22 mmol) was coupled to 4-fluoro-3'-(4,4,5,5-tetramethyl-[1,3,2]dioxaborolan-2-yl)biphenyl-2-carbonitrile (91 mg, 0.28 mmol) as described in Example 7 part g), affording 4-fluoro-3'-(7-trifluoromethyl[1,8]naphthyridin-4-yl)biphenyl-2-carbonitrile (22 mg, 26%). $\delta_H$ (360 MHz, CDCl$_3$) 7.39–7.45 (1H, m), 7.51–7.76 (7H, m), 7.87 (1H, d, J 8.4), 8.71 (1H, d, J 8.4), 9.29 (1H, d, J 4.6). m/z (ES$^+$) 394 [MH]$^+$.

EXAMPLE 11

5-(2-Fluoro-3-pyridin-2-ylphenyl)-2-trifluoromethyl-[1,8]naphthyridine a) 2-(2-Fluorophenyl)pyridine A mixture of 2-bromopyridine (6.37 g, 35 mmol), 2-fluorobenzeneboronic acid (6.86 g, 49 mmol) and 2 M sodium carbonate solution (35 mL, 70 mmol) in THF (70 mL) was degassed with nitrogen for 20 min. Tetrakis(triphenyl-phosphine)palladium(0) (1.21 g, 1.1 mmol) was added, and the mixture was stirred at reflux under nitrogen for 36 h. After cooling to room temperature, the mixture was partitioned between ethyl acetate and sodium carbonate. The organic phase was washed with water and then with saturated sodium hydrogencarbonate solution, was dried over magnesium sulfate and then was absorbed on to silica gel. Purification by flash chromatography on silica gel, eluting with isohexane (+0.5% triethylamine and 0.5% MeOH) on a gradient of diethyl ether (5% to 20%) afforded 2-(2-fluorophenyl)pyridine as a yellow oil which crystallised upon standing (5.5 g, 91%). $\delta_H$ (400 MHz, CDCl$_3$) 7.13–7.19 (1H, m), 7.24–7.28 (2H, m), 7.35–7.41 (1H, m), 7.73–7.81 (2H, m), 7.97 (1H, ddd, J 8, 8 and 2), 8.72–8.74 (1H, m); m/z (ES$^+$) 174 (M$^+$+H).

b) 2-Fluoro-3-(pyridin-2-yl)benzeneboronic acid 2,2,6,6-Tetramethylpiperidine (8.61 mL, 7.23 g, 51.2 mmol) was added dropwise with stirring to a mixture of 2.5 M solution of n-butyllithium in hexanes (19.6 mL, 49 mmol) and THF (130 mL) at −78° C. 2-(2-Fluoro-phenyl)pyridine (8.06 g, 46.5 mmol) in THF (25 mL) was added dropwise with stirring to the resulting solution at −78° C., and the mixture was stirred at the same temperature for 2 h. Trimethyl borate (10.5 mL, 9.67 g, 93 mmol) was added at −78° C., and the mixture was stirred for a further 10 min before being allowed to warm to room temperature. 2 N Hydrochloric acid (12 mL) was added, then the mixture was stirred for 30 min at room temperature, and was concentrated in vacuo. The residual material was stirred with 2 N hydrochloric acid (130 mL) for 1 h. The mixture was adjusted to pH 14 by addition of 2 N sodium hydroxide solution, and was then washed with diethyl ether. Concentrated hydrochloric acid was added to the aqueous phase with ice-bath cooling, until the pH was ~8, precipitating a white solid. The slurry was stirred at 0° C. for 1 h, and was then filtered, yielding the residual boronic acid as a sticky white solid. This was refluxed in diethyl ether overnight, and was then filtered, affording 2-fluoro-3-(pyridin-2-yl)benzeneboronic acid as a white powder (3.4 g, 34%). m/z (ES$^+$) 218 (M$^+$+H).

c) 5-(2-Fluoro-3-pyridin-2-ylphenyl)-2-trifluoromethyl-[1,8]naphthyridine

5-Chloro-2-trifluoromethyl[1,8]naphthyridine (50 mg, 0.22 mmol) was coupled to 2-fluoro-3-(pyridin-2-yl)benzeneboronic acid (61 mg, 0.28 mmol) as described in Example 7 part g), affording 5-(2-fluoro-3-pyridin-2-ylphenyl)-2-trifluoromethyl[1,8]naphthyridine (17 mg, 21%). $\delta_H$ (360 MHz, CDCl$_3$) 7.30–7.36 (1H, m), 7.42–7.55 (2H, m), 7.66 (1H, d, J 4.2), 7.77–7.83 (3H, m), 8.19 (1H, td, J 7.6 and 2.1), 8.38 (1H, dd, J 2.3 and 8.6), 8.78 (1H, dt, J 4.9 and 1.4), 9.33 (1H, d, J 4.2). m/z (ES$^+$) 370 [MH]$^+$.

EXAMPLE 12

5-(2-Fluoro-3-pyridin-3-ylphenyl)-2-trifluoromethyl-[1,8]naphthyridine a) 2-Fluoro-3-(pyridin-3-yl)benzeneboronic acid A mixture of 3-bromopyridine (3.37 mL, 5.53 g, 35 mmol), 2-fluorobenzeneboronic acid (6.12 g, 43.8 mmol) and potassium fluoride (6.71 g, 116 mmol) in THF (50 mL) was degassed with nitrogen for 10 min. Tris(dibenzylideneacetone)dipalladium(0) (0.64 g, 0.70 mmol) and tri(tert-butyl)phosphine (7 mL of a 0.2 M solution in dioxane, 1.4 mmol) were added. A solid precipitated, giving a thick slurry which was stirred under nitrogen for 15 min, then at 50° C. for 30 min. After cooling to room temperature, the mixture was partitioned between ethyl acetate and water. The organic phase was washed with saturated sodium chloride solution, then was dried over magnesium sulfate and pre-adsorbed on to silica gel. Purification by flash chromatography on silica gel eluting with isohexane (+0.5% methanol +0.5% triethylamine) on a gradient of 20% to 40% ethyl acetate afforded 3-(2-fluorophenyl)pyridine as a pale yellow oil, which crystallised upon standing. δ$_H$(360 MHz, DMSO) 7.33–7.40 (2H, m), 7.46–7.55 (2H, m), 7.61 (1H, ddd, J 8, 8 and 2), 7.96–8.01 (1H, m), 8.61 (1H, dd, J 5 and 2), 8.77 (1H, s).

b) 2-Fluoro-3-(pyridin-3-yl)benzeneboronic acid 3-(2-Fluorophenyl)pyridine was lithiated and reacted with trimethyl borate as described in Example 11 to give 2-fluoro-3-(pyridin-3-yl)benzeneboronic acid as a white solid: m/z (ES$^+$) 218 (M$^+$+H).

c) 5-(2-Fluoro-3-pyridin-3-ylphenyl)-2-trifluoromethyl-[1,8]naphthyridine

5-Chloro-2-trifluoromethyl[1,8]naphthyridine (50 mg, 0.22 mmol) was coupled to 2-fluoro-3-(pyridin-3-yl)benzeneboronic acid (61 mg, 0.28 mmol) as described in Example 7 part g), affording 5-(2-fluoro-3-pyridin-3-ylphenyl)-2-trifluoromethyl[1,8]naphthyridine (36 mg, 45%). δ$_H$ (360 MHz, CDCl$_3$) 7.40–7.55 (3H, m), 7.65–7.70 (2H, m), 7.84 (1H, d, J 8.4), 7.93 (1H, dq, J 8.1 and 1.9), 8.37 (1H, dd, J 2.3 and 8.6), 8.67 (1H, dd, J 1.6 and 4.7), 8.86 (1H, s), 9.34 (1H, d, J 4.6). m/z (ES$^+$) 370 [MH]$^+$.

EXAMPLE 13

5-(2-Fluoro-3-pyridin-4-ylphenyl)-2-trifluoromethyl-[1,8]naphthyridine a) 2-Fluoro-3-(pyridin-4-yl)benzeneboronic acid A mixture of 4-bromopyridine hydrochloride (7.5 g, 38.6 mmol) and 2-fluorobenzeneboronic acid (6.75 g, 48 mmol) in tetrahydrofuran (80 mL) and 2 M sodium carbonate (58 mL) was degassed with nitrogen for 20 min then tetrakis(triphenylphosphine)palladium(0) (1.34 g, 1.2 mmol) was added and the reaction heated at reflux for 24 h. The mixture was cooled to ambient temperature then partitioned between ethyl acetate and 10% sodium carbonate. The organics were washed with water and saturated sodium hydrogencarbonate, dried over anhydrous magnesium sulfate, filtered and pre-adsorbed onto silica. Purification by chromatography on silica eluting with isohexane (containing 0.5% triethylamine) on a gradient of ethyl acetate (20–40%) afforded 4-(2-fluorophenyl)pyridine as a yellow oil that crystallised on standing (6.26 g, 94%): δ$_H$ (400 MHz, CDCl$_3$) 7.17–7.22 (1H, m), 7.26 (1H, ddd, J 8, 8 and 1), 7.38–7.44 (1H, m), 7.47–7.50 (3H, m), 8.68 (2H, d, J 4); m/z (ES$^+$) 174 (M$^+$+H).

4-(2-Fluorophenyl)pyridine was lithiated and reacted with trimethyl borate as described in Example 11 to afford 2-fluoro-3-(pyridin-4-yl)benzeneboronic acid as a white solid: m/z (ES$^+$) 218 (M$^+$+H).

b) 5-(2-Fluoro-3-pyridin-4-ylphenyl)-2-trifluoromethyl[1,8]naphthyridine

5-Chloro-2-trifluoromethyl[1,8]naphthyridine (50 mg, 0.22 mmol) was coupled to 2-fluoro-3-(pyridin-4-yl)benzeneboronic acid (61 mg, 0.28 mmol) as described in Example 7 part g), affording 5-(2-fluoro-3-pyridin-4-ylphenyl)-2-trifluoromethyl[1,8]naphthyridine (37 mg, 47%). δ$_H$ (360 MHz, CDCl$_3$) 7.45–7.54 (4H, m), 7.65 (1H, d, J 4.2), 7.68–7.74 (1H, m), 7.84 (1H, d, J 8.4), 8.35 (1H, dd, J 2.5 and 8.8), 8.72–8.74 (2H, m), 9.34 (1H, d, J 4.2). m/z (ES$^+$) 370 [MH]$^+$.

EXAMPLE 14

5-(2,4-Difluoro-3-pyridin-3-ylphenyl)-2-trifluoromethyl[1,8]naphthyridine a) 2,4-Difluoro-3-(pyridin-3-yl)phenylamine A mixture of 3-bromo-2,4-difluorophenylamine (prepared according to the procedure described in EP-A-0184384) (12.5 g, 60 mmol), diethyl(3-pyridyl)borane (10.6 g, 72 mmol) and potassium carbonate (16.6 g, 120 mmol) in tetrahydrofuran (150 mL) and water (50 mL) was degassed with nitrogen for 15 min. To this mixture was added tetrakis(triphenylphosphine)palladium(0) (2.1 g, 1.8 mmol) and the reaction was heated at reflux for 4 days. The mixture was cooled to ambient temperature and the majority of the tetrahydrofuran removed on a rotary evaporator. The residue was diluted with water (250 mL), extracted with ethyl acetate (300 mL), the organics were washed with water, brine, dried over anhydrous magnesium sulfate, filtered and pre-adsorbed onto silica. Purification by chromatography on silica gel eluting with isohexane (containing 1% triethylamine) on a gradient of ethyl acetate (10–50%) afforded 2,4-difluoro-3-(pyridin-3-yl)phenylamine as a cream-coloured solid (5.8 g, 7%): δ$_H$ (400 MHz, CDCl$_3$) 3.69 (2H, br), 6.72–6.88 (2H, m), 7.39 (1H, dd, J 8 and 5), 7.80 (1H, d, J 8), 8.62 (1H, dd, J 5 and 1), 8.72 (1H, s).

b) 3-(3-Bromo-2,6-difluorophenyl)pyridine 2,4-Difluoro-3-(pyridin-3-yl)phenylamine was bromodeaminated as described in example 4 part c) to afford 3-(3-bromo-2,6-difluorophenyl)pyridine as a white solid: δ$_H$ (400 MHz, CDCl$_3$) 6.97 (1H, ddd, J 9, 9 and 2), 7.40–7.44 (1H, m), 7.55–7.60 (1H, m), 7.77–7.81 (1H, m), 8.66 (1H, dd, J 5 and 2), 8.71 (1H, s).

c) 2,4-Difluoro-3-(pyridin-3-yl)benzeneboronic acid

A mixture of 3-(3-bromo-2,6-difluorophenyl)pyridine (2.97 g, 11 mmol), potassium acetate (2.16 g, 22 mmol) and bis(neopentyl glycolato)diboron (2.86 g, 12.7 mmol) in 1,4-dioxane (30 mL) was heated at 90° C. for 16 h. The reaction was cooled, filtered (washing the filter cake with a small quantity of diethyl ether) and the filtrate concentrated in vacuo. The residue was partitioned between diethyl ether (100 mL) and 1 M sodium hydroxide (100 mL) and the organics discarded. The aqueous was washed with more diethyl ether and then cooled in an ice-water bath. The pH was adjusted to approximately 6 with 36% hydrochloric acid, and allowed to stand for 1 h. The resulting solid was collected by filtration and dried under vacuum to afford 2,4-difluoro-3-(pyridin-3-yl)benzeneboronic acid (2.2 g, 85%) as a grey solid: m/z (ES$^+$) 236 (M$^+$+H).

d) 5-(2,4-Difluoro-3-pyridin-3-ylphenyl)-2-trifluoromethyl[1,8]naphthyridine

5-Chloro-2-trifluoromethyl[1,8]naphthyridine (50 mg, 0.22 mmol) was coupled to 2,4-difluoro-3-(pyridin-3-yl)benzeneboronic acid (66 mg, 0.28 mmol) as described in Example 7 part g), affording 5-(2,4-difluoro-3-pyridin-3-ylphenyl)-2-trifluoromethyl[1,8]naphthyridine (27 mg, 34%). δ$_H$ (360 MHz, CDCl$_3$) 7.28 (1H, m), 7.42–7.49 (2H, m), 7.63 (1H, d, J 4.6), 7.84–7.88 (2H, m), 8.35 (1H, dd, J 2.3 and 8.6), 8.69 (1H, dd, J 1.8 and 4.9), 8.80 (1H, s), 9.33 (1H, d, J 4.2). m/z (ES$^+$) 388 [MH]$^+$.

EXAMPLE 15

5-(2,4-Difluoro-3-pyridin-4-ylphenyl)-2-trifluoromethyl[1,8]naphthyridine a) 4-(2,6-Difluorophenyl)pyridine A suspension of 4-bromopyridine hydrochloride (6.81 g, 35 mmol) in tetrahydrofuran (100 mL) was treated with sodium hydroxide (8.75 mL of a 4 N solution in water) and this mixture was stirred at ambient temperature for 5 min. 2,6-Difluorobenzeneboronic acid (6.36 g, 40 mmol) and potassium fluoride (6.71 g, 116 mmol) were added and this mixture was degassed with nitrogen for 10 min before adding tris(dibenzylideneacetone)dipalladium(0) (640 mg, 0.7 mmol) followed by tri-tert-butylphosphine (7 mL of a 0.2 M solution in 1,4-dioxane, 1.4 mmol). This mixture was stirred at ambient temperature for 15 min then heated at 50°

C. for 30 min. The reaction mixture was diluted with dichloromethane then extracted with ice-cold 1 N sodium hydroxide solution (×2). The organics were dried over anhydrous magnesium sulfate, filtered and pre-adsorbed onto silica. Purification by chromatography on silica eluting with isohexane (containing 0.5% methanol and 0.5% triethylamine) on a gradient of ethyl acetate (20–30%) gave 4-(2,6-difluorophenyl)pyridine as a white solid (3.2 g, 48%): $\delta_H$ (400 MHz, CDCl$_3$) 6.99–7.06 (2H, m), 7.32–7.39 (1H, m), 7.40–7.42 (2H, m), 8.71 (2H, d, J 6).

b) 2,4-Difluoro-3-(pyridin-4-yl)benzeneboronic acid 4-(2,6-Difluorophenyl)pyridine was converted to 2,4-difluoro-3-(pyridin-4-yl)benzeneboronic acid using the procedure described in Example 11 part b). m/z (ES$^+$) 235 (M$^+$+H).

c) 5-(2,4-Difluoro-3-pyridin-4-ylphenyl)-2-trifluoromethyl[1,8]naphthyridine

5-Chloro-2-trifluoromethyl[1,8]naphthyridine (50 mg, 0.22 mmol) was coupled to 2,4-difluoro-3-(pyridin-4-yl)benzeneboronic acid (66 mg, 0.28 mmol) as described in Example 7 part g), affording 5-(2,4-difluoro-3-pyridin-4-ylphenyl)-2-trifluoromethyl-[1,8]naphthyridine (30 mg, 36%). $\delta_H$ (360 MHz, CDCl$_3$) 7.29 (1H, m), 7.41–7.50 (3H, m), 7.62 (1H, d, J 4.6), 7.85 (1H, d, J 8.8), 8.33 (1H, dd, J 2.3 and 8.6), 8.75–8.77 (2H, m), 9.34 (1H, d, J 4.6). m/z (ES$^+$) 388 [MH]$^+$.

EXAMPLE 16

3'-Fluoro-5'-(7-trifluoromethyl-[1,8]naphthyridin-4-yl)biphenyl-2-carbonitrile a) 2-Bromo-4-fluoro-6-nitrophenylamine A solution of 4-fluoro-2-nitroaniline (39.03 g, 250 mmol) in water (900 mL) and 48% hydrobromic acid (1500 mL) was treated with bromine (15.26 mL, 46 g, 288 mmol) added dropwise over 20 min. The resulting precipitate was stirred at ambient temperature for a further 45 min then diluted with ice-water (2000 mL). The solid product was collected by filtration, washed with cold water and dried to afford 2-bromo-4-fluoro-6-nitrophenylamine as an orange powder (55 g, 94%): $\delta_H$ (360 MHz, CDCl$_3$) 6.49 (2H, br), 7.56 (1H, dd, J 7 and 3), 7.90 (1H, dd, J 9 and 3).

b) 1-Bromo-3-fluoro-5-nitrobenzene

A mixture of 2-bromo-4-fluoro-6-nitrophenylamine (55 g, 234 mmol) in 50% sulphuric acid (500 mL) was cooled to 0° C. then treated dropwise with a solution of sodium nitrite (22.6 g, 328 mmol) in water (100 mL) keeping the internal temperature <5° C. Following the addition of the sodium nitrite the reaction was stirred at <5° C. for 1 h. Ethanol (75 mL) was then added followed by ferrous sulfate heptahydrate (32.5 g, 117 mmol) and the reaction stirred at ambient temperature for 2 h. The reaction was diluted with water (1 L) and extracted with dichloromethane (2×500 mL). The organics were combined, washed with saturated aqueous sodium hydrogencarbonate, water and brine, then dried for 1 h over anhydrous magnesium sulfate containing decolorizing charcoal (5 g). Filtration through glass micro-fibre filter paper (Whatman GF/A) and evaporation to dryness gave an oil which on standing furnished 1-bromo-3-fluoro-5-nitrobenzene as colourless crystals (50 g, 97%): $\delta_H$ (360 MHz, CDCl$_3$) 7.61 (1H, ddd, J 8, 2 and 2), 7.90 (1H, ddd, J 8, 2 and 2), 8.20–8.23 (1H, m).

c) 2-(3-Fluoro-5-nitrophenyl)-5,5-dimethyl-[1,3,2]dioxaborinane

A mixture of 1-bromo-3-fluoro-5-nitrobenzene (17.6 g, 80 mmol), potassium acetate (15.7 g, 160 mmol) and bis(neopentyl glycolato)diboron in 1,4-dioxane (200 mL) was degassed with nitrogen for 30 min before adding dichloro[1,1'-bis(diphenylphosphino)ferrocene]palladium(II) dichloromethane adduct (1.96 g, 2.4 mmol). The reaction was heated at 90° C. for 16 h, cooled to ambient temperature, filtered (washing the filter cake with a small quantity of dichloromethane) and the filtrate concentrated in vacuo. The residue was partitioned between diethyl ether (300 mL) and 2 M sodium hydroxide (300 mL) and the organics discarded. The aqueous was washed with more ether and then cooled in an ice-water bath. The pH was adjusted to approximately 6 with 36% hydrochloric acid and allowed to stand overnight. The resulting solid was collected by filtration, washed with ice-cold water and dried under vacuum over phosphorus pentoxide to furnish 2-(3-fluoro-5-nitrophenyl)-5,5-dimethyl[1,3,2]dioxaborinane as a buff-coloured solid (15 g, 74%): $\delta_H$ (400 MHz, DMSO) 0.97 (6H, s), 3.81 (4H, s), 7.81 (1H, dd, J 8 and 2), 8.17 (1H, ddd, J 8, 2 and 2), 8.67 (1H, s).

d) 3'-Fluoro-5'-nitrobiphenyl-2-carbonitrile

A mixture of 2-(3-fluoro-5-nitrophenyl)-5,5-dimethyl-[1,3,2]dioxaborinane (15 g, 59 mmol) and 2-bromobenzonitrile (12.4 g, 68.2 mmol) in 1,2-dimethoxyethane (125 mL) and 2 M aqueous sodium carbonate (50 mL) was degassed with nitrogen for 30 min then treated with tetrakis-(triphenylphosphine)palladium(0) (2.06 g, 1.8 mmol). The reaction was then heated at 90° C. for 16 h, cooled to ambient temperature and partitioned between ethyl acetate and water. The organics were washed with brine, dried over anhydrous magnesium sulfate, filtered and pre-adsorbed onto silica gel. Purification by dry flash chromatography on silica gel, eluting with isohexane (containing 1% methanol) on a gradient of ethyl acetate (10–40%) afforded 3'-fluoro-5'-nitrobiphenyl-2-carbonitrile as a cream-coloured solid (10.3 g, 72%): $\delta_H$ (400 MHz, CDCl$_3$) 7.54–7.61 (2H, m), 7.65 (1H, ddd, J 8, 2 and 2), 7.74 (1H, ddd, J 8, 8 and 2), 7.84 (1H, dd, J 8 and 2), 8.03 (1H, ddd, J 8, 8 and 2), 8.22–8.24 (1H, m).

e) 5'-Amino-3'-fluorobiphenyl-2-carbonitrile

A cooled (0° C.) suspension of 3'-fluoro-5'-nitrobiphenyl-2-carbonitrile (8.9 g, 37 mmol) in ethanol (70 mL) and tetrahydrofuran (70 mL) was treated with tin(II) chloride dihydrate (29 g, 129 mmol) and the mixture was stirred at ambient temperature for 4 h. The solvent was removed in vacuo and the residue treated with ice-cold 2 N sodium hydroxide (400 mL). The resulting slurry was stirred for 30 min then extracted with dichloromethane (2×400 mL). The organics were combined, washed with water and brine, dried over anhydrous magnesium sulfate, filtered and pre-adsorbed onto silica. Purification by dry flash chromatography on silica, eluting with dichloromethane containing 0.5% triethylamine, afforded 5'-amino-3'-fluorobiphenyl-2-carbonitrile as a white solid (4.5 g, 58%): $\delta_H$ (400 MHz, CDCl$_3$) 3.90 (2H, br), 6.45 (1H, ddd, J 8, 2 and 2), 6.58–6.63 (2H, m), 7.44 (1H, ddd, J 8, 8 and 2), 7.48 (1H, dd, J 8 and 2), 7.62 (1H, ddd, J 8, 8 and 2), 7.74 (1H, dd, J 8 and 2).

f) 3'-Fluoro-5'-(4,4,5,5-tetramethyl[1,3,2]dioxaborolan-2-yl)biphenyl-2-carbonitrile A warm solution of 5'-amino-3'-fluorobiphenyl-2-carbonitrile (4.5 g, 21 mmol) in 1,4-dioxane (20 mL) was treated with 48% hydrobromic acid (100 mL) and the resulting suspension stirred and cooled to 3° C. (internal temperature). A solution of sodium nitrite (1.7 g, 24 mmol) in water (4 mL) was then added dropwise over 20 min keeping the internal temperature <5° C. Stirring at <5° C. was continued for 2 h before adding a cooled (5° C.) solution of copper(I) bromide (9.1 g, 3 mmol) in 48% hydrobromic acid (30 mL). The resulting purple reaction mixture was stirred at 5° C. for 10 min then warmed to 50° C. for 20 min.

The reaction was diluted with ice-cold water (500 mL) and extracted with ethyl acetate (2×200 mL). The organics were combined, washed with 5% aqueous sodium sulphite and saturated aqueous ammonium chloride, dried over anhydrous magnesium sulfate, filtered and pre-adsorbed onto silica gel. Purification on silica gel, eluting with isohexane (containing 1% methanol) on a gradient of ethyl acetate (5–15%) afforded 5'-bromo-3'-fluorobiphenyl-2-carbonitrile as a white solid (5.52 g, 94%).

A mixture of 5'-bromo-3'-fluorobiphenyl-2-carbonitrile (5.52 g, 20 mmol), potassium acetate (5.9 g, 60 mmol) and bis(pinacolato)diboron (6.1 g, 24 mmol) in 1,4-dioxane (60 mL) was degassed with nitrogen for 20 min. Dichloro[1,1'-bis(diphenylphosphino)ferrocene]palladium(II) dichloromethane adduct (500 mg, 0.6 mmol) was then added and the reaction heated at 90° C. for 24 h. The mixture was cooled to ambient temperature then partitioned between 2 N sodium hydroxide and diethyl ether. The aqueous layer was washed with a further portion of diethyl ether and the organics were discarded. The aqueous extract was made acidic (pH 6) with 36% hydrochloric acid and then extracted with diethyl ether. The organic extract was dried over anhydrous magnesium sulfate, filtered and pre-adsorbed onto silica gel. Purification by dry flash chromatography on silica gel, eluting with isohexane on a gradient of ethyl acetate (5–10%) afforded 3'-fluoro-5'-(4,4,5,5-tetramethyl[1,3,2]dioxaborolan-2-yl)biphenyl-2-carbonitrile as a colourless viscous oil (4.2 g, 65%) which crystallised on standing: $\delta_H$ (400 MHz, CDCl$_3$) 1.35 (12H, s), 7.36 (1H, ddd, J 8, 2 and 2), 7.46 (1H, ddd, J 8, 8 and 2), 7.52 (1H, dd, J 8 and 2), 7.57 (1H, ddd, J 8, 2 and 2), 7.64 (1H, ddd, J 8, 8 and 2), 7.70–7.72 (1H, m), 7.76 (1H, dd, J 8 and 2).

g) 3'-Fluoro-5'-(7-trifluoromethyl[1,8]naphthyridin-4-yl)biphenyl-2-carbonitrile 5-Chloro-2-trifluoromethyl[1,8]naphthyridine (50 mg, 0.22 mmol) was coupled to 3'-fluoro-5'-(4,4,5,5-tetramethyl[1,3,2]dioxaborolan-2-yl)biphenyl-2-carbonitrile (90 mg, 0.28 mmol) as described in Example 7 part g), affording 3'-fluoro-5'-(7-trifluoromethyl[1,8]naphthyridin-4-yl)biphenyl-2-carbonitrile (30 mg, 35%). $\delta_H$ (360 MHz, CDCl$_3$) 7.32–7.36 (1H, m), 7.41–7.44 (1H, m), 7.50–7.59 (3H, m), 7.64 (1H, d, J 4.6), 7.72 (1H, td, J 7.7 and 1.4), 7.85 (1H, dd, J 7.7 and 0.7), 7.90 (1H, d, J 8.8), 8.75 (1H, d, J 8.8), 9.30 (1H, d, J 4.2). m/z (ES$^+$) 394 [MH]$^+$.

EXAMPLE 17

2'-Fluoro-5'-(7-trifluoromethyl-[1,8]naphthyridin-4-yl)biphenyl-3-carbonitrile a) 5'-(5,5-Dimethyl[1,3,2]dioxaborinan-2-yl)-2'-fluorobiphenyl-3-carbonitrile 3-Bromobenzonitrile and 2-(2-fluoro-5-nitrophenyl)-4,4,5,5-tetramethyl-[1,3,2]dioxaborolane were coupled using the procedure described in Example 7 part c) to afford 2'-fluoro-5'-nitrobiphenyl-3-carbonitrile as a brown solid: $\delta_H$ (360 MHz, DMSO) 7.33–7.40 (2H, m), 7.46–7.55 (2H, m), 7.61 (1H, ddd, J 8, 8 and 2), 7.96–8.01 (1H, m), 8.61 (1H, dd, J 5 and 2), 8.77 (1H, s).

2'-Fluoro-5'-nitrobiphenyl-3-carbonitrile was reduced using the procedure described in Example 7 part d) to give 5'-amino-2'-fluorobiphenyl-3-carbonitrile as a brown solid: $\delta_H$ (360 MHz, CDCl$_3$) 3.66 (2H, s), 6.66–6.70 (1H, m), 6.71–6.74 (1H, m), 7.00 (1H, dd, J 9 and 9), 7.33–7.38 (1H, m), 7.44–7.49 (1H, m).

5'-Amino-2'-fluorobiphenyl-3-carbonitrile was bromodeaminated using the procedure described in Example 7 part e) to give 5'-bromo-2'-fluorobiphenyl-3-carbonitrile as a pale brown solid: $\delta_H$ (360 MHz, CDCl$_3$) 7.09 (1H, dd, J 9 and 9), 7.47–7.52 (1H, m), 7.53–7.59 (2H, m), 7.68 (1H, ddd, J 8, 1 and 1), 7.75 (1H, ddd, J 8, 1 and 1).

5'-Bromo-2'-fluorobiphenyl-3-carbonitrile was converted to 5'-(5,5-dimethyl-[1,3,2]dioxaborinan-2-yl)-2'-fluorobiphenyl-3-carbonitrile using the procedure described in Example 7 part f). This produced a brown oil that crystallised on standing: $\delta_H$ (360 MHz, CDCl$_3$) 1.04 (6H, s), 3.78 (4H, s), 7.15 (1H, dd, J 8 and 8), 7.53 (1H, dd, J 8 and 8), 7.62–7.65 (1H, m), 7.79–7.88 (4H, m).

b) 2'-Fluoro-5'-(7-trifluoromethyl-[1,8]naphthyridin-4-yl)biphenyl-3-carbonitrile 5-Chloro-2-trifluoromethyl[1,8]naphthyridine (50 mg, 0.22 mmol) was coupled to 5'-(5,5-dimethyl[1,3,2]dioxaborinan-2-yl)-2'-fluorobiphenyl-3-carbonitrile (87 mg, 0.28 mmol) as described in Example 7 part g), affording 2'-fluoro-5'-(7-trifluoromethyl-[1,8]naphthyridin-4-yl)biphenyl-3-carbonitrile (9 mg, 11%). $\delta_H$ (360 MHz, CDCl$_3$) 7.41–7.46 (1H, m), 7.51–7.63 (4H, m), 7.72 (1H, d, J 7.7), 7.79–7.87 (2H, m), 7.91 (1H, d, J 1.1), 8.52 (1H, d, J 8.8), 9.30 (1H, d, J 4.2). m/z (ES$^+$) 394 [MH]$^+$.

EXAMPLE 18

2'-Fluoro-5'-(7-trifluoromethyl[1,8]naphthyridin-4-yl)biphenyl-4-carbonitrile a) 5'-(5,5-dimethyl[1,3,2]dioxaborinan-2-yl)-2'-fluorobiphenyl-4-carbonitrile 4-Bromobenzonitrile and 2-(2-fluoro-5-nitrophenyl)-4,4,5,5-tetramethyl-[1,3,2]dioxaborolane were coupled using the procedure described in Example 7 part c) to afford 2'-fluoro-5'-nitrobiphenyl-4-carbonitrile as a brown solid: $\delta_H$(400 MHz, CDCl$_3$) 7.37 (1H, dd, J 9 and 9), 7.70 (2H, dd, J 8 and 1), 7.80 (1H, dd, J 8 and 1), 8.29–8.33 (1H, m), 8.37–8.40 (1H, m).

2'-Fluoro-5'-nitrobiphenyl-4-carbonitrile (3.03 g, 12.5 mmol) was reduced using the procedure described in Example 7 part d) to give crude 5'-amino-2'-fluorobiphenyl-4-carbonitrile as a brown solid.

5'-Amino-2'-fluorobiphenyl-4-carbonitrile was bromodeaminated following the procedure in Example 7 part e) to give 5'-bromo-2'-fluorobiphenyl-4-carbonitrile as a white solid: $\delta_H$ (360 MHz, CDCl$_3$) 7.08 (1H, dd, J 9 and 9), 7.47–7.52 (1H, m), 7.54–7.58 (1H, m), 7.63 (2H, dd, J 8 and 1), 7.75 (2H, dd, J 8 and 1).

5'-Bromo-2'-fluorobiphenyl-4-carbonitrile was converted to 5'-(5,5-dimethyl-[1,3,2]dioxaborinan-2-yl)-2'-fluorobiphenyl-4-carbonitrile using the procedure described in Example 7 part f). This produced a brown solid: $\delta_H$ (360 MHz, CDCl$_3$) 1.03 (6H, s), 3.77 (4H, s), 7.15 (1H, dd, J 8 and 8), 7.67–7.71 (4H, m), 7.80–7.83 (1H, m), 7.81 (1H, dd, J 8 and 2).

b) 2'-Fluoro-5'-(7-trifluoromethyl[1,8]naphthyridin-4-yl)biphenyl-4-carbonitrile 5-Chloro-2-trifluoromethyl[1,8]naphthyridine (50 mg, 0.22 mmol) was coupled to 5'-(5,5-dimethyl[1,3,2]dioxaborinan-2-yl)-2'-fluorobiphenyl-4-carbonitrile (87 mg, 0.28 mmol) as described in Example 7 part g), affording 2'-fluoro-5'-(7-trifluoromethyl[1,8]naphthyridin-4-yl)biphenyl-4-carbonitrile (21 mg, 25%). $\delta_H$ (360 MHz, CDCl$_3$) 7.41–7.46 (1H, m), 7.52–7.60 (3H, m), 7.71–7.82 (4H, m), 7.85 (1H, d, J 8.4), 8.52 (1H, d, J 8.8), 9.30 (1H, d, J 4.6). m/z (ES$^+$) 394 [MH]$^+$.

EXAMPLE 19

5-(6-Fluoro-2'-methanesulfonylbiphenyl-3-yl)-2-trifluoromethyl[1,8]-naphthyridine a) 2-Fluoro-2'-methylthio-5-nitrobiphenyl A mixture of 2-bromo-1-fluoro-4-nitrobenzene (5.89 g, 26.8 mmol), 2-(methylthio)benzeneboronic acid (5.62 g, 33.5 mmol) and potassium fluoride (5.13 g, 88.3 mmol) in tetrahydrofuran (70 mL) was degassed with nitrogen for 30 min. This mixture was then treated with tris(dibenzylideneacetone)dipalladium(0) (496 mg, 0.541 mmol) followed by tri-tert-butylphosphine (5.35 mL of a 0.2 M solution in 1,4-dioxane, 1.07 mmol) and the reaction was degassed for a further 10 min. The resulting slurry was then heated at 50° C. for 16 h under nitrogen. After cooling, the reaction mixture was partitioned between ethyl acetate (300 mL) and water (300 mL). The organic layer was washed with brine (200 mL), dried over anhydrous sodium sulphate, filtered and evaporated. Purification by chromatography on silica gel eluting with isohexane on a gradient of ethyl acetate (5–10%) gave 2-fluoro-2'-methylthio-5-nitrobiphenyl as a pale yellow solid (6.95 g, 99%): $\delta_H$ (360 MHz, CDCl$_3$) 2.42 (3H, s), 7.21–7.32 (3H, m), 7.37 (1H, d, J 7), 7.44 (1H, td, J 8 and 2), 8.27–8.31 (2H, m).

b) 2-Fluoro-2'-(methylthio)biphenyl-5-ylamine

A solution of 2-fluoro-2'-methylthio-5-nitrobiphenyl (6.00 g, 22.8 mmol) in tetrahydrofuran (50 mL) and ethanol (50 mL) was treated with tin(II) chloride dihydrate (25.70 g, 113.9 mmol) and the mixture was stirred at ambient temperature for 25 h. The solvent was evaporated and the residue stirred with 2 N sodium hydroxide solution (240 mL) for 18 h. The resulting suspension was extracted with dichloromethane (3×200 mL). The combined organic extracts were dried over anhydrous magnesium sulphate and evaporated. The residue was purified by flash chromatography on silica gel eluting with 35% ethyl acetate in isohexane to afford 2-fluoro-2'-(methylthio)biphenyl-5-ylamine as a white solid (5.20 g, 98%): $\delta_H$ (360 MHz, CDCl$_3$) 2.39 (3H, s), 6.60 (1H, dd, J 6 and 3), 6.64–6.68 (1H, m), 6.94 (1H, t, J 9), 7.19–7.20 (2H, m), 7.30 (1H, d, J 8), 7.33–7.37 (1H, m).

c) 5-Bromo-2-fluoro-2'-(methylthio)biphenyl

To a solution of 2-fluoro-2'-(methylthio)biphenyl-5-ylamine (397 mg, 1.70 mmol) in 1,4-dioxane (2.1 mL) was added 48% aqueous hydrobromic acid (8 ml) and the mixture was cooled to 3° C before the dropwise addition of sodium nitrite (137 mg, 1.98 mmol) in water (0.5 mL) over 5 min, while the temperature was kept below 5° C. The resulting mixture was stirred at 4±1° C. for 2 h 40 min then more sodium nitrite (26 mg, 0.37 mmol) in water (0.1 mL) was added dropwise and the mixture was stirred at 3° C. for 50 min. A cooled (3° C.) solution of copper(I) bromide (744 mg, 5.19 mmol) in 48% hydrobromic acid (2.4 mL) was added and the mixture was stirred at 3° C. for 15 min then heated to 50° C. for 1 h. The mixture was cooled to ambient temperature, diluted with water (50 mL) and extracted with ethyl acetate (4×35 mL). The combined organics were washed with 1 M aqueous sodium sulphite solution (30 mL), then saturated aqueous ammonium chloride solution (30 mL), dried over anhydrous magnesium sulphate and evaporated to give a brown oil. Purification by chromatography on silica gel eluting with isohexane on a gradient of ethyl acetate (0–2%) gave 5-bromo-2-fluoro-2'-(methylthio)biphenyl as a white solid (287 mg, 57%): $\delta_H$ (360 MHz, CDCl$_3$) 2.40 (3H, s), 7.04 (1H, t, J 9), 7.16–7.24 (2H, m), 7.32 (1H, d, J 8), 7.36–7.51 (4H, m).

d) 5-Bromo-2-fluoro-2'-(methanesulfonyl)biphenyl

To a cooled (0° C.) solution of 5-bromo-2-fluoro-2'-(methylthio)biphenyl (117 mg, 0.392 mmol) in anhydrous dichloromethane (7 mL) was added 3-chloroperoxybenzoic acid (55%, 309 mg, 0.984 mmol) portionwise over 5 min. The mixture was stirred for 30 min, the cooling bath was removed and stirring was continued for a further 6 h. The mixture was diluted with dichloromethane (20 mL) and washed with 5% aqueous sodium hydrogencarbonate (2×20 mL), brine (10 mL), dried over anhydrous magnesium sulphate and evaporated. The residue was purified by flash chromatography on silica gel, eluting with 30% ethyl acetate in isohexane, to afford 5-bromo-2-fluoro-2'-(methanesulfonyl)biphenyl as a colourless oil (100 mg, 77%): $\delta_H$ (360 MHz, CDCl$_3$) 2.90 (3H, s), 7.05 (1H, t, J 9), 7.37 (1H, dd, J 7 and 1), 7.49 (1H, dd, J 7 and 3), 7.51–7.55 (1H, m), 7.64 (1H, td, J 8 and 2), 7.69 (1H, td, J 8 and 2), 8.21 (1H, dd, J 8 and 1).

e) 2-(2-Fluoro-2'-(methanesulfonyl)biphenyl-5-yl)-4,4,5,5-tetramethyl-[1,3,2]dioxaborolane A mixture of 5-bromo-2-fluoro-2'-(methanesulfonyl)biphenyl (701 mg, 2.13 mmol), dried potassium acetate (418 mg, 4.26 mmol) and bis(pinacolato)diboron (622 mg, 2.45 mmol) in 1,4-dioxane (4.9 mL) and dimethylsulfoxide (0.1 mL) was degassed by bubbling nitrogen through the mixture for 45 min. Dichloro[1,1'-bis(diphenylphosphino)ferrocene]-palladium(II) dichloromethane adduct (52.2 mg, 0.0639 mmol) was added and the mixture was stirred at 90° C. under nitrogen for 16 h. After allowing to cool, the mixture was filtered through glass fibre paper (GF/A) and the solid was washed with a little dichloromethane. The combined filtrates were evaporated in vacuo and the residue was partitioned between 2 M aqueous sodium hydroxide (10 mL) and diethyl ether (10 mL). The aqueous layer was washed with more diethyl ether (10 mL), cooled in an ice-water bath then acidified to pH 6 with 36% hydrochloric acid causing a solid to precipitate. This precipitate was aged at 4° C. for 10 h, the solid was collected by filtration, washed with water and dried under vacuum to leave 2-(2-fluoro-2'-(methanesulfonyl)biphenyl-5-yl)-4,4,5,5-tetramethyl-[1,3,2]dioxaborolane as a pale grey solid (809 mg, 100%): $\delta_H$ (360 MHz, CDCl$_3$) 1.33 (12H, s), 2.87 (3H, s), 7.16 (1H, dd, J 10 and 8), 7.38 (1H, dd, J 7 and 1), 7.60(1H, m), 7.66 (1H, m), 7.78 (1H, dd, J 8 and 1), 7.85–7.89 (1H, m), 8.20 (1H, dd, J 8 and 1).

f) 5-(6-Fluoro-2'-methanesulfonylbiphenyl-3-yl)-2-trifluoromethyl[1,8]-naphthyridine 5-Chloro-2-trifluoromethyl[1,8]naphthyridine (50 mg, 0.22 mmol) was coupled to 2-(2-fluoro-2'-(methanesulfonyl)biphenyl-5-yl)-4,4,5,5-tetramethyl-[1,3,2]dioxaborolane (105 mg, 0.28 mmol) as described in Example 7 part g), affording 5-(6-fluoro-2'-methanesulfonylbiphenyl-3-yl)-2-trifluoromethyl[1,8]-naphthyridine (32 mg, 33%). $\delta_H$ (360 MHz, CDCl$_3$) 2.97 (3H, s), 7.38–7.46 (2H, m), 7.54–7.74 (5H, m), 7.87 (1H, d, J 8.4), 8.26 (1H, dd, J 1.2 and 7.9), 8.79 (1H, d, J 8.4), 9.27 (1H, d, J 4.2). m/z (ES$^+$) 447 [MH]$^+$.

EXAMPLE 20

5-(3'-Methoxybiphenyl-3-yl)-2-trifluoromethyl[1,8]naphthyridine

3-Bromo-3'-methoxybiphenyl (prepared as described in patent WO 0130764) was converted to 2-(3'-methoxybiphenyl-3-yl)-5,5-dimethyl[1,3,2]-dioxaborinane using the procedure described in Example 7 part f). The crude product of this transformation (83 mg, 0.28 mmol) was coupled to 5-chloro-2-trifluoromethyl[1,8]-naphthyridine (50 mg, 0.22 mmol) as described in Example 7 part g), affording 5-(3'-methoxybiphenyl-3-yl)-2-trifluoromethyl[1,8]naphthyridine (11 mg, 13%). $\delta_H$ (360 MHz, CDCl$_3$) 3.87 (3H, s), 6.95 (1H, m), 7.14–7.25 (2H, m), 7.40 (1H, t, J 7.9), 7.47 (1H, d, J 7.7), 7.56–7.69 (3H, m), 7.77–7.83 (2H, m), 8.59 (1H, d, J 8.8), 9.29 (1H, d, J 4.2). m/z (ES$^+$) 381 [MH]

EXAMPLE 21

5-[4-Fluoro-3-(3-fluoropyridin-4-yl)phenyl]-2-trifluoromethyl[1,8]naphthyridine a) 4-[2-Fluoro-5-(4,4,5,5-tetramethyl-[1,3,2]dioxaborolan-2-yl)phenyl]-3-fluoropyridine 3-Fluoro-4-bromopyridine (isolated as its hydrobromide salt) was prepared as described by Queguiner et al. in Tetrahedron, 1983, 39, 2009–2021. This was coupled with 2-(2-fluoro-5-nitrophenyl)-4,4,5,5-tetramethyl-[1,3,2]dioxaborolane using the Suzuki conditions described in Example 65 to give 4-(2-fluoro-5-nitrophenyl)-3-fluoropyridine: $\delta_H$ (360 MHz, CDCl$_3$) 7.37–7.42 (2H, m), 8.36–8.37 (1H, m), 8.38 (1H, s), 8.58 (1H, d, J 5), 8.65 (1H, d, J 1).

4-(2-Fluoro-5-nitrophenyl)-3-fluoropyridine was reduced using the procedure described in Example 5 part b) to give 4-(5-amino-2-fluorophenyl)-3-fluoropyridine as an off-white solid: m/z (ES$^+$) 207 (M$^+$+H).

4-(5-Amino-2-fluorophenyl)-3-fluoropyridine was bromo-deaminated as described in Example 4 part c) to give 4-(5-bromo-2-fluorophenyl)-3-fluoropyridine as a white solid: $\delta_H$ (360 MHz, CDCl$_3$) 7.11 (1H, t, J 10), 7.35 (1H, t, J 5), 7.55–7.58 (2H, m), 8.51 (1H, d, J 5), 8.59 (1H, d, J 1).

4-(5-Bromo-2-fluorophenyl)-3-fluoropyridine was reacted with bis(pinacolato)diboron by the method of Example 4 part d) to give 4-[2-fluoro-5-(4,4,5,5-tetramethyl-[1,3,2]dioxaborolan-2-yl)phenyl]-3-fluoropyridine as a buff-coloured solid: m/z (ES$^+$) 235 (M$^+$+H).

b) 5-[4-Fluoro-3-(3-fluoropyridin-4-yl)phenyl]-2-trifluoromethyl[1,8]-naphthyridine 5-Chloro-2-trifluoromethyl[1,8]naphthyridine (50 mg, 0.22 mmol) was coupled to 4-[2-fluoro-5-(4,4,5,5-tetramethyl-[1,3,2]dioxaborolan-2-yl)phenyl]-3-fluoropyridine (89 mg, 0.28 mmol) as described in Example 7 part g), affording 5-[4-fluoro-3-(3-fluoropyridin-4-yl)phenyl]-2-trifluoromethyl[1,8]naphthyridine (33 mg, 40%). $\delta_H$ (360 MHz, CDCl$_3$) 7.43–7.49 (2H, m), 7.58–7.61 (3H, m), 7.86 (1H, d, J 8.8), 8.55 (2H, dd, J 6.0 and 2.1), 8.63 (1H, d, J 1.8), 9.30 (1H, d, J 4.2). m/z (ES$^+$) 388 [MH]$^+$.

EXAMPLE 22

2-[2-Fluoro-5-(7-trifluoromethyl[1,8]naphthyridin-4-yl)phenyl]nicotinonitrile a) 4-Fluoro-3-(3-cyanopyridin-2-yl)phenylboronic acid 2-Chloronicotinonitrile (0.80 g, 5.8 mmol) was coupled to 2-(2-fluoro-5-nitrophenyl)-4,4,5,5-tetramethyl-[1,3,2]dioxaborolane (2 g, 7.49 mmol) using the method in Example 14 part a). Purification by chromatography on silica gel eluting with dichloromethane gave 2-(2-fluoro-5-nitrophenyl)nicotinonitrile as a yellow solid: $\delta_H$ (360 MHz, CDCl$_3$) 8.97 (1H, dd, J 5 and 2), 8.56 (1H, dd, J 6 and 3), 8.40–8.45 (1H, m), 8.15 (1H, dd, J 8 and 2), 7.55 (1H, dd, J 8 and 5), 7.43 (1H, dd, J 9 and 9); m/z (ES$^+$) 244 (M$^+$+H).

2-(2-Fluoro-5-nitrophenyl)nicotinonitrile (1.2 g, 4.9 mmol) was reduced by the method described in Example 5 part b). Purification by chromatography on silica gel eluting with dichloromethane containing 1% methanol gave 2-(5-amino-2-fluorophenyl)nicotinonitrile as an orange oil: $\delta_H$ (360 MHz, CDCl$_3$) 8.88 (1H, dd, J 5 and 2), 8.07 (1H, dd, J 8 and 2), 7.42 (1H, dd, J 8 and 5), 7.04 (1H, dd, J 9 and 9), 6.85 (1H, dd, J 6 and 3), 6.76–6.81 (1H, m); m/z (ES$^+$) 214 (M$^+$+H).

2-(5-Amino-2-fluorophenyl)nicotinonitrile (1.0 g, 4.7 mmol) was bromo-deaminated by the method described in Example 4 part c) to give 2-(5-bromo-2-fluorophenyl)nicotinonitrile as a white powder: $\delta_H$ (360 MHz, CDCl$_3$) 8.92 (1H, dd, J 5 and 1), 8.10 (1H, dd, J 8 and 2), 7.74 (1H, dd, J 6 and 2), 7.59–7.64 (1H, m), 7.48 (1H, dd, J 8 and 5), 7.15 (1H, dd, J 9 and 9).

A degassed solution of 2-(5-bromo-2-fluorophenyl)nicotinonitrile (1.53 g, 5.5 mmol) and bis(neopentyl glycolato)diboron (1.37 g, 6.1 mmol) was formed in 1,4-dioxane (50 mL) with dimethylsulfoxide (1 mL). Potassium acetate (1.08 g, 11.0 mmol) and dichloro[1,1'-bis(diphenylphosphino)ferrocene]palladium(II) dichloromethane adduct (60 mg, 0.1 mmol) were added and the mixture stirred at 80° C. for 18 h. The reaction was allowed to cool to ambient temperature and the solvent removed under reduced pressure. The residue was dissolved in 2 N sodium hydroxide solution (50 mL) and filtered. The filtrate was washed with diethyl ether (3×50 mL) then cooled to 0° C. and made neutral with 36% hydrochloric acid. The resulting precipitate was filtered and dried over phosphorus nentoxide to give 4-fluoro-3-(3-cyanopyridin-2-yl)phenylboronic acid as a white solid: m/z (ES$^+$) 242 (M$^+$+H).

b) 2-[2-Fluoro-5-(7-trifluoromethyl[1,8]naphthyridin-4-yl)phenyl]nicotinonitrile 5-Chloro-2-trifluoromethyl[1,8]naphthyridine (35 mg, 0.15 mmol) was coupled to 4-fluoro-3-(3-cyanopyridin-2-yl)phenylboronic acid (54 mg, 0.22 mmol) as described in Example 7 part g), affording 2-[2-fluoro-5-(7-trifluoromethyl[1,8]naphthyridin-4-yl)phenyl]nicotinonitrile (42 mg, 71%). $\delta_H$ (360 MHz, CDCl$_3$) 7.44–7.57 (2H, m), 7.62–7.70 (2H, m), 7.75 (1H, dd, J 2.5 and 6.7), 7.87 (1H, d, J 8.8), 8.17 (1H, dd, J 1.8 and 7.7), 8.62 (1H, d, J 8.4), 8.95 (1H, dd, J 1.6 and 4.7), 9.29 (1H, d, J 4.6). m/z (ES$^+$) 395 [MH]$^+$.

EXAMPLE 23

2-[2-Fluoro-5-(7-trifluoromethyl[1,8]naphthyridin-4-yl)phenyl]nicotinamide a) 4-Fluoro-3-(2-nicotinamide)phenylboronic acid During the work up of 4-fluoro-3-(2-nicotinonitrile)phenylboronic acid (Example 22, part a)), leaving the product in aqueous solution at pH 5 for extended periods of time resulted in hydrolysis of the product to give 4-fluoro-3-(2-nicotinamide)phenylboronic acid as a white solid: m/z (ES$^+$) 261 (M$^+$+H).

b) 2-[2-Fluoro-5-(7-trifluoromethyl[1,8]naphthyridin-4-yl)phenyl]nicotinamide

5-Chloro-2-trifluoromethyl[1,8]naphthyridine (50 mg, 0.22 mmol) was coupled to 4-fluoro-3-(2-nicotinamide)phenylboronic acid (73 mg, 0.28 mmol) as described in Example 7 part g), affording 2-[2-fluoro-5-(7-trifluoromethyl[1,8]-naphthyridin-4-yl)phenyl]nicotinamide (33 mg, 40%). $\delta_H$ (360 MHz, CDCl$_3$) 5.74 (2H, br d, J 55), 7.37 (1H, dd, J 8.4 and 9.5), 7.46 (1H, dd, J 4.9 and 7.7), 7.54–7.58 (1H, m), 7.63 (1H, d, J 4.2), 7.80–7.86 (2H, m), 8.08 (1H, dd, J 1.8 and 7.7), 8.62 (1H, d, J 8.8), 8.82 (1H, dd, J 1.6 and 4.7), 9.27 (1H, d, J 4.6). m/z (ES$^+$) 413 [MH]$^+$.

EXAMPLE 24

5-(3-Fluoro-5-pyridin-3-ylphenyl)-2-trifluoromethyl[1,8]naphthyridine a) 3-[3-(5,5-Dimethyl[1,3,2]dioxaborinan-2-yl)-5-fluorophenyl]pyridine This was prepared as described in Example 16, but using 3-bromopyridine instead of 2-bromobenzonitrile in step d), and using bis(neopentyl glycolato)diboron instead of bis(pinacolato)diboron in step f). $\delta_H$ (400 MHz, CDCl$_3$) 1.04 (6H, s), 3.79 (4H, s), 7.31–7.38 (2H, m), 7.49–7.52 (1H, m), 7.80 (1H, s), 7.89–7.92 (1H, m), 8.61 (1H, dd, J 1.6 and 5.1), 8.86 (1H, d, J 1.6). m/z (ES$^+$) 286 [MH]$^+$.

b) 5-(3-Fluoro-5-pyridin-3-ylphenyl)-2-trifluoromethyl[1,8] naphthyridine

5-Chloro-2-trifluoromethyl[1,8]naphthyridine (50 mg, 0.22 mmol) was coupled to 3-[3-(5,5-dimethyl[1,3,2]dioxaborinan-2-yl)-5-fluorophenyl]pyridine (80 mg, 0.28 mmol) as described in Example 7 part g), affording 5-(3- fluoro-5-pyridin-3-ylphenyl)-2-trifluoromethyl[1,8]naphthyridine (19 mg, 24%). $\delta_H$ (360 MHz, CDCl$_3$) 7.24–7.63 (1H, m), 7.41–7.45 (1H, m), 7.48–7.52 (2H, m), 7.63 (1H, d, J 4.6), 7.86 (1H, d, J 8.8), 7.92 (1H, dt, J 8.1 and 1.9), 8.55 (1H, d, J 8.8), 8.69 (1H, dd, J 1.6 and 4.7), 8.90 (1H, d, J 1.8), 9.32 (1H, d, J 4.6). m/z (ES$^+$) 370 [MH]$^+$.

EXAMPLE 25

5-(4-Fluoro-3-pyrimidin-4-ylphenyl)-2-trifluoromethyl[1,8]naphthyridine a) 4-Fluoro-3-pyrimidin-4-yl-phenylboronic acid 2,4-Dichloropyrimidine (2.0 g, 13 mmol) was coupled to 2-(2-fluoro-5-nitrophenyl)-4,4,5,5-tetramethyl-[1,3,2]dioxaborolane (3.9 g, 15 mmol) using the method in Example 14 part a). Purification by chromatography on silica gel eluting with dichloromethane containing 20% isohexane gave 2-chloro-4-(2-fluoro-5-nitro-phenyl)pyrimidine as a white solid: $\delta_H$ (400 MHz, CDCl$_3$) 7.40 (1H, dd, J 10 and 9), 7.85 (1H, dd, J 5 and 2), 8.38–8.43 (1H, m), 8.77 (1H, d, J 6), 9.16 (1H, q, J 3).

A solution of 2-chloro-4-(2-fluoro-5-nitrophenyl)pyrimidine (800 mg, 3.2 mmol) in ethanol (300 mL) was reduced under 40 p.s.i. hydrogen with platinum(IV) oxide (100 mg) for 30 minutes then filtered to give a solution of 3-(2-chloro-pyrimidin-4-yl)-4-fluorophenylamine: m/z (ES$^+$) 224 (M$^+$+H).

To the solution of 3-(2-chloro-pyrimidin-4-yl)-4-fluorophenylamine from above was added triethylamine (0.48 mL, 3.15 mmol) and palladium on active carbon (100 mg, 10% palladium) and the mixture was reduced under 40 p.s.i. hydrogen for 30 minutes. The mixture was filtered and the solvent removed to give 4-fluoro-3-pyrimidin-4-yl-phenylamine as a yellow solid: m/z (ES$^+$) 190 (M$^+$+H).

4-Fluoro-3-pyrimidin-4-yl-phenylamine (1.0 g, 5.3 mmol) was bromo-de-aminated using the method in Example 4 part c) to give 4-(5-bromo-2-fluoro-phenyl)pyrimidine as a white solid: $\delta_H$ (400 MHz, CDCl$_3$) 7.10 (1H, dd, J 11 and 9), 7.56–7.60 (1H, m), 7.83–7.85 (1H, m), 8.36 (1H, dd, J 7 and 3), 8.81 (1H, d, J 6), 9.32 (1H, d, J 1).

4-(5-Bromo-2-fluorophenyl)pyrimidine (503 mg, 2.0 mmol) was reacted with bis(neopentyl glycolato)diboron (494 mg, 2.2 mmol) using the method in Example 14 part c) to give 4-fluoro-3-pyrimidin-4-yl-phenylboronic acid as a tan solid: m/z (ES$^+$) 219 (M$^+$+H).

b) 5-(4-Fluoro-3-pyrimidin-4-ylphenyl)-2-trifluoromethyl[1,8]naphthyridine

5-Chloro-2-trifluoromethyl[1,8]naphthyridine (50 mg, 0.22 mmol) was coupled to 4-fluoro-3-pyrimidin-4-yl-phenylboronic acid (61 mg, 0.28 mmol) as described in Example 7 part g), affording 5-(4-fluoro-3-pyrimidin-4-ylphenyl)-2-trifluoromethyl[1,8]naphthyridine (20 mg, 25%). $\delta_H$ (360 MHz, CDCl$_3$) 7.46 (1H, dd, J 8.4 and 11.2), 7.60–7.64 (2H, m), 7.85 (1H, d, J 8.8), 7.96–7.98 (1H, m), 8.42 (1H, dd, J 2.5 and 7.4), 8.53 (1H, d, J 8.4), 8.87 (1H, d, J 5.3), 9.30 (1H, s), 9.31 (1H, s). m/z (ES$^+$) 371 [MH]$^+$.

EXAMPLE 26

5-[3-(2-Methyl-2H-tetrazol-5-yl)phenyl]-2-trifluoromethyl[1,8]naphthyridine a) 5-[3-(5,5-Dimethyl[1,3,2]dioxaborinan-2-yl)phenyl]-2-methyl-2H-tetrazole 5-(3-Bromophenyl)-2-methyl-2H-tetrazole (prepared as described in WO 9527692) was converted to 5-[3-(5,5-dimethyl[1,3,2]dioxaborinan-2-yl)phenyl]-2-methyl-2H-tetrazole as described in Example 7 part f). $\delta_H$ (360 MHz, DMSO) 0.98 (6H, s), 3.80 (4H, s), 4.43 (3H, s), 7.55 (1H, t, J 7.7), 7.83 (1H, d, J 7.4), 8.12 (1H, dt, J 7.7 and 1.4), 8.42 (1H, s). m/z (ES$^+$) 273 [MH]$^+$.

b) 5-[3-(2-Methyl-2H-tetrazol-5-yl)phenyl]-2-trifluoromethyl[1,8]naphthyridine

5-Chloro-2-trifluoromethyl[1,8]naphthyridine (50 mg, 0.22 mmol) was coupled to 5-[3-(5,5-dimethyl-[1,3,2]dioxaborinan-2-yl)phenyl]-2-methyl-2H-tetrazole (76 mg, 0.28 mmol) as described in Example 7 part g), affording 5-[3-(2-methyl-2H-tetrazol-5-yl)phenyl]-2-trifluoromethyl[1,8]naphthyridine (5 mg, 7%). $\delta_H$ (360 MHz, CDCl$_3$) 4.43 (3H, s), 7.59–7.65 (2H, m), 7.73 (1H, t, J 7.7), 7.83 (1H, d, J 8.4), 8.29 (1H, s), 8.34 (1H, d, J 7.4), 8.56 (1H, d, J 8.1), 9.30 (1H, d, J 3.9). m/z (ES$^+$) 357 [MH]$^+$.

EXAMPLE 27

5-(3-Furan-2-ylphenyl)-2-trifluoromethyl[1,8]naphthyridine a) 2-(3-Furan-2-ylphenyl)-5,5-dimethyl[1,3,2]dioxaborinane 2-(3-Bromophenyl)furan (prepared as described in J. Org. Chem, 1997, 62, 7295–7304) was converted to 2-(3-furan-2-ylphenyl)-5,5-dimethyl[1,3,2]-dioxaborinane as described in Example 7 part f). $\delta_H$ (360 MHz, DMSO) 0.97 (6H, s), 3.78 (4H, s), 6.58 (1H, q, J 1.8), 6.94 (1H, d, J 3.2), 7.41 (1H, t, J 7.7), 7.61 (1H, d, J 7.4), 7.73–7.79 (2H, m), 8.01 (1H, s).

b) 5-(3-Furan-2-ylphenyl)-2-trifluoromethyl[1,8]naphthyridine

5-Chloro-2-trifluoromethyl[1,8]naphthyridine (50 mg, 0.22 mmol) was coupled to 2-(3-furan-2-ylphenyl)-5,5-dimethyl[1,3,2]-dioxaborinane (72 mg, 0.28 mmol) as described in Example 7 part g), affording 5-(3-furan-2-ylphenyl)-2-trifluoromethyl[1,8]naphthyridine (36 mg, 49%). $\delta_H$ (360 MHz, CDCl$_3$) 6.53 (1H, q, J 1.8), 6.75 (1H, d, J 3.2), 7.35–7.38 (1H, m), 7.51 (1H, d, J 1.1), 7.55–7.62 (2H, m), 7.79–7.86 (3H, m), 8.57 (1H, d, J 8.4), 9.29 (1H, d, J 4.2). m/z (ES$^+$) 341 [MH]$^+$.

EXAMPLE 28

5-[3-(Pyridin-2-ylmethoxy)phenyl]-2-trifluoromethyl[1,8]naphthyridine a) 2-[3-(5,5-Dimethyl[1,3,2]dioxaborinan-2-yl)phenoxymethyl]pyridine 3-Bromophenol (1.00 g, 5.8 mmol), 2-picolyl chloride hydrochloride (950 mg, 5.8 mmol) and potassium carbonate (3.20 g, 23 mmol) were stirred together in DMF (10 mL) at room temperature overnight. The solvent was removed in vacuo, azeotroping with xylene to remove the last traces of DMF. The residual material was partitioned between ethyl acetate (70 mL) and water (70 mL), then the organic phase was washed with saturated sodium chloride solution (1×50 mL), was dried over magnesium sulfate, and was concentrated in vacuo to afford 2-(3-bromophenoxymethyl)pyridine (1.48 g, 97%). m/z (ES$^+$) 265 [MH]$^+$.

2-(3-Bromophenoxymethyl)pyridine (1.48 g, 5.6 mmol) was converted to 2-[3-(5,5-dimethyl[1,3,2]dioxaborinan-2-yl)phenoxymethyl]pyridine (1.55 g, 93%) by the procedure described in Example 7 part f). $\delta_H$ (360 MHz, CDCl$_3$) 1.02 (6H, s), 3.76 (4H, s), 5.24 (2H, s), 7.04–7.07 (1H, m), 7.23 (1H, dd, J 5.4 and 6.8), 7.19–7.25 (1H, m), 7.29 (1H, t, J 8.1), 7.42 (1H, d, J 7.4), 7.47 (1H, d, J 2.5) 7.55 (1H, d, J 7.7), 7.71 (1H, td, J 7.7 and 1.8), 8.60 (1H, d, J 4.2). m/z (ES$^+$) 230 [M-C$_5$H$_8$]$^+$.

b) 5-[3-(Pyridin-2-ylmethoxy)phenyl]-2-trifluoromethyl[1,8]naphthyridine

5-Chloro-2-trifluoromethyl[1,8]naphthyridine (50 mg, 0.22 mmol) was coupled to 2-[3-(5,5-dimethyl[1,3,2]

dioxaborinan-2-yl)phenoxymethyl]pyridine (83 mg, 0.28 mmol) as described in Example 7 part g), affording 5-[3-(pyridin-2-ylmethoxy)phenyl]-2-trifluoromethyl[1,8]naphthyridine (36 mg, 34%). $\delta_H$ (360 MHz, CDCl$_3$) 5.28 (2H, s), 7.07–7.11 (2H, m), 7.20 (1H, dd, J 2.1 and 8.4), 7.23–7.30 (1H, m), 7.47–7.56 (3H, m), 7.73–7.78 (2H, m), 8.50 (1H, d, J 8.8), 8.61 (1H, d, J 4.6), 9.26 (1H, d, J 4.6). m/z (ES$^+$) 382 [MH]$^+$.

EXAMPLE 29

5-(4-Fluoro-3-morpholin-4-ylmethylphenyl)-2-trifluoromethyl[1,8]naphthyridine a) 4-[5-(5,5-Dimethyl[1,3,2]dioxaborinan-2-yl)-2-fluorobenzyl]morpholine To 5-bromo-2-fluorobenzaldehyde (2.50 g, 12 mmol) and morpholine (1.61 mL, 1.61 g, 18 mmol) in 1,2-dichloroethane (100 mL) was added sodium triacetoxyborohydride (5.21 g, 2.5 mmol) portionwise with stirring at room temperature over 5 min. The mixture was stirred under nitrogen for 1 h, then 2 N sodium hydroxide solution (100 mL) was added, and the mixture was stirred for a further 5 min. The biphasic mixture was separated, and the aqueous layer was washed with dichloromethane (2×75 mL). The combined organic layers were washed with saturated sodium chloride solution (1×50 mL) and were concentrated in vacuo. The crude product was purified by flash chromatography on silica gel, eluting with 75% diethyl ether in isohexane (+1% triethylamine), to yield 4-(5-bromo-2-fluorobenzyl)morpholine (3.18 g, 94%).

4-(5-bromo-2-fluorobenzyl)morpholine (1.00 g, 3.7 mmol) was converted to 4-[5-(5,5-dimethyl[1,3,2]dioxaborinan-2-yl)-2-fluorobenzyl]morpholine (1.12 g, 100%) by the procedure described in Example 7 part f). $\delta_H$ (360 MHz, CDCl$_3$) 1.02 (6H, s), 2.49 (4H, t, J 4.4), 3.71 (4H, t, J 4.6), 3.76 (4H, s), 7.01 (1H, dd, J 10.2 and 8.1), 7.70 (1H, m), 7.76 (1H, dd, J 8.1 and 1.4). m/z (ES$^+$) 240 [M-C$_5$H$_8$]$^+$.

b) 5-(4-Fluoro-3-morpholin-4-ylmethylphenyl)-2-trifluoromethyl[1,8]-naphthyridine 5-Chloro-2-trifluoromethyl[1,8]naphthyridine (50 mg, 0.22 mmol) was coupled to 4-[5-(5,5-dimethyl[1,3,2]dioxaborinan-2-yl)-2-fluorobenzyl]morpholine (86 mg, 0.28 mmol) as described in Example 7 part g), affording 5-(4-fluoro-3-morpholin-4-ylmethylphenyl)-2-trifluoromethyl[1,8]naphthyridine (10 mg, 12%). $\delta_H$ (360 MHz, CDCl$_3$) 2.54 (4H, t, J 4.2), 3.68 (2H, s), 3.71 (4H, t, J 4.4), 7.26 (1H, t, 8.8), 7.37 (1H, m), 7.55–7.58 (2H, m), 7.82 (1H, d, J 8.4), 8.49 (1H, d, J 8.4), 9.27 (1H, d, J 4.2). m/z (ES$^+$) 392 [MH]$^+$.

EXAMPLE 30

5-[3-(3,5-Difluoropyridin-2-yl)-4-fluorophenyl]-2-trifluoromethyl[1,8]-naphthyridine a) 2,4-Dibromo-3,5-difluoro-6-(2-fluoro-5-nitrophenyl)pyridine To a degassed mixture of 3,5-difluoro-2,4,6-tribromopyridine (4.26 g, 12.1 mmol), 2-(2-fluoro-5-nitrophenyl)-4,4,5,5-tetramethyl-[1,3,2]dioxaborolane (2.80 g, 10.4 mmol), aqueous sodium carbonate (10 mL of a 2 M solution) and tetrahydrofuran (40 mL) was added tetrakis(triphenylphosphine)palladium(0) (0.67 g). The mixture was then stirred at 55° C. for 48 h under an atmosphere of nitrogen. The reaction mixture was then partitioned between water and ethyl acetate. The organic layer was separated and evaporated and the residue chromatographed on silica gel eluting with isohexane on a gradient of dichloromethane (20–40%) to afford 2,4-dibromo-3,5-difluoro-6-(2-fluoro-5-nitrophenyl)pyridine as a solid (1.21 g). $\delta_H$ (400 MHz, CDCl$_3$) 7.37 (1H, t, J 9), 8.38 (1H, m), 8.55 (1H, dd, J 6 and 3).

b) 3-(3,5-Difluoropyridin-2-yl)-4-fluorophenylamine

To 2,4-dibromo-3,5-difluoro-6-(2-fluoro-5-nitrophenyl)pyridine (1.20 g, 2.91 mmol) dissolved in dichloromethane (30 mL) was added triethylamine (3 mL) and ethanol (80 mL) followed by 10% palladium on carbon (0.536 g). The mixture was then shaken under an atmosphere of hydrogen gas at 45 psi until complete reaction was indicated by TLC (0.25 to 3.5 h). The catalyst was then removed by filtration through glass microfibre filter paper (GF/A) and the solvent stripped at reduced pressure to afford 3-(3,5-difluoropyridin-2-yl)-4-fluorophenylamine which was used subsequently without further purification: m/z (ES$^+$) 225 (MH$^+$).

c) 2-(5-Bromo-2-fluorophenyl)-3,5-difluoropyridine

To the 3-(3,5-difluoropyridin-2-yl)-4-fluorophenylamine prepared above was added 1,4-dioxane (5 mL) and 48% aqueous hydrogen bromide (15 mL). The solution was cooled to −10° C. and a solution of sodium nitrite (0.252 g) in water (1 mL) was added dropwise with stirring at such a rate as to maintain an internal temperature below −5° C. The mixture was then stirred for a further 1 h at <0° C. before a solution of copper(I) bromide (1.283 g) in 48% aqueous hydrogen bromide (5 mL) was added slowly with stirring to maintain a reaction temperature below 10° C. This mixture was then stirred at 10° C. for 1 h, ambient temperature a further 1 h and then heated at 35° C. for 30 min. The reaction mixture was then cooled in an ice-water bath and 4 N aqueous sodium hydroxide (41 mL) was added slowly with stirring, followed by 30% aqueous ammonia (15 mL). The resulting mixture was extracted with ethyl acetate. The organic extract was evaporated and the residue subjected to chromatography on silica gel, eluting with 10% diethyl ether in isohexane, to afford 2-(5-bromo-2-fluorophenyl)-3,5-difluoropyridine (0.48 g) as a colourless solid: m/z (ES$^+$) 288, 290 (MH$^+$).

d) 4-Fluoro-3-(3,5-difluoropyridin-2-yl)phenylboronic acid

To 2-(5-bromo-2-fluorophenyl)-3,5-difluoropyridine (0.746 g, 2.59 mmol), and bis(neopentyl glycolato)diboron (0.704 9) was added dry 1,4-dioxane (9 mL) and dry dimethylsulfoxide (1.1 mL) followed by potassium acetate (0.542 g) and dichloro[1,1'-bis(diphenylphosphino)ferrocene]-palladium(II) dichloromethane adduct (0.080 g). The mixture was thoroughly degassed with nitrogen and then stirred at 85° C. for 24 h. On cooling to ambient temperature 1 N aqueous sodium hydroxide (24 mL) was added and the mixture stirred for 30 min. Diethyl ether was added and the aqueous phase separated and washed with diethyl ether. The organics were discarded. The aqueous phase was filtered then acidified to pH 5 by addition of 2 N aqueous hydrochloric acid (12 mL). The resulting solid was collected by filtration, washed with water and dried in vacuo at 60° C. to afford 4-fluoro-3-(3,5-difluoropyridin-2-yl)phenylboronic acid (0.618 g) as a colourless solid: $\delta_H$ (400 MHz, DMSO) 8.69 (1H, d, J 2), 8.21 (2H, s), 7.94–8.14 (3H, m), 7.34 (1H, dd, J 11 and 8).

e) 5-[3-(3,5-Difluoropyridin-2-yl)-4-fluorophenyl]-2-trifluoromethyl[1,8]-naphthyridine 5-Chloro-2-trifluoromethyl[1,8]naphthyridine (50 mg, 0.22 mmol) was coupled to 4-fluoro-3-(3,5-difluoropyridin-2-yl)phenylboronic acid (71 mg, 0.28 mmol) as described in Example 7 part g), affording 5-[3-(3,5-difluoropyridin-2-yl)-4-fluorophenyl]-2-trifluoromethyl[1,8]-naphthyridine (59 mg, 68%). $\delta_H$ (360 MHz, CDCl$_3$) 7.36–7.44 (2H, m), 7.55–7.62 (2H, m), 7.75 (1H, dd, J 2.3 and 6.5), 7.85 (1H, d, J 8.8), 8.48 (1H, d, J 2.1), 8.57 (1H, d, J 8.8), 9.28 (1H, d, J 4.2). m/z (ES$^+$) 406 [MH]$^+$.

EXAMPLE 31

2'-Fluoro-5'-(7-trifluoromethyl[1,8]naphthyridin-4-yl)biphenyl-2-carbonitrile

5-Chloro-2-trifluoromethyl[1,8]naphthyridine (50 mg, 0.22 mmol) was coupled to 2'-fluoro-5'-(4,4,5,5- tetramethyl-[1,3,2]dioxaborolan-2-yl)biphenyl-2-carbonitrile (prepared as described in Example 2, steps a) to e), 90 mg, 0.28 mmol) as described in Example 7 part g), affording 2'-fluoro-5'-(7-trifluoromethyl[1,8]naphthyridin-4-yl)biphenyl-2-carbonitrile (56 mg, 66%). $\delta_H$ (360 MHz, CDCl$_3$) 7.47 (1H, t, J 9.3), 7.53–7.62 (5H, m), 7.71 (1H, td, J, 7.7 and 1.4), 7.85 (1H, dd, J 7.7 and 0.7), 7.88 (1H, d, J 8.4), 8.71 (1H, d, J 8.8), 9.28 (1H, d, J 4.6). m/z (ES$^+$) 394 [MH]$^+$.

EXAMPLE 32

5-(4-Fluoro-3-pyridin-2-yl)-2-trifluoromethyl[1,8]naphthyridine a) 2-(2-Fluoro-5-nitrophenyl)pyridine A mixture of 2-bromo-1-fluoro-4-nitrobenzene (2.0 g, 9.1 mmol) and 2-(1,1,1-tributylstannyl)pyridine (3.36 g, 9.11 mmol) in THF (80 mL) and DMF (10 mL) was degassed with nitrogen. [1,1'-Bis(diphenylphosphino)ferrocene]-dichloropalladium(II) complex with dichloromethane (200 mg, 3 mol %) was added, and the mixture was heated at reflux for 24 h. More 2-bromo-1-fluoro-4-nitrobenzene (0.60 g, 2.7 mmol) and catalyst (100 mg, 1.5 mol %) were added, and the mixture was heated as before for another 24 h. The solvent was removed in vacuo, and the residue was purified by flash chromatography on silica gel, eluting with 50% dichloromethane in isohexane, then 100% dichloromethane, then 100% ethyl acetate (UV detection). 2-(2-Fluoro-5-nitrophenyl)pyridine was isolated as a colourless solid (2.11 g, 100%). $\delta_H$ (400 MHz, CDCl$_3$) 7.30–7.37 (2H, m), 7.80–7.87 (2H, m), 8.27 (1H, m), 8.78 (1H, m), 9.01 (1H, dd, J 3.1, 6.7); MS (ES$^+$) m/z 219 [M+H]$^+$.

b) 4-Fluoro-3-(pyridin-2-yl)aniline

To 2-(2-fluoro-5-nitrophenyl)pyridine (2.11 g, 9.68 mmol) in ethanol (40 mL) stirred in a water bath at 20° C., was added dry tin(II) chloride (7.10 g, 37.3 mmol) portionwise. The mixture was then stirred at room temperature for 18 h. Aqueous ammonia (40 mL of a 25% solution) was added, and the solvent was removed in vacuo, azeotroping with ethanol to remove traces of water. The residue was sequentially boiled in ethyl acetate and filtered three times. The combined filtrates were concentrated in vacuo to yield 4-fluoro-3-(pyridin-2-yl)aniline as a yellow solid (1.54 g, 85%). $\delta_H$ (400 MHz, CDCl$_3$) 3.65 (2H, br s), 6.68 (1H, m), 6.98 (1H, dd, J 8.6, 11.0), 7.22–7.31 (2H, m), 7.71–7.83 (2H, m), 8.70 (1H, m); MS (ES$^+$) m/z 189 [M+H]$^+$.

c) 2-(5-Bromo-2-fluorophenyl)pyridine

To a solution of copper(II) bromide (2.0 g, 8.6 mmol) in anhydrous acetonitrile (30 mL) was added tert-butyl nitrite (1.64 mL, 1.42 g, 13.8 mmol)dropwise with stirring at 4° C. A solution of 4-fluoro-3-(pyridin-2-yl)aniline (1.54 g, 8.2 mmol) in acetonitrile (10 mL) was added dropwise with stirring over 5 min, then the mixture was allowed to warm to room temperature and was stirred for 16 h. The mixture was partitioned between ethyl acetate and 25% aqueous ammonia, and the aqueous phase was further extracted with ethyl acetate. The combined organic layers were washed with saturated brine and were concentrated in vacuo. The residual material was purified by flash chromatography on silica gel, eluting with dichloromethane, affording 2-(5-bromo-2-fluorophenyl)pyridine (669 mg, 32%). $\delta_H$ (400 MHz, CDCl$_3$) (1H, s), 7.07 (1H, dd, J 8.6, 10.6), 7.29 (1H, m), 7.48 (1H, m), 7.77–7.79 (2H, m), 8.17 (1H, dd, J 2.5, 6.8), 8.73 (1H, m); MS (ES$^+$) m/z 252/254 [M]$^+$.

d) 4-Fluoro-3-(pyridin-2-yl)phenylboronic acid

To 2-(5-bromo-2-fluorophenyl)pyridine (544 mg, 2.16 mmol) and bis(neopentyl glycolato)diboron (585 mg, 2.60 mmol) under nitrogen was added dry potassium acetate (450 mg, 4.58 mmol), anhydrous dioxane (8 mL) and DMSO (1 mL). The mixture was degassed with nitrogen, and [1,1'-bis(diphenylphosphino)-ferrocene]dichloropalladium(II) complex with dichloromethane (50 mg, 3 mol %) was added. After stirring at 85° C. under nitrogen for 15 h, the mixture was cooled to room temperature, and sodium hydroxide solution (20 mL of a 1 M solution) was added. The mixture was stirred for 10 min, and was then extracted twice with diethyl ether. The combined ether extractions were washed with water, then the combined aqueous layers were filtered through a glass fibre filter paper. The pH of the filtrate was adjusted to 6 by the addition of 2 N hydrochloric acid-precipitating a white solid. This was collected by filtration, washed with water and dried in vacuo at 60° C., and was found to be 4-fluoro-3-(pyridin-2-yl)phenylboronic acid (455 mg, 97%). $\delta_H$ (400 MHz, DMSO) 7.30 (1H, dd, J 8.2, 11.7), 7.41 (1H, m), 7.77 (1H, m), 7.90 (2H, m), 8.16 (2H, s), 8.36 (1H, dd, J 1.6, 8.6), 8.72 (1H, m); MS (ES$^+$) 218.

e) 5-(4-Fluoro-3-pyridin-2-yl)-2-trifluoromethyl[1,8]naphthyridine

5-Chloro-2-trifluoromethyl[1,8]naphthyridine (50 mg, 0.22 mmol) was coupled to 4-fluoro-3-(pyridin-2-yl)phenylboronic acid (61 mg, 0.28 mmol) as described in Example 7 part g), affording 5-(4-fluoro-3-pyridin-2-yl)-2-trifluoromethyl-[1,8]naphthyridine (39 mg, 49%). $\delta_H$ (360 MHz, CDCl$_3$) 7.32 (1H, ddd, J 7.7, 4.9 and 1.1), 7.40 (1H, dd, J 10.9 and 8.4), 7.49–7.52 (1H, m), 7.63 (1H, d, J 4.2), 7.80–7.84 (2H, m), 7.92 (1H, dt, J 8.1 and 1.1), 8.22 (1H, dd, J 2.1 and 7.4), 8.57 (1H, d, J 8.8), 8.70–8.74 (1H, m), 9.28 (1H, d, J 4.2). m/z (ES$^+$) 370 [MH]+.

EXAMPLE 33

6,2'-Difluoro-5'-(7-trifluoromethyl[1,8]naphthyridin-4-yl)biphenyl-3-carbonitrile a) 6,2'-Difluoro-5'-(4,4,5,5-tetramethyl[1,3,2]dioxaborolan-2-yl)biphenyl-3-carbonitrile 3-Bromo-4-fluorobenzonitrile (2.00 g, 10 mmol) was coupled to 2-(2-fluoro-5-nitrophenyl)-4,4,5,5-tetramethyl-[1,3,2]dioxaborolane (4.01 g, 15 mmol) following the procedure described in Example 14 part a), affording 6,2'-difluoro-5'-nitrobiphenyl-3-carbonitrile as a brown solid (2.60 g, 100%). $\delta_H$ (360 MHz, CDCl$_3$) 7.38 (2H, q, J 8.8), 7.77–7.82 (2H, m), 8.33–8.38 (2H, m).

6,2'-Difluoro-5'-nitrobiphenyl-3-carbonitrile (2.60 g, 10 mmol) was reduced following the procedure described in Example 5 part b), affording 5'-amino-6,2'-difluorobiphenyl-3-carbonitrile as a brown solid (2.30 g, 100%). $\delta_H$ (360 MHz, CDCl$_3$) 3.65 (2H, br s), 6.64 (1H, dd, J 2.8, 6.0), 6.69–6.74 (1H, m), 6.99 (1H, t, J 9.1), 7.26 (1H, t, J 9.0), 7.65–7.80 (2H, m). m/z (ES$^+$) 231 [MH]$^+$.

5'-Amino-6,2'-difluorobiphenyl-3-carbonitrile (2.30 g, 10 mmol) was bromodeaminated following the procedure described in Example 2 part d), affording 5'-bromo-6,2'-difluorobiphenyl-3-carbonitrile as an orange solid (644 mg, 22%). $\delta_H$ (360 MHz, CDCl$_3$) 7.10 (1H, t, J 9.1), 7.30 (1H, t, J 9.1), 7.50–7.57 (2H, m), 7.71–7.75 (2H, m).

5'-Bromo-6,2'-difluorobiphenyl-3-carbonitrile (640 mg, 2.2 mmol) was converted into 6,2'-difluoro-5'-(4,4,5,5-tetramethyl[1,3,2]dioxaborolan-2-yl)biphenyl-3-carbonitrile (477 mg, 64%) following the procedure described in Example 4 part d). $\delta_H$ (360 MHz, DMSO) 1.31 (12H, s), 7.40 (1H, dd, J 8.4 and 2.1), 7.59 (1H, t, J 9.1), 7.74 (1H, dd, J 1.1, 8.1), 7.80–7.84 (1H, m), 8.01–8.05 (1H, m), 8.12 (1H, dd, J 1.9 and 6.8).

b) 6,2'-Difluoro-5'-(7-trifluoromethyl[1,8]naphthyridin-4-yl)biphenyl-3-carbonitrile 5-Chloro-2-trifluoromethyl[1,8]naphthyridine (50 mg, 0.22 mmol) was coupled to 6,2'-difluoro-5'-(4,4,5,5- tetramethyl[1,3,2]dioxaborolan-2-yl)biphenyl-3-carbonitrile (96 mg, 0.28 mmol) as described in Example 7 part g), affording 6,2'-difluoro-5'-(7-trifluoromethyl[1,8]naphthyridin-4-yl)biphenyl-3-carbonitrile (24 mg, 27%). $\delta_H$ (400 MHz, CDCl$_3$) 7.35 (1H, t, J 9.0), 7.45 (1H, t, J 9.0), 7.52–7.61 (3H, m), 7.74–7.78 (1H, m), 7.83 (1H, dd, J 1.4 and 6.5), 7.87 (1H, d, J 8.6), 8.54 (1H, d, J 8.2), 9.30 (1H, d, J 4.3). m/z (ES) 412 [MH]$^+$.

EXAMPLE 34

5-(4-Fluoro-3-methoxyphenyl)-2-trifluoromethyl[1,8]naphthyridine a) 2-(4-Fluoro-3-methoxyphenyl)-4,4,5,5-tetramethyl[1,3,2]dioxaborolane A mixture of 3-bromo-6-fluoroanisole (4.68 g, 3 mmol), potassium acetate (4.48 g, 46 mmol) and bis(pinacolato)diboron (6.67 g, 26 mmol) in dioxane (50 mL) was degassed via three "freeze-thaw" cycles. [1,1'-Bis(diphenylphosphino)ferrocene]dichloropalladium(II) complex with dichloromethane (559 mg, 0.69 mmol) was added and the mixture was degassed as before, then was stirred at 90° C. overnight. After cooling to room temperature, the mixture was filtered, and the filtrate was concentrated in vacuo. The crude product was partitioned between 2 N sodium hydroxide solution (60 mL) and diethyl ether (60 mL). The separated aqueous layer was acidified to ~pH 1 with conc. hydrochloric acid. An oil separated out, which solidified upon trituration. This was separated by filtration, and found to be 2-(4-fluoro-3-methoxy-phenyl)-4,4,5,5-tetramethyl-[1,3,2]dioxaborolane (4.11 g, 72%). $\delta_H$ (400 MHz, CDCl$_3$) 1.34 (12H, s), 3.92 (3H, s), 7.08 (1H, dd, J 8.2 and 11.7), 7.35–7.40 (2H, m).

b) 5-(4-Fluoro-3-methoxyphenyl)-2-trifluoromethyl[1,8]naphthyridine

5-Chloro-2-trifluoromethyl[1,8]naphthyridine (923 mg, 4.0 mmol) was coupled to 2-(4-fluoro-3-methoxyphenyl)-4,5,5,5-tetramethyl-[1,3,2]dioxaborolane (1.30 g, 5.2 mmol) as described in Example 3 part g), affording 5-(4-fluoro-3-methoxyphenyl)-2-trifluoromethyl[1,8]naphthyridine (1.06 g, 83%). $\delta_H$ (360 MHz, CDCl$_3$) 3.95 (3H, s), 6.99–7.04 (1H, m), 7.06 (1H, dd, J 7.7 and 2.1), 7.30 (1H, dd, J 2.5 and 8.4), 7.56 (1H, d, J 4.2), 7.82 (1H, d, J 8.4), 8.52 (1H, d, J 8.4), 9.27 (1H, d, J 4.2). m/z (ES$^+$) 323 [MH]$^+$.

EXAMPLE 35

5-(3'-Chloro-6-fluorobiphenyl-3-yl)-2-trifluoromethyl[1,8]naphthyridine a) 2-Fluoro-5-(7-trifluoromethyl-[1,8]naphthyridin-4-yl)phenol To 5-(4-fluoro-3-methoxyphenyl)-2-trifluoromethyl[1,8]naphthyridine (prepared as described in Example 34; 1.00 g, 3.1 mmol) in dichloromethane (20 mL) was added boron (III) bromide (9.31 mL of a 1 M solution in dichloromethane, 9.3 mmol) dropwise with stirring at 0° C., and the resulting mixture was stirred at 0° C. for 1 h. Methanol (2 mL) was added dropwise at 0° C. with stirring—Care! Large exotherm observed!—then the mixture was poured into saturated sodium hydrogencarbonate solution (50 mL). Effervescence was observed, and a yellow solid was precipitated, which was separated by filtration, washed with water and dried in a drying pistol at 60° C. This was 2-fluoro-5-(7-trifluoromethyl-[1,8]naphthyridin-4-yl)phenol (881 mg, 92%). $\delta_H$ (400 MHz, DMSO) 7.01–7.04 (1H, m), 7.16 (1H, dd, J 2.3 and 8.2), 7.40 (1H, dd, J 8.2 and 11.3), 7.74 (1H, d, J 4.3), 8.09 (1H, d, J 8.6), 8.66 (1H, d, J 8.6), 9.27 (1H, d, J 4.3), 10.30 (1H, s). m/z (ES$^+$) 309 [MH]$^+$.

b) Trifluoromethanesulfonic acid 2-fluoro-5-(7-trifluoromethyl-[1,8]naphthyridin-4-yl)phenyl ester A slurry of 2-fluoro-5-(7-trifluoromethyl-[1,8]naphthyridin-4-yl)phenol (500 mg, 1.6 mmol) in dichloromethane (20 mL) was stirred with N-phenyltrifluoromethanesulfonimide (695 mg, 2.0 mmol) and triethylamine (294 µL, 213 mg, 2.1 mmol) at room temperature overnight. The resulting solution was washed with saturated ammonium chloride solution (1×20 mL) and water (1×20 mL), then was dried over magnesium sulfate and concentrated in vacuo. The residual product was purified by flash chromatography on silica gel, eluting with 5% ethyl acetate in dichloromethane, affording trifluoromethanesulfonic acid 2-fluoro-5-(7-trifluoromethyl-[1,8]naphthyridin-4-yl)phenyl ester as a colourless glass, which solidified upon standing (587 mg, 82%). $\delta_H$ (360 MHz, CDCl$_3$) 7.49–7.55 (3H, m), 7.57 (1H, d, J 4.2), 7.88 (1H, d, J 8.8), 8.43 (1H, d, J 8.4), 9.32 (1H, d, J 4.6). m/z (ES$^+$) 441 [MH]$^+$.

c) 5-(3'-Chloro-6-fluorobiphenyl-3-yl)-2-trifluoromethyl[1,8]naphthyridine

A mixture of trifluoromethanesulfonic acid 2-fluoro-5-(7-trifluoromethyl-[1,8]naphthyridin-4-yl)phenyl ester (30.0 mg, 0.068 mmol), 3-chlorobenzeneboronic acid (13.9 mg, 0.089 mmol), dichlorobis-(triphenylphosphine)palladium (II) (5.0 mg, 7.1 µmol) and 2 M sodium carbonate solution (0.5 mL) in DME (3 mL) was irradiated in a microwave reactor at 150° C. for 10 min. After cooling to room temperature, the mixture was diluted with dichloromethane (3 mL) and water (3 mL), and was filtered through a PTFE cartridge. The separated organic phase was concentrated in vacuo, and the residual material was purified by preparative thin layer chromatography on silica gel, eluting with 5% ethyl acetate in dichloromethane, affording 5-(3'-chloro-6-fluorobiphenyl-3-yl)-2-trifluoromethyl[1,8]naphthyridine as a white solid (12.7 mg, 46%). $\delta_H$ (360 MHz, CDCl$_3$) 7.33–7.50 (5H, m), 7.57 (1H, dd, J 1.8 and 7.0), 7.59–7.60 (2H, m), 7.84 (1H, d, J 8.8), 8.54 (1H, d, J 8.8), 9.29 (1H, d, J 4.2). m/z (ES$^+$) 403, 405 [MH]$^+$.

EXAMPLE 36

N-[2'-Fluoro-5'-(7-trifluoromethyl[1,8]naphthyridin-4-yl)biphenyl-3-yl]acetamide Trifluoromethanesulfonic acid 2-fluoro-5-(7-trifluoromethyl[1,8]naphthyridin-4-yl)phenyl ester (30.0 mg, 0.068 mmol) was coupled to 3-acetamidophenylboronic acid (15.9 mg, 0.089 mmol) as described in Example 35 part c), affording N-[2'-fluoro-5'-(7-trifluoromethyl[1,8]naphthyridin-4-yl)biphenyl-3-yl]acetamide (12.0 mg, 41%). $\delta_H$ (360 MHz, CDCl$_3$) 2.20 (3H, s), 7.35–7.47 (5H, m), 7.54–7.60 (2H, m), 7.84 (1H, d, J 8.4), 7.87 (1H, s), 8.56 (1H, d, J 8.8), 9.28 (1H, d, J 4.6). m/z (ES$^+$) 426 [MH]$^+$.

EXAMPLE 37

1-[2'-Fluoro-5'-(7-trifluoromethyl[1,8]naphthyridin-4-yl)biphenyl-3-yl]ethanone

Trifluoromethanesulfonic acid 2-fluoro-5-(7-trifluoromethyl-[1,8]naphthyridin-4-yl)phenyl ester (30.0 mg, 0.068 mmol) was coupled to 3-acetylphenyl-boronic acid (14.5 mg, 0.089 mmol) as described in Example 35 part c), affording 1-[2'-fluoro-5'-(7-trifluoromethyl[1,8]naphthyridin-4-yl)biphenyl-3-yl]ethanone (16.8 mg, 60%). $\delta_H$ (360 MHz, CDCl$_3$) 2.66 (3H, s), 7.39–7.44 (1H, dd, J 9.8 and 8.4), 7.47–7.52 (1H, m), 7.58–7.62 (3H, m), 7.80–7.85 (2H, m), 8.01 (1H, dt, J 7.7, 1.2), 8.18 (1H, d, J 1.4), 8.55 (1H, d, J 8.8), 9.30 (1H, d, J 4.6). m/z (ES$^+$) 411 [MH]$^+$.

EXAMPLE 38

5-(6-Fluoro-2'-methoxybiphenyl-3-yl)-2-trifluoromethyl[1,8]naphthyridine

Trifluoromethanesulfonic acid 2-fluoro-5-(7-trifluoromethyl[1,8]naphthyridin-4-yl)phenyl ester (30.0 mg, 0.068 mmol) was coupled to 2-methoxyphenyl-boronic acid (13.5 mg, 0.089 mmol) as described in Example 35 part c), affording 5-(6-fluoro-2'-methoxybiphenyl-3-yl)-2-trifluoromethyl[1,8]-naphthyridine (14.5 mg, 53%). $\delta_H$ (360 MHz, CDCl$_3$) 3.86 (3H, s), 7.03–7.09 (2H, m), 7.32–7.48 (4H, m), 7.55 (1H, dd, J 2.5 and 6.7), 7.60 (1H, d, J 4.6), 7.83 (1H, d, J 8.4), 8.66 (1H, d, J 8.4), 9.27 (1H, d, J 4.6). m/z (ES$^+$) 399 [MH]$^+$.

EXAMPLE 39

5-(6-Fluoro-2'-trifluoromethylbiphenyl-3-yl)-2-trifluoromethyl[1,8]naphthyridine Trifluoromethanesulfonic acid 2-fluoro-5-(7-trifluoromethyl[1,8]naphthyridin-4-yl)phenyl ester (30.0 mg, 0.068 mmol) was coupled to 2-(trifluoromethyl)phenylboronic acid (16.8 mg, 0.089 mmol) as described in Example 35 part c), affording 5-(6-fluoro-2'-methoxybiphenyl-3-yl)-2-trifluoromethyl[1,8]naphthyridine (15.3 mg, 51%). $\delta_H$ (360 MHz, CDCl$_3$) 7.35–7.43 (3H, m), 7.51–7.66 (4H, m), 7.81–7.86 (2H, m), 8.55 (1H, d, J 8.8), 9.27 (1H, d, J 4.6). m/z (ES$^+$) 437 [MH]$^+$.

EXAMPLE 40

5-(4-Fluoro-3-pyrimidin-5-ylphenyl)-2-trifluoromethyl[1,8]naphthyridine

Trifluoromethanesulfonic acid 2-fluoro-5-(7-trifluoromethyl[1,8]naphthyridin-4-yl)phenyl ester (30.0 mg, 0.068 mmol) was coupled to 5-pyrimidinylboronic acid (prepared as described in WO 9411372; 11.0 mg, 0.089 mmol) as described in Example 35 part c), affording 5-(4-fluoro-3-pyrimidin-5-ylphenyl)-2-trifluoromethyl[1,8] naphthyridine (10.3 mg, 41%). $\delta_H$ (360 MHz, CDCl$_3$) 7.49 (1H, t, J 9.5), 7.55–7.61 (3H, m), 7.86 (1H, d, J 8.4), 8.51 (1H, d, J 8.4), 9.01 (2H, d, J 1.1), 9.28 (1H, s), 9.32 (1H, d, J 4.6). m/z (ES$^+$) 371 [MH]$^+$.

EXAMPLE 41

5-(4-Fluoro-3-quinolin-6-ylphenyl)-2-trifluoromethyl[1,8]naphthyridine

Trifluoromethanesulfonic acid 2-fluoro-5-(7-trifluoromethyl[1,8]naphthyridin-4-yl)phenyl ester (30.0 mg, 0.068 mmol) was coupled to 6-quinolinylboronic acid (15.3 mg, 0.089 mmol) as described in Example 35 part c), affording 5-(4-fluoro-3-quinolin-6-ylphenyl)-2-trifluoromethyl[1,8]naphthyridine (17.4 mg, 61%). $\delta_H$ (400 MHz, CDCl$_3$) 7.43–7.57 (3H, m), 7.64 (1H, d, J 4.3), 7.69–7.72 (1H, m), 7.85 (1H, d, J 8.6), 7.97 (1H, dt, J 8.6 and 1.8), 8.06 (1H, s), 8.22 (2H, d, J 8.2), 8.59 (1H, d, J 8.6), 8.98 (1H, dd, J 1.8 and 4.1), 9.30 (1H, d, J 4.3). m/z (ES$^+$) 420 [MH]$^+$.

EXAMPLE 42

5-(4-Fluoro-3-thiazol-2-ylphenyl)-2-trifluoromethyl[1,8]naphthyridine

A mixture of trifluoromethanesulfonic acid 2-fluoro-5-(7-trifluoromethyl-[1,8]naphthyridin-4-yl)phenyl ester (30.0 mg, 0.068 mmol), 2-tributylstannanethiazole (51.0 mg, 0.14 mmol), copper(I) iodide (1.3 mg, 6.8 μmol) and tetrakis(triphenylphosphine)palladium(0) (7.9 mg, 6.8 μmol) in DME (3 mL) was irradiated in a microwave reactor at 150° C. for 10 min. The mixture was allowed to cool, and was then diluted with water (3 mL) and dichloromethane (3 mL). The biphasic mixture was filtered through a PTFE cartridge, and the separated organic layer was concentrated in vacuo. The residue was purified by preparative thin layer chromatography, eluting with 25% ethyl acetate in dichloromethane, affording 5-(4-fluoro-3-thiazol-2-ylphenyl)-2-trifluoromethyl[1,8]naphthyridine as a pale yellow solid (7.5 mg, 29%). $\delta_H$ (360 MHz, CDCl$_3$) 7.40–7.56 (3H, m), 7.63 (1H, d, J 4.2), 7.84 (1H, d, J 8.4), 7.96 (1H, t, J 2.6), 8.49–8.55 (2H, m), 9.30 (1H, d, J 4.2). m/z (ES$^+$) 376 [MH]$^+$.

EXAMPLE 43

5-(4-Fluoro-3-pyrazin-2-ylphenyl)-2-trifluoromethyl[1,8]naphthyridine

Trifluoromethanesulfonic acid 2-fluoro-5-(7-trifluoromethyl[1,8]naphthyridin-4-yl)phenyl ester (30.0 mg, 0.068 mmol) was coupled to 2-tributylstannylpyrazine (50.2 mg, 0.14 mmol) as described in Example 42, affording 5-(4-fluoro-3-pyrazin-2-ylphenyl)-2-trifluoromethyl[1,8]naphthyridine (8.4 mg, 33%). $\delta_H$ (360 MHz, CDCl$_3$) 7.46 (1H, dd, J 10.5 and 8.4), 7.56–7.61 (1H, m), 7.63 (1H, d, J 4.2), 7.85 (1H, d, J 8.4), 8.24 (1H, dd, J 2.3 and 7.2), 8.55 (1H, d, J 8.8), 8.60 (1H, d, J 2.5), 8.68–8.69 (1H, m), 9.23 (1H, t, J 1.9), 9.30 (1H, d, J 4.6). m/z (ES$^+$) 371 [MH]$^+$.

EXAMPLE 44

5-(4-Fluoro-3-trifluoromethylphenyl)-2-trifluoromethyl[1,8]naphthyridine

5-Chloro-2-trifluoromethyl[1,8]naphthyridine (200 mg, 0.86 mmol) was coupled to 3-(trifluoromethyl)phenylboronic acid (212 mg, 1.1 mmol) as described in Example 3 part g), affording 5-(4-fluoro-3-trifluoromethylphenyl)-2-trifluoromethyl[1,8]naphthyridine (160 mg, 54%). $\delta_H$ (400 MHz, CDCl$_3$) 7.59 (1H, d, J 4.3), 7.68–7.76 (3H, m), 7.85 (2H, d, J 8.6), 8.43 (1H, d, J 8.2), 9.31 (1H, d, J 4.3). m/z (ES$^+$) 343 [MH]$^+$.

EXAMPLE 45

2-Fluoro-5-(7-trifluoromethyl[1,8]naphthyridine-4-yl)benzonitrile

5-Chloro-2-trifluoromethyl[1,8]naphthyridine (200 mg, 0.86 mmol) was coupled to 3-cyanophenylboronic acid (165 mg, 1.1 mmol) as described in Example 3 part g), affording 2-fluoro-5-(7-trifluoromethyl[1,8]naphthyridine-4-yl)benzonitrile (143 mg, 56%). $\delta_H$ (360 MHz, CDCl$_3$) 7.57 (1H, d, J 4.2), 7.71–7.91 (5H, m), 8.40 (1H, d, J 8.8), 9.32 (1H, d, J 4.2). m/z (ES$^+$) 300 [MH]$^+$.

EXAMPLE 46

2-[6-(7-Trifluoromethyl[1,8]naphthyridin-4-yl)pyridin-2-yl]benzonitrile a) 2-(6-Bromopyridin-2-yl)benzonitrile A mixture of 2,6-dibromopyridine (2.07 g, 8.7 mmol), 2-(4,4,5,5-tetramethyl[1,3,2]-dioxaborolan-2-yl)benzonitrile (prepared as described in Tetrahedron (2001), 57(49), 9813–9816, 3.00 g, 13 mmol) and potassium phosphate (3.71 g, 17 mmol) in DMF (40 mL) was degassed with nitrogen. Tetrakis(triphenylphosphine)palladium(0) (303 mg, 0.26 mmol) was added, the mixture was degassed as before, and was then stirred at 80° C. under nitrogen overnight. The mixture was partitioned between water and ethyl acetate, and the resulting aqueous layer was washed with ethyl acetate (2×100 mL). The combined organic layers were washed with water (1×100 mL) and saturated sodium chloride solution (1×100 mL), then were dried over magnesium sulfate and concentrated in vacuo. The residual material was purified by flash chromatography on silica gel, eluting with 50% ethyl acetate in isohexane, affording 2-(6-bromopyridin-2-yl)benzonitrile as a solid (680 mg, 30%). $\delta_H$ (400 MHz, CDCl$_3$) 7.51–7.57 (2H, m), 7.68–7.73 (2H, m), 7.80 (2H, d, J 7.7), 7.91 (1H, dd, J 0.7 and 7.7).

b) 2-[6-(7-Trifluoromethyl[1,8]naphthyridin-4-yl)pyridin-2-yl]benzonitrile

A mixture of 5-Chloro-2-trifluoromethyl[1,8]naphthyridine (200 mg, 0.86 mmol) and hexamethylditin (178 μL, 282 mg, 0.86 mmol) in DME (5 mL) was degassed via three "freeze-thaw" cycles. Tetrakis(triphenylphosphine)palladium(0) (49.7 mg, 0.043 mmol) was added, and the mixture was degassed as before, then was heated under nitrogen at 80° C. overnight. 2-(6-Bromopyridin-2-yl)benzonitrile (126 mg, 0.48 mmol) was added and the mixture was degassed as before, then more tetrakis (triphenylphosphine)palladium(0) (49.7 mg, 0.043 mmol) was added, the mixture was degassed again, then was stirred at 80° C. under nitrogen overnight. Water (25 mL) and dichloromethane (15 mL) were added to the cooled mixture, and the aqueous layer was washed with more dichloromethane (2×15 mL). The combined organic layers were washed with saturated sodium chloride solution (1×25 mL) then were dried over magnesium sulfate and concentrated in vacuo. The residual material was purified by flash chromatography on silica gel, eluting with 10% to 40% ethyl acetate in dichloromethane, affording 2-[6-(7-trifluoromethyl[1,8]naphthyridin-4-yl)pyridin-2-yl]benzonitrile as a colourless solid, which was recrystallised from ethyl acetate/isohexane (44 mg, 24%). $\delta_H$ (400 MHz, CDCl$_3$) 7.52–7.60 (1H, td, J 7.6 and 1.2), 7.71–7.77 (2H, m), 7.82 7.92 (5H, m), 8.12 (1H, t, J 7.8), 9.11 (1H, d, J 8.6), 9.35 (1H, d, J 4.3). m/z (ES$^+$) 377 [MH]$^+$.

EXAMPLE 47

5-[4-Fluoro-3-(pyridin-3-ylmethoxy)phenyl]-2-trifluoromethyl[1,8]naphthyridine

2-Fluoro-5-(7-trifluoromethyl[1,8]naphthyridin-4-yl)phenol (prepared as described in Example 35 part a), 50.0 mg, 0.16 mmol), caesium carbonate (159 mg, 0.49 mmol) and 3-(chloromethyl)pyridine hydrochloride (31.9 mg, 0.20 mmol) were stirred together in DMF (3 mL) at room temperature under nitrogen overnight. The mixture was partitioned between dichloromethane (3 mL) and water (3 mL), then was filtered through a PTFE cartridge. The separated organic phase was concentrated in vacuo, and residue was purified by flash chromatography on silica gel, eluting with 1:1 dichloromethane:ethyl acetate, then with ethyl acetate, affording 5-[4-fluoro-3-(pyridin-3-ylmethoxy)phenyl]-2-trifluoromethyl[1,8]naphthyridine as a colourless oil, which solidified upon trituration with isohexane (45.1 mg, 70%). $\delta_H$ (400 MHz, CDCl$_3$) 5.22 (2H, s), 7.06–7.12 (2H, m), 7.30–7.38 (2H, m), 7.52 (1H, d, J 4.3), 7.79 (1H, d, J 8.6), 7.81–7.83 (1H, m), 8.39 (1H, d, J 8.6), 8.64 (1H, dd, J 1.6 and 4.7), 8.69 (1H, d, J 2.0), 9.26 (1H, d, J 4.3). m/z (ES$^+$) 400 [MH]$^+$.

EXAMPLE 48

5-[4-Fluoro-3-(pyridin-4-ylmethoxy)phenyl]-2-trifluoromethyl[1,8]naphthyridine

2-Fluoro-5-(7-trifluoromethyl[1,8]naphthyridin-4-yl)phenol (50.0 mg, 0.16 mmol) was alkylated with 4-(chloromethylpyridine) hydrochloride (31.9 mg, 0.20 mmol) as described in Example 47, affording 5-[4-fluoro-3-(pyridin-4-ylmethoxy)phenyl]-2-trifluoromethyl[1,8]naphthyridine (39.7 mg, 61%). $\delta_H$ (360 MHz, CDCl$_3$) 5.23 (2H, s), 7.04 (1H, dd, J 7.7 and 1.8), 7.06–7.10 (1H, m), 7.33 (1H, dd, J 8.1 and 2.5), 7.38 (2H, d, J 6.0), 7.50 (1H, d, J 4.6), 7.76 (1H, d, J 8.8), 8.32 (1H, d, J 8.8), 8.66 (2H, d, J 6.0), 9.25 (1H, d, J 4.6). m/z (ES$^+$) 400 [MH]$^+$.

EXAMPLE 49

5-[4-Fluoro-3-(pyridin-2-yloxy)phenyl]-2-trifluoromethyl[1,8]naphthyridine

2-Fluoro-5-(7-trifluoromethyl[1,8]naphthyridin-4-yl)phenol (50.0 mg, 0.16 mmol) was alkylated with 2-bromopyridine (18.6 μL, 30.8 mg, 0.20 mmol) as described in Example 47, except that heating at 150° C. overnight was required, affording 5-[4-fluoro-3-(pyridin-2-yloxy)phenyl]-2-trifluoromethyl[1,8]naphthyridine (15.1 mg, 24%). $\delta_H$ (400 MHz, CDCl$_3$) 7.04–7.09 (2H, m), 7.30–7.35 (1H, m), 7.38–7.43 (2H, m), 7.60 (1H, d, J 4.7), 7.73–7.79 (1H, m), 7.83 (1H, d, J 8.6), 8.17 (1H, dd, J 5.1 and 2.0), 8.64 (1H, d, J 8.6), 9.27 (1H, d, J 4.3). m/z (ES$^+$) 386 [MH]$^+$.

EXAMPLE 50

[2-Fluoro-5-(7-trifluoromethyl[1,8]naphthyridin-4-yl)phenoxy]acetonitrile

2-Fluoro-5-(7-trifluoromethyl[1,8]naphthyridin-4-yl)phenol (50.0 mg, 0.16 mmol) was alkylated with chloroacetonitrile (24.6 μL, 29.4 mg, 0.39 mmol) as described in Example 47, affording[2-fluoro-5-(7-trifluoromethyl[1,8]-naphthyridin-4-yl)phenoxy]acetonitrile (33.4 mg, 59%). $\delta_H$ (400 MHz, CDCl$_3$) 4.94 (2H, s), 7.23–7.29 (2H, m), 7.40 (1H, dd, J 8.2 and 10.6), 7.56 (1H, d, J 4.3), 7.85 (1H, d, J 8.6), 8.53 (1H, d, J 8.6), 9.28 (1H, d, J 4.7). m/z (ES$^+$) 348 [MH]$^+$.

EXAMPLE 51

2-[2-Fluoro-5-(7-trifluoromethyl[1,8]naphthyridin-4-yl)phenoxy]-N,N-dimethylacetamide 2-Fluoro-5-(7-trifluoromethyl[1,8]naphthyridin-4-yl)phenol (50.0 mg, 0.16 mmol) was alkylated with 2-chloro-N,N-dimethylacetamide (20.1 μL, 23.7 mg, 0.20 mmol) as described in Example 47, affording 2-[2-fluoro-5-(7-trifluoromethyl[1,8]naphthyridin-4-yl)phenoxy]-N,N-dimethylacetamide (36.8 mg, 58%). $\delta_H$ (360 MHz, CDCl$_3$) 2.99 (3H, s), 3.10 (3H, s), 4.85 (2H, s), 7.05–7.09 (1H, m), 7.18 (1H, dd, J 2.1 and 8.1), 7.31 (1H, dd, J 8.1 and 10.9), 7.54 (1H, d, J 4.2), 7.82 (1H, d, J 8.4), 8.53 (1H, d, J 8.4), 9.25 (1H, d, J 4.6). m/z (ES$^+$) 394 [MH]$^+$.

EXAMPLE 52

5-[4-Fluoro-3-(2-methyl-2H-[1,2,4]triazol-3-ylmethoxy)phenyl]-2-trifluoromethyl[1,8]naphthyridine 2-Fluoro-5-(7-trifluoromethyl[1,8]naphthyridin-4-yl)phenol (50.0 mg, 0.16 mmol) was alkylated with 5-chloromethyl-1-methyl-1H-[1,2,4]triazole hydrochloride (prepared as described in WO 0023449, 30.4 mg, 0.20 mmol) as described in Example 47, affording 5-[4-fluoro-3-(2-methyl-2H-[1,2,4]triazol-3-ylmethoxy)phenyl]-2-trifluoromethyl-[1,8]naphthyridine (37.8 mg, 58%). $\delta_H$ (360 MHz, CDCl$_3$) 4.06 (3H, s), 5.39 (2H, s), 7.08–7.12 (1H, m), 7.28–7.36 (2H, m), 7.51 (1H, d, J 4.2), 7.82 (1H, d, J 8.8), 7.87 (1H, s), 8.43 (1H, d, J 8.4), 9.27 (1H, d, J 4.6). m/z (ES$^+$) 404 [MH]$^+$.

EXAMPLE 53

5-[4-Fluoro-3-(1-methyl-1H-[1,2,3]triazol-4-ylmethoxy)phenyl]-2-trifluoromethyl[1,8]naphthyridine 2-Fluoro-5-(7-trifluoromethyl[1,8]naphthyridin-4-yl)phenol (50.0 mg, 0.16 mmol), resin-bound triphenylphosphine (180 mg of 3 mmol/g resin, 5.4 mmol), diisopropylazodicarboxylate (76.8 μL, 78.8 mg, 0.40 mmol) and 1-methyl-1H-1,2,3-triazole-4-methanol (prepared as described in WO 0023449, 22.0 mg, 0.20 mmol) were stirred together in THF (3 mL) at room temperature overnight. The mixture was filtered, and the filtrate was diluted with dichloromethane (15 mL), was washed with 1 N sodium hydroxide (2×10 mL), was dried over magnesium sulfate and was concentrated in vacuo. The residue was purified by flash chromatography on silica gel, eluting with 2.5% methanol in dichloromethane, affording 5-[4-fluoro-3-(1-methyl-1H-[1,2,3]triazol-4-ylmethoxy)phenyl]-2-trifluoromethyl[1,8]naphthyridine as a colourless solid, which was recrystallised from ethyl acetate/isohexane (26.7 mg, 41%). $\delta_H$ (360 MHz, CDCl$_3$) 4.13 (3H, s), 5.35 (2H, s), 7.03–7.07 (1H, m), 7.25–7.31 (1H, m), 7.38 (1H, dd, J 2.1 and 7.7), 7.54 (1H, d, J 4.6), 7.70 (1H, s), 7.86 (1H, d, J 8.8), 8.53 (1H, d, J 8.8), 9.26 (1H, d, J 4.2). m/z (ES$^+$) 404 [MH]$^+$.

EXAMPLE 54

5-(4-Fluorophenyl)-2-trifluoromethyl[1,8]naphthyridine

In the attempted coupling of trifluoromethanesulfonic acid 2-fluoro-5-(7-trifluoromethyl[1,8]naphthyridin-4-yl)phenyl ester (30.0 mg, 0.068 mmol) with a 1:1 mixture of 3-(5,5-dimethyl[1,3,2]dioxaborinan-2-yl)-2-fluorobenzonitrile and 6-(5,5-dimethyl[1,3,2]dioxaborinan-2-yl)-2-fluorobenzonitrile (34.4 mg) following the procedure described in Example 35 part c), none of the expected product was obtained. Instead, the triflate was reduced, affording 5-(4-fluorophenyl)-2-trifluoromethyl[1,8]naphthyridine (13.9 mg, 42%). $\delta_H$ (360 MHz, CDCl$_3$) 7.27–7.31 (2H, m), 7.46–7.50 (2H, m), 7.55 (1H, d, J 4.6), 7.82 (1H, d, J 8.4), 8.49 (1H, d, J 8.8), 9.27 (1H, d, J 4.6). m/z (ES$^+$) 293 [MH]$^+$.

EXAMPLE 55

2'-Fluoro-5'-[7-(2-fluorophenyl)-[1,8]naphthyridin-4-yl]biphenyl-2-carbonitrile a) 5-Chloro-2-(2-fluorophenyl)-[1,8]naphthyridine A stirred mixture of 2,5-dichloro-[1,8]naphthyridine (Barlin, G. B.; Tan, W.-L. Aust. J. Chem. 1984, 37, 1065) (0.1029 g, 0.513 mmol) and 2-fluorobenzeneboronic acid (72.4 mg, 0.517 mmol) in 2 N aqueous sodium carbonate (0.620 mL, 1.24 mmol) and ethylene glycol dimethyl ether (3 mL) was degassed by bubbling nitrogen through for 15 min. Tetrakis-(triphenylphosphine)palladium(0) (29.9 mg, 0.0259 mmol) was added and the mixture was degassed for a further 10 min, then heated at 80° C. for 16 h under nitrogen. The mixture was partitioned between water (20 mL) and dichloromethane (20 mL). The aqueous layer was further extracted with dichloromethane (2×20 mL), and the combined organic extracts were dried (MgSO$_4$) and evaporated in vacuo. The residue was purified by flash chromatography on silica gel, eluting with 15% EtOAc/CH$_2$Cl$_2$, to afford 0.1216 g (91%) of the title compound as an off-white solid. $\delta_H$ (360 MHz, CDCl$_3$) 7.22 (1H, dd, J 11.8 and 8.2), 7.34 (1H, td, J 7.7, 0.7), 7.49 (1H, tdd, J 7.4, 5.3, and 2.1), 7.58 (1H, d, J 4.7), 8.18 (1H, dd, J 8.8, 2.5), 8.39 (1H, td, J 7.7, 1.8), 8.66 (1H, d, J 8.8), 9.03 (1H, d, J 4.8).

b) 2'-Fluoro-5'-[7-(2-fluorophenyl)-[1,8]naphthyridin-4-yl]biphenyl-2-carbonitrile This was prepared in 62% yield from 5-chloro-2-(2-fluorophenyl)-[1,8]naphthyridine (from step a) and 2'-fluoro-5'-(4,4,5,5-tetramethyl-[1,3,2]dioxaborolan-2-yl)biphenyl-2-carbonitrile (from Example 2, step e) using a similar procedure to that described in step a. $\delta_H$ (400 MHz, CDCl$_3$) 7.20 (1H, ddd, J 11.7, 8.2 and 1.2), 7.34 (1H, td, J 7.4, 1.2), 7.42–7.48 (2H, m), 7.50 (1H, d, J 4.3), 7.54 (1H, td, J 7.4, 1.2), 7.60–7.65 (3H, m), 7.71 (1H, td, J 7.4, 1.2), 7.84 (1H, dd, J 7.8, 0.8), 8.09 (1H, dd, J 8.6 and 2.3), 8.42 (1H, td, J 7.8, 2.0), 8.49 (1H, d, J 8.6), 9.18 (1H, d, J 4.7). m/z (ES$^+$) 420 [MH]$^+$.

EXAMPLE 56

2'-Fluoro-5'-[7-(pyridin-3-yl)-[1,8]naphthyridin-4-yl]biphenyl-2-carbonitrile a) 5-Chloro-2-(pyridin-3-yl)-[1,8]naphthyridine This was prepared in 66% yield by a similar procedure to that described for Example 55, step a, but using pyridine-3-boronic acid instead of 2-fluorobenzeneboronic acid and eluting with 5% MeOH/CH$_2$Cl$_2$. $\delta_H$ (360 MHz, CDCl$_3$) 7.50 (1H, ddd, J 7.8, 4.7, and 0.8), 7.60 (1H, d, J 4.7), 8.14 (1H, d, J 8.6), 8.71 (1H, dt, J 7.8, 2.0), 8.74 (1H, d, J 8.6), 8.76 (1H, dd, J 4.7, 1.6), 9.06 (1H, d, J 4.7), 9.46 (1H, d, J 2.0).

b)(2'-Fluoro-5'-[7-(pyridin-3-yl)-[1,8]naphthyridin-4-yl]biphenyl-2-carbonitrile This was prepared in 88% yield from 5-chloro-2-(pyridin-3-yl)-[1,8]naphthyridine (from step a) and 2'-fluoro-5'-(4,4,5,5-tetramethyl-[1,3,2]dioxaborolan-2-yl)biphenyl-2-carbonitrile (from Example 2, step e) using a similar procedure to that described in Example 55, step a. $\delta_H$ (400 MHz, CDCl$_3$) 7.44–7.52 (3H, m), 7.55 (1H, td, J 7.4, 1.2), 7.61–7.65 (3H, m), 7.71 (1H, td, J 7.4, 1.2), 7.85 (1H, dd, J 7.8, 1.2), 8.06 (1H, d, J 9.0), 8.59 (1H, d, J 8.6), 8.71–8.75 (2H, m), 9.20 (1H, d, J 4.7), 9.46 (1H, d, J 1.6). m/z (ES$^+$) 403 [MH]$^+$.

EXAMPLE 57

2'-Fluoro-5'-[7-(thiazol-2-yl)-[1,8]naphthyridin-4-yl]biphenyl-2-carbonitrile a) 5-Chloro-2-(thiazol-3-yl)-[1,8]naphthyridine A stirred mixture of 2,5-dichloro-[1,8]naphthyridine (Barlin, G. B.; Tan, W.-L. Aust. J. Chem. 1984, 37, 1065) (0.1019 g, 0.512 mmol) and 2-(thiazolyl)zinc bromide (0.5 M solution in THF, 1.08 mL, 0.540 mmol) in THF (2 mL) was degassed by bubbling nitrogen through for 15 min. Tetrakis-(triphenylphosphine)palladium(0) (59.6 mg, 0.0515 mmol) was added and the mixture was degassed for a further 10 min, then heated at 60° C. for 10 h under nitrogen. The mixture was partitioned between water (20 mL) and dichloromethane (20 mL). The aqueous layer was further extracted with dichloromethane (2×20 mL), and the combined organic extracts were dried (MgSO$_4$) and evaporated in vacuo. The residue was purified by flash chromatography on silica gel, eluting with 15% EtOAc/CH$_2$Cl$_2$, to afford 86.3 mg (68%) of the title compound as a white solid. $\delta_H$ (400 MHz, CDCl$_3$) 7.59 (1H, d, J 4.7), 7.60 (1H, d, J 3.1), 8.04 (1H, d, J 3.1), 8.56 (1H, d, J 8.6), 8.72 (1H, d, J 8.6), 9.03 (1H, d, J 4.7).

b) 2'-Fluoro-5'-[7-(thiazol-2-yl)-[1,8]naphthyridin-4-yl]biphenyl-2-carbonitrile This was prepared in 59% yield from 5-chloro-2-(thiazol-2-yl)-[1,8]naphthyridine (from step a) and 2'-fluoro-5'-(4,4,5,5-tetramethyl-[1,3,2]dioxaborolan-2-yl)biphenyl-2-carbonitrile (from Example 2, step e) using a similar procedure to that described in Example 55, step a. $\delta_H$ (400 MHz, CDCl$_3$) 7.45 (1H, t, J 9.0), 7.51 (1H, d, J 4.3), 7.54 (1H, td, J 7.4, 1.2), 7.58 (1H, d, J 3.1), 7.60–7.63 (3H, m), 7.71 (1H, td, J 7.4, 1.2), 7.84 (1H, dd, J 7.4, 1.2), 8.02 (1H, d, J 3.1), 8.48 (1H, d, J 8.6), 8.54 (1H, d, J 8.6), 9.46 (1H, d, J 4.7). m/z (ES$^+$) 409 [MH]$^+$.

EXAMPLE 58

5'-[7-Acetyl-[1,8]naphthyridin-4-yl]-2'-fluorobiphenyl-2-carbonitrile a) 1-(5-Chloro-[1,8]naphthyridin-2-yl)ethanone A stirred solution of 2,5-dichloro-[1,8]naphthyridine (Barlin, G. B.; Tan, W.-L. Aust. J. Chem. 1984, 37, 1065) (0.1001 g, 0.503 mmol) in 1,4-dioxane (5 mL) was degassed by bubbling nitrogen through for 15 min. Tetrakis(triphenylphosphine)palladium(0) (30.0 mg, 0.0259 mmol) and tributyl(1-ethoxyvinyl)tin (0.170 mL, 0.503 mmol) was added and the mixture was heated at 80° C. for 17 h under nitrogen. The mixture was diluted with ethyl acetate (20 mL) and shaken with 2 N aqueous HCl (15 mL) for 1 min. The mixture was adjusted to pH 6 with 4 N aqueous NaOH and the organic layer was separated. The aqueous layer was further extracted with ethyl acetate (2×15 mL), and the combined organic extracts were dried (MgSO$_4$) and evaporated in vacuo. The residue was purified by flash chromatography on silica gel, eluting with 15% EtOAc/CH$_2$Cl$_2$, followed by a further column on silica gel eluting with 50% EtOAc/isohexane, to afford 34.9 mg (34%) of the title compound as a white solid. $\delta_H$ (360 MHz, CDCl$_3$) 2.95 (3H, s), 7.68 (1H, d, J 4.6), 8.33 (1H, d, J 8.4), 8.76 (1H, d, J 8.8), 9.12 (1H, d, J 4.9).

b) 5'-[7-Acetyl-[1,8]naphthyridin-4-yl]-2'-fluorobiphenyl-2-carbonitrile

This was prepared in 83% yield from 1-(5-chloro-[1,8]naphthyridin-2-yl)ethanone (from step a) and 2'-fluoro-5'-(4,4,5,5-tetramethyl-[1,3,2]dioxaborolan-2-yl)biphenyl-2-carbonitrile (from Example 2, step e) using a similar procedure to that described in Example 55, step a. $\delta_H$ (400 MHz, CDCl$_3$) 2.97 (3H, s), 7.45 (1H, t, J 9.0), 7.55 (1H, td, J 7.4, 1.2), 7.58–7.62 (4H, m), 7.71 (1H, td, J 7.4, 1.2), 7.84 (1H, dd, J 7.8, 0.8), 8.26 (1H, d, J 8.6), 8.59 (1H, d, J 8.6), 9.26 (1H, d, J 4.3). m/z (ES$^+$) 368 [MH]$^+$.

EXAMPLE 59

2'-Fluoro-5'-[7-(1-hydroxy-1-methylethyl)-[1,8]naphthyridin-4-yl]biphenyl-2-carbonitrile To a stirred solution of 5'-[7-acetyl-[1,8]naphthyridin-4-yl]-2'-fluorobiphenyl-2-carbonitrile (from Example 58) (28.6 mg, 0.0778 mmol) in anhydrous THF (2 mL), cooled under nitrogen to −78° C., was added dropwise methylmagnesium bromide (3.0 M solution in Et$_2$O, 26.0 µL, 0.078 mmol). The mixture was stirred at −78° C. for a total of 85 min, adding more methylmagnesium bromide (3.0 M solution in Et$_2$O, 26.0 µL, 0.078 mmol) after 45 min and 70 min. Saturated aqueous NH$_4$Cl (2 mL) was then added and the mixture was allowed to warm to room temperature. The mixture was partitioned between ethyl acetate (15 mL) and water (10 mL). The aqueous layer was extracted further with ethyl acetate (15 mL), and the combined organic extracts were dried (MgSO$_4$) and evaporated in vacuo. The residue was purified by flash chromatography on silica gel, eluting with 3% MeOH/CH$_2$Cl$_2$, to afford 20.6 mg (69%) of the title compound as a white solid. $\delta_H$ (360 MHz, CDCl$_3$) 1.67 (6H, s), 5.32 (1H, s), 7.44 (1H, t, J 9.1), 7.51 (1H, d, J 4.6), 7.54 (1H, td, J 7.7, 1.1), 7.58–7.65 (4H, m), 7.71 (1H, td, J 7.7, 1.1), 7.84 (1H, dd, J 7.7, 1.1), 8.51 (1H, d, J 8.8), 9.15 (1H, d, J 4.2). m/z (ES$^+$) 384 [MH]$^+$.

What is claimed is:

1. A compound of formula I, or a pharmaceutically acceptable salt thereof:

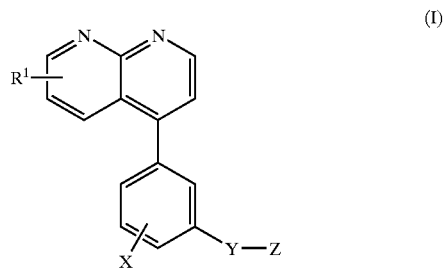

(I)

wherein:

X represents hydrogen or halogen;

Y represents a chemical bond, an oxygen atom, or —NH—;

Z represents phenyl, pyridinyl, thienyl or thiazolyl, which is unsubstituted or substituted with fluoro, chloro, methoxy, trifluoromethyl, cyano, nitro, amino, formyl, methoxycarbonyl or —CH=NOH;

R$^1$ represents hydrogen, C$_{1-6}$ alkyl, halo(C$_{1-6}$)alkyl, dihalo(C$_{1-6}$)alkyl, hydroxy(C$_{1-6}$)alkyl, C$_{1-6}$ alkoxy(C$_{1-6}$)alkyl, di(C$_{1-6}$)alkoxy(C$_{1-6}$)akyl, C$_{2-6}$ alkenyl, C$_{2-6}$ alkynyl, C$_{3-7}$ cycloalkyl, C$_{3-7}$ cycloalkyl(C$_{1-6}$)alkyl, indanyl, phenyl, phenyl(C$_{1-6}$)alkyl, azetidinyl, pyrrolidinyl, piperidinyl, piperazinyl, morpholinyl, thiomorpholinyl, pyridinyl, quinolinyl, isoquinolinyl, pyridazinyl, pyrimidinyl, pyrazinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl, tetrazolyl, halogen, cyano, trifluoromethyl, nitro, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$, —CONR$^a$R$^b$, —CR$^a$=NOR$^b$ or CR$^a$=NNHR$^b$, where R$^a$ is hydrogen or C$_{1-6}$ alkyl, and R$^b$ is hydrogen, C$_{1-6}$ alkyl, hydroxy(C$_{1-6}$)alkyl or di(C$_{1-6}$)alkylamino(C$_{1-6}$)alkyl.

2. The compound of claim 1 wherein Y is a bond; or a pharmaceutically acceptable salt thereof.

3. The compound of claim 1 wherein R$^1$ is methyl, fluoromethyl, difluoromethyl, trifluoromethyl, hydroxymethyl, methoxymethyl, dimethoxymethyl, hydroxyethyl, fluoroethyl, difluoroethyl, dimethoxyethyl, isopropyl, hydroxypropyl, fluoropropyl, tert-butyl, pyridyl, furyl, thienyl, oxazolyl, methylthiazolyl, methyloxadiazolyl, imidazolylmethyl, triazolylmethyl, chloro, methoxy, cyano, formyl, acetyl, methoxycarbonyl or —CR$^2$=NOR$^3$ in which R$^2$ is hydrogen or methyl and R$^3$ is hydrogen, hydroxyethyl or dimethylaminoethyl; or a pharmaceutically acceptable salt thereof.

4. The compound of claim 2 wherein $R^1$ is methyl, trifluoromethyl or 2-hydroxyprop-2-yl; or a pharmaceutically acceptable salt thereof.

5. The compound of claim 3 wherein X is hydrogen or fluoro; or a pharmaceutically acceptable salt thereof.

6. The compound of claim 3 wherein Z is an optionally substituted phenyl wherein there are one or two optional substituents selected from fluorine, cyano, trifluoromethyl; or a pharmaceutically acceptable salt thereof.

7. The compound of claim 6 wherein Z is phenyl, monofluorophenyl, difluorophenyl, trifluoromethylphenyl, cyanophenyl or cyanofluorophenyl; or a pharmaceutically acceptable salt thereof.

8. The compound of claim 1 of formula IIB, or a pharmaceutically acceptable salt thereof:

(IIB)

wherein:

$R^{11}$ is selected from the group consisting of: methyl, fluoromethyl, difluoromethyl, trifluoromethyl, hydroxymethyl, methoxymethyl, dimethoxymethyl, hydroxyethyl, fluoroethyl, difluoroethyl, dimethoxyethyl, isopropyl, hydroxypropyl, fluoropropyl, tert-butyl, pyridinyl, furyl, thienyl, oxazolyl, methylthiazolyl, methyloxadiazolyl, imidazolylmethyl, triazolylmethyl, chloro, methoxy, cyano, formyl, acetyl, methoxycarbonyl and —$CR^2$=$NOR^3$, where $R^2$ represents hydrogen or methyl, and $R^3$ represents hydrogen, hydroxyethyl or dimethylaminoethyl; and $X^1$ represents hydrogen or fluoro.

9. A compound which is selected from the group consisting of:

3'-(7-methyl-[1,8]naphthyridin-4-yl)biphenyl-2-carbonitrile;

2'-fluoro-5'-(7-methyl-[1,8]naphthyridin-4-yl)biphenyl-2-carbonitrile;

6,2'-difluoro-5'-(7-trifluoromethyl[1,8]naphthyridin-4-yl)biphenyl-2-carbonitrile;

5-(4-fluoro-3-pyridin-3-ylphenyl)-2-trifluoromethyl[1,8]naphthyridine;

5-(4-fluoro-3-pyridin-4-ylphenyl)-2-trifluoromethyl[1,8]naphthyridine;

5-[4-fluoro-3-(3-fluoropyridin-2-yl)phenyl]-2-trifluoromethyl[1,8]naphthyridine;

3,2'-difluoro-5'-(7-trifluoromethyl-[1,8]naphthyridin-4-yl)biphenyl-2-carbonitrile;

4,2'-difluoro-5'-(7-trifluoromethyl-[1,8]naphthyridin-4-yl)biphenyl-2-carbonitrile;

5,2'-difluoro-5'-(7-trifluoromethyl-[1,8]naphthyridin-4-yl)biphenyl-2-carbonitrile;

4-fluoro-3'-(7-trifluoromethyl[1,8]naphthyridin-4-yl)biphenyl-2-carbonitrile;

5-(2-fluoro-3-pyridin-2-ylphenyl)-2-trifluoromethyl-[1,8]naphthyridine;

5-(2-fluoro-3-pyridin-3-ylphenyl)-2-trifluoromethyl-[1,8]naphthyridine;

5-(2-fluoro-3-pyridin-4-ylphenyl)-2-trifluoromethyl-[1,8]naphthyridine;

5-(2,4-difluoro-3-pyridin-3-ylphenyl)-2-trifluoromethyl[1,8]naphthyridine;

5-(2,4-difluoro-3-pyridin-4-ylphenyl)-2-trifluoromethyl[1,8]naphthyridine;

3'-fluoro-5'-(7-trifluoromethyl-[1,8]naphthyridin-4-yl)biphenyl-2-carbonitrile;

2'-fluoro-5'-(7-trifluoromethyl-[1,8]naphthyridin-4-yl)biphenyl-3-carbonitrile;

2'-fluoro-5'-(7-trifluoromethyl[1,8]naphthyridin-4-yl)biphenyl-4-carbonitrile;

5-(6-fluoro-2'-methanesulfonylbiphenyl-3-yl)-2-trifluoromethyl[1,8]-naphthyridine;

5-(3'-methoxybiphenyl-3-yl)-2-trifluoromethyl[1,8]naphthyridine;

5-[4-fluoro-3-(3-fluoropyridin-4-yl)phenyl]-2-trifluoromethyl[1,8]naphthyridine;

2-[2-fluoro-5-(7-trifluoromethyl[1,8]naphthyridin-4-yl)phenyl]nicotinonitrile;

2-[2-fluoro-5-(7-trifluoromethyl[1,8]naphthyridin-4-yl)phenyl]nicotinamide;

5-(3-fluoro-5-pyridin-3-ylphenyl)-2-trifluoromethyl[1,8]naphthyridine;

5-(4-fluoro-3-pyrimidin-4-ylphenyl)-2-trifluoromethyl[1,8]naphthyridine;

5-[3-(2-methyl-2H-tetrazol-5-yl)phenyl]-2-trifluoromethyl[1,8]naphthyridine;

5-(3-furan-2-ylphenyl)-2-trifluoromethyl[1,8]naphthyridine;

5-[3-(pyridin-2-ylmethoxy)phenyl]-2-trifluoromethyl[1,8]naphthyridine;

5-(4-fluoro-3-morpholin-4-ylmethylphenyl)-2-trifluoromethyl[1,8]naphthyridine;

5-[3-(3,5-difluoropyridin-2-yl)-4-fluorophenyl]-2-trifluoromethyl[1,8]-naphthyridine;

2'-fluoro-5'-(7-trifluoromethyl[1,8]naphthyridin-4-yl)biphenyl-2-carbonitrile;

5-(4-fluoro-3-pyridin-2-yl)-2-trifluoromethyl[1,8]naphthyridine;

6,2'-difluoro-5'-(7-trifluoromethyl[1,8]naphthyridin-4-yl)biphenyl-3-carbonitrile;

5-(4-fluoro-3-methoxyphenyl)-2-trifluoromethyl[1,8]naphthyridine;

5-(3'-chloro-6-fluorobiphenyl-3-yl)-2-trifluoromethyl[1,8]naphthyridine;

N-[2'-fluoro-5'-(7-trifluoromethyl[1,8]naphthyridin-4-yl)biphenyl-3-yl]acetamide;

1-[2'-fluoro-5'-(7-trifluoromethyl[1,8]naphthyridin-4-yl)biphenyl-3-yl]ethanone;

5-(6-fluoro-2'-methoxybiphenyl-3-yl)-2-trifluoromethyl[1,8]naphthyridine;

5-(6-fluoro-2'-trifluoromethylbiphenyl-3-yl)-2-trifluoromethyl[1,8]naphthyridine;

5-(4-fluoro-3-pyrimidin-5-ylphenyl)-2-trifluoromethyl[1,8]naphthyridine;

5-(4-fluoro-3-quinolin-6-ylphenyl)-2-trifluoromethyl[1,8]naphthyridine;

5-(4-fluoro-3-thiazol-2-ylphenyl)-2-trifluoromethyl[1,8]naphthyridine;

5-(4-fluoro-3-pyrazin-2-ylphenyl)-2-trifluoromethyl[1,8]naphthyridine;

5-(4-fluoro-3-trifluoromethylphenyl)-2-trifluoromethyl[1,8]naphthyridine;

2-fluoro-5-(7-trifluoromethyl[1,8]naphthyridine-4-yl)benzonitrile;

2-[6-(7-trifluoromethyl[1,8]naphthyridin-4-yl)pyridin-2-yl]benzonitrile;

5-[4-fluoro-3-(pyridin-3-ylmethoxy)phenyl]-2-trifluoromethyl[1,8]naphthyridine;

5-[4-fluoro-3-(pyridin-4-ylmethoxy)phenyl]-2-trifluoromethyl[1,8]naphthyridine;

5-[4-fluoro-3-(pyridin-2-yloxy)phenyl]-2-trifluoromethyl[1,8]naphthyridine;

[2-fluoro-5-(7-trifluoromethyl[1,8]naphthyridin-4-yl)phenoxy]acetonitrile;

2-[2-fluoro-5-(7-trifluoromethyl[1,8]naphthyridin-4-yl)phenoxy]-N,N-dimethylacetamide;

5-[4-fluoro-3-(2-methyl-2H-[1,2,4]triazol-3-ylmethoxy)phenyl]-2-trifluoromethyl[1,8]naphthyridine;

5-[4-fluoro-3-(1-methyl-1H-[1,2,3]triazol-4-ylmethoxy)phenyl]-2-trifluoromethyl[1,8]naphthyridine;

5-(4-fluorophenyl)-2-trifluoromethyl[1,8]naphthyridine;

2'-fluoro-5'-[7-(2-fluorophenyl)-[1,8]naphthyridin-4-yl]biphenyl-2-carbonitrile;

2'-fluoro-5'-[7-(pyridin-3-yl)-[1,8]naphthyridin-4-yl]biphenyl-2-carbonitrile;

2'-fluoro-5'-[7-(thiazol-2-yl)-[1,8]naphthyridin-4-yl]biphenyl-2-carbonitrile;

5'-[7-acetyl-[1,8]naphthyridin-4-yl]-2'-fluorobiphenyl-2-carbonitrile;

2'-fluoro-5'-[7-(1-hydroxy-1-methylethyl)-[1,8]naphthyridin-4-yl]biphenyl-2-carbonitrile;

or a pharmaceutically acceptable salt thereof.

10. A pharmaceutical composition comprising the compound of claim 1 or a pharmaceutically acceptable salt thereof and a pharmaceutically acceptable carrier.

11. A method for the treatment of anxiety which comprises administering to a patient in need of such treatment an effective amount of the compound of claim 1 or a pharmaceutically acceptable salt thereof.

* * * * *